United States Patent
Mor et al.

(10) Patent No.: US 6,440,690 B1
(45) Date of Patent: Aug. 27, 2002

(54) PEPTIDES FOR THE ACTIVATION OF THE IMMUNE SYSTEM IN HUMANS AND ANIMALS

(75) Inventors: Amram Mor, 3, rue du Pas de la Mule, Paris (FR), 75004; Ioannis Vouldoukis, Antony (FR); Pierre Nicolas, Tourny (FR)

(73) Assignee: Amram Mor, Jerusalem (IL)

( * ) Notice: Subject to any disclaimer, the term of this patent is extended or adjusted under 35 U.S.C. 154(b) by 0 days.

(21) Appl. No.: 09/181,941

(22) Filed: Oct. 28, 1998

Related U.S. Application Data

(63) Continuation of application No. 08/574,701, filed on Dec. 19, 1995, now abandoned.

(30) Foreign Application Priority Data

Jun. 29, 1995 (FR) .............................................. 95 07831

(51) Int. Cl.$^7$ .......................... C12Q 1/18; A61K 39/00; A61K 38/16; A61K 38/00; C07K 1/00
(52) U.S. Cl. .......................... 435/32; 424/184.1; 514/6; 514/21; 530/350
(58) Field of Search .......................... 424/184.1; 514/6, 514/12, 13, 21; 530/350; 435/32

(56) References Cited

U.S. PATENT DOCUMENTS

| | | | |
|---|---|---|---|
| 5,008,371 A | 4/1991 | Narori .......................... 530/324 |
| 5,017,486 A | 5/1991 | Sawai et al. .............. 435/172.3 |
| 5,073,542 A | 12/1991 | Zasloff .......................... 514/12 |
| 5,106,735 A | 4/1992 | Natori et al. .................. 435/91 |
| 5,118,789 A | 6/1992 | Natori .......................... 534/300 |
| 5,206,154 A | 4/1993 | Lai et al. .................... 435/69.7 |
| 5,221,664 A | 6/1993 | Berkowitz et al. ............. 514/6 |
| 5,304,633 A | 4/1994 | Tomita et al. ............... 530/326 |
| 5,317,084 A | 5/1994 | Tomita et al. ............... 530/324 |
| 5,348,942 A | 9/1994 | Little, II et al. ............... 514/12 |
| 5,424,290 A | 6/1995 | Maloy et al. .................. 514/13 |
| 5,686,563 A | * 11/1997 | Kari ............................ 530/326 |

FOREIGN PATENT DOCUMENTS

| | | |
|---|---|---|
| EP | 045 665 A1 | 2/1982 |
| EP | 045 665 B1 | 9/1985 |
| EP | 280 859 (A2 A3 | 9/1988 |
| EP | 303 859 (A2 A3 | 2/1989 |
| EP | 280 859 B1 | 7/1992 |
| EP | 503 939 A1 | 9/1992 |
| EP | 519 726 (A2 A3 | 12/1992 |
| EP | 303 859 B1 | 5/1993 |
| EP | 519 726 B1 | 4/1997 |
| EP | 503 939 B1 | 6/1997 |
| FR | 2735983 | 1/1997 |
| JP | 6080695 | 3/1994 |

(List continued on next page.)

OTHER PUBLICATIONS

Cohen; Jitters jeopardize AIDS vaccine trial; Science; vol. 262, pp. 980–981, Nov. 1993.*

Fox; No winners against AIDS; Bio/Tech.; vol. 12, pp. 128, Feb. 1994.*

Butini et al.; Comparative analysis of HIV–specific CTI activity in lymphoid tissue and peripheral blood; J. Cell. Biochem.; supp. 18B, J 306, Feb. 94.*

(List continued on next page.)

*Primary Examiner*—Hankyel T. Park
(74) *Attorney, Agent, or Firm*—Pennie & Edmonds LLP

(57) ABSTRACT

The present invention is directed to compositions and methods for the treatment of diseases comprising the administration of compositions comprising one or more peptide(s) having a stimulatory effect on the afflicted host's immune system. Specifically, the invention relates to methods comprising the use of cationic amphipathic peptides having an α-helical structure and effecting activation of macrophages when administered in a therapeutically sufficient amount. The methods of the present invention are useful for the treatment of, for example, infectious diseases or cancer.

1 Claim, 13 Drawing Sheets

FOREIGN PATENT DOCUMENTS

| | | |
|---|---|---|
| WO | WO 90/13642 | 11/1990 |
| WO | WO 91/08758 | 6/1991 |
| WO | WO 92/01462 | 2/1992 |
| WO | WO 92/13881 | 8/1992 |
| WO | WO 92/22317 | 12/1992 |
| WO | WO 93/05802 | 4/1993 |
| WO | WO 93/22348 | 11/1993 |
| WO | WO 94/02589 | 2/1994 |
| WO | WO 94/04688 (A2 A3 | 3/1994 |
| WO | WO 94/15909 | 7/1994 |
| WO | WO 94/19369 | 9/1994 |
| WO | WO 94/22467 | 10/1994 |
| WO | WO 94/28921 | 12/1994 |
| WO | WO 95/01095 | 1/1995 |

OTHER PUBLICATIONS

Curti; Physical barriers to drug delivery in tumors; Crit. Rev. Oncology/hematology; vol. 14; pp. 29–39, 1993.*

Gura; Systems for identifying new drugs are often faulty; Science; Vil. 278; p;. 1041–1042, Nov. 1993.*

Hartwell et al.; Intergrating genetic approaches into the discovery of anticancer drugs; Science; vol. 278; pp. 1064–1068, Nov. 1993.*

Mor, et al.: Isolation, amino acid sequences and synthesis of Dermaseptin . . . : Biochem.: 30: pp. 8824–8830, 1991.*

Baker, et al.: Anticancer efficacy of magainin2 . . . : Cancer Res.: 53: pp. 3052–3057, 1993.*

Mor, et al. : The NH2–terminal a–Helical Domain . . . : J. Bio. Chem: vol. 259, No. 21: pp. 1934–1939, 1994.*

Mor, et al.: The vertebrate peptide antibiotics dermaseptin . . . : J. Bio. Chem: vol. 269, No. 50:pp. 31635–31641, 1994.*

Lee, et al.: Antibacterial peptides from pig intestines: PNAC: 88: pp. 9159–9162, 1989.*

Mor, et al.: Isolation and structure of novel . . . EJB: 219: pp. 145–154, 1993.*

Jain: Barriers to drug delivery in solid tumors: Scientific American: pp. 58–65, 1994.*

Adams et al., 1990, *J. Immunol.* 144:2725–2729.

Agerberth et al., 1993, *Eur. J. Biochem.* 216:623–629.

Agerberth et al., 1995, *Proc. Natl. Acad. Sci. USA* 92:195–199.

Ahmed et al., 1975, *J. Biol Chem.* 250(21):8477–8482.

Albericio and Barany, 1985, *Int. J. Peptide Protein Res.* 26:92–97.

Alexander and Powles, 1978, *Clinics in Haematology* 7(2):275–294.

Almquist et al., 1980, *J. Med. Chem.* 23:1392–1398.

Alvarez–Bravo et al., 1994, *Biochem. J.* 302:535–538.

Amiche et al., 1993, *Biochem Biophys. Res. Comm* 191(3):983–990.

Amiche et al., 1994, *J. Biol. Chem.* 269(27):17847–17852.

Andreu et al., 1985, *Eur. J. Biochem.* 149:531–535.

Baker et al., 1993, "Anticancer efficacy of Magainin2 and Analogue Peptides," *Cancer Research* 53:3052–3057.

Bancroft et al., 1986, *J. Immunol.* 137(1):4–9.

Berge et al., 1977, *Journal of Pharmaceutical Sciences* 66(1):1–19.

Boman and Hultmark, 1987, *Ann. Rev. Microbiol.* 41:103–126.

Borenstein et al., 1991, "Antimicrobial Activity of Rabbit Leukocyte Defensins against *Treponema pallidum* subs. pallidum," *Infection and Immunity* 59(4):1359–1367.

Callaway et al., 1993, *Antimicrobial Agents and Chemotherapy* 37(8):1614–1619.

Chachoua et al., 1994, *J. Immunotherapy* 15:217–224.

Chartrel et al., 1991, *Proc. Natl. Acad. Sci. USA* 88:3862–3866.

Christensen et al., 1988, *Proc. Natl. Acad. Sci. USA* 85:5072–5076.

Conlon et al., 1992, *Peptides* 13:145–149.

Cook and McCormick, 1993, *Science* 262:1069–1071.

Couto et al., 1994, "Inhibition of Intracellular *Histoplasma capsulatum* Replication by Murine Macrophages That Produce Human Defensin," *Infection and Immunity* 62(6):2375–2378.

Cruciani et al., 1991, *Proc. Natl. Acad. Sci. USA* 88:3792–3796.

Cunha et al., 1993, *J. Immunol.* 150(5):1908–1912.

Daly et al., 1992, *Proc. Natl. Acad. Sci. USA* 89:10960–10963.

Devita, 1993, *Cancer, Principles and Practice of Oncology*, $4^{th}$ Edition. J.B. Lippincott Co., pp. 298–299, 311, 314, 2610.

Drapier et al., 1988, *Eur. J. Immunol.* 18:1587–1592.

Fishbein, 1993, "Immunotherapy of Lung Cancer," *Seminars in Oncology* 20(4):351–358.

Frommel et al., 1988, *Infection and Immunity* 56(4):843–848.

Gattoni–Celli et al., 1993, "Organ–specific metastases in melanoma: exerimental animal models," *Pigment Cell Res.* 6:381–384.

Gazit et al., 1994, *Biochemistry* 33:10681–10692.

Gibson et al., 1986, *J. Biol. Chem.* 261(12):5341–5349.

Gibson et al., 1991, *J. Biol. Chem.* 266(34):23103–23111.

Giovannini et al., 1987, *Biochem. J.* 243:113–120.

Glover et al., 1985, *Eur. J. Biochem.* 142:379–385.

Gong et al., 1990, *Immunobiol.* 182:44–55.

Gray and Haseman, 1994, *Infection and Immunity* 62(7):2732–2739.

Green et al., 1991, *Journal of Leukocyte Biology* 50:93–103.

Green et al., 1990, *J. Immunol.* 144:278–283.

Green et al., 1984, *J. Immunol. Methods* 70:257–268.

Green et al., 1981, *Proc. Natl. Acad. Sci. USA* 78(12):7764–7768.

Gunshefski et al., 1994, *Cornea* 13(3):237–242.

Guy and Beloslevic, 1995, *Clin. Exp. Immunol.* 100:440–445.

Hadden, 1993, "Immunostimulants," *Immunology Today* 14(6):275–280.

Hann et al., 1982, *J. Chem. Soc. Perkin Trans.* 1:307–314.

Hanzawa et al., 1990, *FEBS Letters* 269(2):413–420.

Hernandez et al., 1992, *Eur. J. Cell. Biol.* 59:414–424.

Hiddenmann, 1989, "What's new in malignant tumors in acquired immunodeficiency disorders?" *Path. Res. Pract.* 185:930–934.

Hino et al., 1993, *J. Dairy Sci.* 76:2213–2221.

Hino et al., 1994, *J. Dairy Sci.* 77:3426–3431.

Hirata et al., 1990, "Investigation of endotoxin binding cationic proteins from granulocytes; agglutination of erythrocytes sensitized with Re–LPS," In: *Endotoxin: Advances in Experimental Medicine and Biology* (Herman Friedman, T.W. Klein, Masayasu Nakano, and Alois Nowotny, eds.) vol. 256, pp. 287–299.

Hirata et al., 1994, *Infection and Immunity* 62(4):1421–1426.

Hoffman et al., 1983, *EMBO J.* 2(5):711–714.

Holaday et al., 1991, *J. Immunol.* 147(5):1653–1658.
Holladay and Rich, 1983, *Tetrahedron Lett.* 24(41):4401–4404.
Homma et al., 1992, *Biochem. J.* 288:281–284.
Horneff et al., 1993, *Clin. Exp. Immunol.* 91:207–213.
Hruby, 1982, *Life Sci.* 31:189–199.
Hudson et al., 1979, *Int. J. Peptide Protein Res.* 14:177–185.
Iwamoto et al., 1994, *Int. J. Peptide Protein Res.* 43:597–607.
Jain, 1994, "Barriers to Drug Delivery in Solid Tumors," *Scientific American* Jul. 1994:58–65
James and Glaven, 1989, *J. Immunol.* 143(12):4208–4212.
Janeway and Travers, 1994, "Immunobiology: The immune system in health and disease," Current Biology Ltd/Garland Publishing Inc., pp. 7:30–7:46 and 9:13–9:16.
Jennings–White and Almquist, 1982, *Tetrahedron. Lett.* 23(25):2533–2534.
Kahns and Bundgaard, 1991, *Pharmaceutical Research* 8(12):1533–1538.
Kamber et al., 1980, *Helv. Chim. Acta* 63:899–915.
Karanth et al., 1990, "Reinnervation and neuropeptides in mouse skin flaps," *J. Auton. Nerv. Syst.* 31(2):127–134.
Keppi et al., 1989, *Arch. Insect. Biochem. Physiol.* 10:229–239.
Kim et al., 1994, *FEBS Letters* 342:189–192.
Kumazawa et al., 1994, *Journal of Antibiotics* 47(10):1136–1144.
Kuzuhara et al., 1990, *J. Biochem.* 107:514–518.
Lamm, 1995, "BCG immunotherapy for transitional–cell carcinoma in situ of the bladder," *Oncology* 9(10):947–952.
Larrick et al., 1994, *Journal of Immunology* 152(1):231–240.
Larrick et al., 1991, *Biochem. Biophys. Res. Comm.* 179(1):170–175.
Larrick et al., 1993, *Antimicrobial Agents and Chemotherapy* 37(12):2534–2539.
Lee et al., 1989, "Antibacterial peptides from pig intestine: isolation of a mammalian cecropin," *Proc. Natl. Acad. Sci. USA* 86:9159–9162.
Lee et al., 1986, *Biochim. Biophys. Acta.* 862:211–219.
Lehrer et al., 1993, *Ann. Rev. Immunol.* 11:105–128.
Liew et al., 1991, *Eur. J. Immunol.* 21:3009–3014.
Liew et al., 1990, *Immunology* 69:570–573.
Liew et al., 1990, *J. Immunol.* 144:4794–4797.
Little et al., 1994, *J. Biol. Chem.* 269(3):1865–1872.
Matsuyama and Natori, 1990, *J. Biochem* 108:128–132.
Molinero et al., 1990, "Synthesis and properties of lipopeptidic surfactants," In: *Peptides* (Giralt et al., edts.), pp. 436–437.
Moncada et al., 1991, *Pharmacological Reviews* 43(2):109–142.
Monjour et al., 1984, *Annals of Tropical Medicine and Parasitology* 78(4):423–425.
Mor and Nicolas, 1994, "The $NH_2$–terminal $\alpha$–Helical Domain 1–18 of Dermaseptin Is Responsible for Antimicrobial Activity," *J. Biol. Chem.* 269(3):1934–1939.
Mor and Nicolas, 1994, "Isolation and structure of novel defensive peptides from frog skin," *Eur. J. Biochem.* 219(1–2):145–154.
Mor et al., 1994, "The vertebrate peptide antibiotics dermaseptins have overlapping structural features but target specific microorganisms," *J. Biol. Chem.* 269(50):31635–31641.
Mor et al., 1994, "Skin peptide tyrosine–tyrosine, a member of the pancreatic polypeptide family: Isolation, structure, synthesis and endocrine activity," *Proc. Natl. Acad. Sci. USA* 91:10295–10299.
Mor et al., 1994, *Biochemistry* 33:6642–6650.
Mor et al., 1991 "Isolation, amino acid sequence, and synthesis of dermaseptin, a novel antimicrobial peptide of amphibian skin," *Biochemistry* 30:8824–8830.
Morikawa et al., 1992, *Biochem. Biophys. Res. Comm* 189(1):184–190.
Morley, 1980, *Trends in Pharmacological Sciences* 1:463–468.
Munoz–Fernandez et al., 1992, *Immunology Letters* 33:35–40.
Mutter et al., 1992, *J. Am. Chem. Soc.,* 114:1463–1470.
Natori, 1987, "Hemolymph proteins participating in the defence system of *Sarcopaha peregrina*," In: Molecular Entomology, (Law, J.H., Ed.) Alan R. Liss, Inc., New York, pp. 369–378.
Nethersell, 1990, "Biological modifiers and their role in cancer therapy," *Ann. Acad. Med. Singapore,* 19(2):223–224.
Ohta et al., 1992, *Antimicrobial Agents and Chemotherapy* 36(7):1460–1465.
Okada and Natori, 1985, *Biochem J.* 229:453–458.
Ooi et al., 1987, *J. Biol. Chem.* 262:14891–14898.
Piers et al., 1993, *Gene* 134:7–13.
Podack and Konigsberg, 1984, *J. Exp. Med.* 160:695–710.
Pollock et al., 1988, *J. Biol. Chem.* 263(20):9746–9751.
Pouny et al., 1992, *Biochemistry* 31:12416–12423.
Qi et al., 1994, *Biochem. J.* 298:711–718.
Ratliff, 1992, "Role of the immune response in BCG for bladder cancer," *Eur. Urol.* 21(Suppl.2):17–21.
Richter et al., 1986, *J. Biol. Chem.* 261(8):3676–3680.
Roehrborn et al., 1995, "Lipid–based slow–release formulation of amikacin sulfate reduces foreign body–associated infections in mice," *Antimicrobial Agents and Chemotherapy* 39(8):1752–1755.
Sakick et al., 1986, *J. Immunol.* 136(2):655–661.
Sanders, 1990, *European Journal of Drug Metabolism and Pharmacokinetics* 15(2):95–102.
Sasaki and Kaiser, 1989, *J. Am. Chem. Soc.* 111:380–381.
Schenk et al., 1995, "Rapid increase in plasma tenascin–c concentration after isolated limb perfusion with high–dose tumor necrosis factor (TNF), interferon gamma (IFN$\gamma$) and melphalan for regionally advanced tumors," *Int. J. Cancer* 63:665–672.
Scher et al., 1980, *J. Exp. Med.* 152(6):1684–1698.
Schuurman et al., 1994, *Cancer Immunol. Immunother.* 39:179–184.
Shai et al., 1991, *J. Biol. Chem.* 266(33):22346–22354.
Shao and Tam, 1995, *J. Amer. Chem. Soc.* 117(14):3893–3899.
Shimoda et al., 1994, *FEBS Letters* 339:59–62.
Simmaco et al., 1994, *J. Biol. Chem.* 269(16):11956–11961.
Simmaco et al., 1993, *FEBS Letters* 324(2):159–161.
Simmaco et al., 1991, *Eur. J. Biochem.* 199:217–222.
Sims et al., 1974, *Biochemistry* 13(16):3315–3330.
Sipos et al., 1992, *Eur. J. Biochem.* 209:163–169.
Skerlavaj et al., 1990, *Infect. Immun.* 58(11):3724–3730.
Snyder and Bredt, 1992, *Sci. Am.* 266:68–77.

Song et al., 1995, "The Effect of Olfactory Bulbectomy in the Rat, Alone or in Combination with Antidepressants and Endogenous Factors, on Immune Function," *Human Psychopharmacology* 10(1):7–18.

Spatola, In: "Chemistry and Biochemistry of Amino Acids Peptides and Proteins," (B. Weinstein, Ed.), Marcel Dekker, New York, p. 267 (1983).

Spatola et al., 1986, *Life Sci.* 38:1243–1249.

Steiner et al., 1988, *Biochem. Biophys. Acta* 939:260–266.

Stone et al., 1992, *J. Chem. Soc. Perkin Trans.* 1:3173–3178.

Storici et al., 1994, *FEBS Letters* 337:303–307.

Strahlevitz et al., 1994, *Biochemistry* 33:10951–10960.

Takahashi et al., 1995, "Anti–tumor activity of tumor necrosis factor in combination with interferon–γ is not affected by prior tolerization," *Int. J. Cancer* 63:846–854.

Takx–Kohlen, 1992, "Immunomodulators. Future Prospects," *Pharm. Weekbl. [Sci.]* 14(4A):245–252.

Tatemoto, 1982, *Proc. Natl. Acad. Sci. USA* 79:2514–2518.

Tatemoto et al., 1982, *Nature* 296:659–660.

Titus et al., 1989, *J. Exp. Med.* 170:2097–2104.

Titus et al., 1985, *Parasite Immunology* 7:545–555.

Tomita et al., In: *Lactoferrin: Structure and function,* (Hutchens et al., Eds.) Plenum Press, NY, 1994, pp. 209–218.

Tossi et al., 1994, *FEBS Letters* 339:108–112.

Tossi et al., 1995, *Eur. J. Biochem.* 228:941–946.

Van der Meijden, 1991, "Non specific immunotherapy with B.C.G. in superficial bladder cancer: An overview," *In Vivo* 5:599–604.

Viljanen et al., 1988, *Infect. Immun.* 56(9):2324–2329.

Volm and Von Roenn, 1996, "Non–AIDS–defining malignancies in patients with HIV infection," *Curr. Opin. Oncol.* 8:386–391.

Vouldoukis et al., 1995, *Proc. Natl. Acad. Sci. U.S.A.* 92:7804–7808.

Vouldoukis et al., 1987, *La Presse Medicale* 16(2):76–77.

Wahlestedt and Reis, 1993, *Annu. Rev. Pharmacol. Toxicol.* 32:309–352.

Wakabayashi et al., 1985, *Nucleic Acids Res.* 13(6):1817–1828.

Wearley, 1991, *Critical Rviews in Therapeutc Drug Carrier Systems* 8(4):331–394.

Westerhoff et al., 1989, *Proc. Natl. Acad. Sci. USA* 86:6597–6601.

Williams et al., 1993, "The study of human neoplastic disease in severe combined immunodeficient mice," *Laboratory Animal Science* 43(2):139–146.

Wu et al., 1993, *Science* 262:1065–1068.

Yamada and Natori, 1994, *Biochem. J.* 298:623–628.

Yamada and Natori, 1993, *Biochem. J.* 291:275–279.

Yodoi et al., 1981, "Lymphocytes Bearing Fc Receptors for IgE: VII. Possible Participation of Phospholipase $A_2$ in the Glycosylation of IgE–Binding Factors," *J. Immunology* 127(2):476–482.

Zanetti et al., 1994, *J. Biol. Chem.* 269(11):7855–7858.

Zasloff, 1987, *Proc. Natl. Acad. Sci. USA* 84:5449–5453.

Hultmark et al., 1983, "Insect immunity. Attacins, a family of antibacterial proteins from *Hyalophora cecropia*," *The EMBO Journal* 2(4):571–576.

Klein. *Immunology.* Blackwell Scientific Publications, Inc. 1990. p. 271.

Sheth et al., 1988, "Dibutyryl cyclic AMP stimulation of a monocyte–like cell line, U937: a model for monocyte chemotaxis and Fc receptor–related functions," *Immunology* 63:483–490.

\* cited by examiner

Days post inoculation

SEQUENCE LISTING (1) GENERAL INFORMATION:

(iii) NUMBER OF SEQUENCES: 16

(2) INFORMATION FOR SEQ ID NO: 1:

(i) SEQUENCE CHARACTERISTICS:
       (A) LENGTH: 36 amino acids
       (B) TYPE: amino acid
       (C) STRANDEDNESS: single
       (D) TOPOLOGY: linear (ii) MOLECULE TYPE: None (xi) SEQUENCE DESCRIPTION: SEQ ID NO: 1:

Tyr Pro Pro Lys Pro Glu Ser Pro Gly Glu Asp Ala Ser Pro Glu Glu
 1               5                  10                  15

Met Asn Lys Tyr Leu Thr Ala Leu Arg His Tyr Ile Asn Leu Val Thr
                20                  25                  30

Arg Gln Arg Tyr
         35

(2) INFORMATION FOR SEQ ID NO: 2:

(i) SEQUENCE CHARACTERISTICS:
       (A) LENGTH: 36 amino acids
       (B) TYPE: amino acid
       (C) STRANDEDNESS: single
       (D) TOPOLOGY: linear (ii) MOLECULE TYPE: None (xi) SEQUENCE DESCRIPTION: SEQ ID NO: 2:

Tyr Pro Pro Lys Pro Glu Asn Pro Gly Glu Asp Ala Ser Pro Glu Glu
 1               5                  10                  15

Met Thr Lys Tyr Leu Thr Ala Leu Arg His Tyr Ile Asn Leu Val Thr
                20                  25                  30

Arg Gln Arg Tyr
         35

(2) INFORMATION FOR SEQ ID NO: 3:

(i) SEQUENCE CHARACTERISTICS:
       (A) LENGTH: 36 amino acids
       (B) TYPE: amino acid
       (C) STRANDEDNESS: single
       (D) TOPOLOGY: linear (ii) MOLECULE TYPE: None (xi) SEQUENCE DESCRIPTION: SEQ ID NO: 3:

Tyr Pro Ser Lys Pro Asp Asn Pro Gly Glu Asp Ala Pro Ala Glu Asp
 1               5                  10                  15

Met Ala Lys Tyr Tyr Ser Ala Leu Arg His Tyr Ile Asn Leu Ile Thr
                20                  25                  30

Arg Gln Arg Tyr
         35

(2) INFORMATION FOR SEQ ID NO: 4:

(i) SEQUENCE CHARACTERISTICS:
       (A) LENGTH: 36 amino acids
       (B) TYPE: amino acid (C) STRANDEDNESS: single
        (D) TOPOLOGY: linear (ii) MOLECULE TYPE: None (xi) SEQUENCE DESCRIPTION: SEQ ID NO: 4:

Tyr Pro Ala Lys Pro Glu Ala Pro Gly Glu Asp Ala Ser Pro Glu Glu
1               5                   10                  15

Leu Ser Arg Tyr Tyr Ala Ser Leu Arg His Tyr Leu Asn Leu Val Thr
            20                  25                  30

Arg Gln Arg Tyr
        35

(2) INFORMATION FOR SEQ ID NO: 5:

(i) SEQUENCE CHARACTERISTICS:
        (A) LENGTH: 36 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 5:

Tyr Pro Ser Lys Pro Asp Asn Pro Gly Glu Asp Ala Pro Ala Glu Asp
1               5                   10                  15

Leu Ala Arg Tyr Tyr Ser Ala Leu Arg His Tyr Ile Asn Leu Ile Thr
            20                  25                  30

Arg Gln Arg Tyr
        35

(2) INFORMATION FOR SEQ ID NO: 6:

(i) SEQUENCE CHARACTERISTICS:
        (A) LENGTH: 23 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 6:

Pro Glu Glu Met Asn Lys Tyr Leu Thr Ala Leu Arg His Tyr Ile Asn
1               5                   10                  15

Leu Val Thr Arg Gln Arg Tyr
            20

(2) INFORMATION FOR SEQ ID NO: 7:

(i) SEQUENCE CHARACTERISTICS:
        (A) LENGTH: 34 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 7:

Ala Leu Trp Lys Thr Met Leu Lys Lys Leu Gly Thr Met Ala Leu His
1               5                   10                  15

Ala Gly Lys Ala Ala Leu Gly Ala Ala Ala Asp Thr Ile Ser Gln Gly
            20                  25                  30

Thr Gln (2) INFORMATION FOR SEQ ID NO: 8:

(i) SEQUENCE CHARACTERISTICS:
        (A) LENGTH: 34 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 8:

```
Ala Leu Trp Phe Thr Met Leu Lys Lys Leu Gly Thr Met Ala Leu His
 1               5                  10                  15

Ala Gly Lys Ala Ala Leu Gly Ala Ala Ala Asn Thr Ile Ser Gln Gly
            20                  25                  30

Thr Gln
```

(2) INFORMATION FOR SEQ ID NO: 9:

(i) SEQUENCE CHARACTERISTICS:
        (A) LENGTH: 30 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 9:

```
Ala Leu Trp Lys Asn Met Leu Lys Gly Ile Gly Lys Leu Ala Gly Lys
 1               5                  10                  15

Ala Ala Leu Gly Ala Val Lys Lys Leu Val Gly Ala Glu Ser
            20                  25                  30
```

(2) INFORMATION FOR SEQ ID NO: 10:

(i) SEQUENCE CHARACTERISTICS:
        (A) LENGTH: 28 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 10:

```
Ala Leu Trp Met Thr Leu Leu Lys Lys Val Leu Lys Ala Ala Ala Lys
 1               5                  10                  15

Ala Ala Leu Asn Ala Val Leu Val Gly Ala Asn Ala
            20                  25
```

(2) INFORMATION FOR SEQ ID NO: 11:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 11:

```
Ala Leu Trp Lys Thr Met Leu Lys Lys Leu Gly Thr Met Ala Leu His
 1               5                  10                  15

Ala Gly
```

(2) INFORMATION FOR SEQ ID NO: 12:

(i) SEQUENCE CHARACTERISTICS:
  (A) LENGTH: 29 amino acids
  (B) TYPE: amino acid
  (C) STRANDEDNESS: single
  (D) TOPOLOGY: linear (ii) MOLECULE TYPE: None (xi) SEQUENCE DESCRIPTION: SEQ ID NO: 12:

Gly Leu Trp Ser Lys Ile Lys Thr Ala Gly Lys Ser Val Ala Lys Ala
1               5                   10                  15

Ala Ala Lys Ala Ala Val Lys Ala Val Thr Asn Ala Val
            20                  25

(2) INFORMATION FOR SEQ ID NO: 13:

(i) SEQUENCE CHARACTERISTICS:
    (A) LENGTH: 31 amino acids
    (B) TYPE: amino acid
    (C) STRANDEDNESS: single
    (D) TOPOLOGY: linear (ii) MOLECULE TYPE: None (xi) SEQUENCE DESCRIPTION: SEQ ID NO: 13:

Ala Met Trp Lys Asp Val Leu Lys Lys Ile Gly Thr Val Ala Leu His
1               5                   10                  15

Ala Gly Lys Ala Ala Leu Gly Ala Val Ala Asp Thr Ile Ser Gln
            20                  25                  30

(2) INFORMATION FOR SEQ ID NO: 14:

(i) SEQUENCE CHARACTERISTICS:
    (A) LENGTH: 33 amino acids
    (B) TYPE: amino acid
    (C) STRANDEDNESS: single
    (D) TOPOLOGY: linear (ii) MOLECULE TYPE: None (xi) SEQUENCE DESCRIPTION: SEQ ID NO: 14:

Gly Leu Trp Ser Lys Ile Lys Glu Val Gly Lys Glu Ala Ala Lys Ala
1               5                   10                  15

Ala Ala Lys Ala Ala Gly Lys Ala Ala Leu Gly Ala Val Ser Glu Ala
            20                  25                  30

Val (2) INFORMATION FOR SEQ ID NO: 15:

(i) SEQUENCE CHARACTERISTICS:
    (A) LENGTH: 20 amino acids
    (B) TYPE: amino acid
    (C) STRANDEDNESS: single
    (D) TOPOLOGY: linear (ii) MOLECULE TYPE: None (xi) SEQUENCE DESCRIPTION: SEQ ID NO: 15:

Glu Glu Glu Lys Arg Glu Asn Glu Asp Glu Glu Lys Gln Asp Asp Glu
1               5                   10                  15

Gln Ser Glu Met
            20

(2) INFORMATION FOR SEQ ID NO: 16:

(i) SEQUENCE CHARACTERISTICS:

```
    (A) LENGTH: 19 amino acids
    (B) TYPE: amino acid
    (C) STRANDEDNESS: single
    (D) TOPOLOGY: linear (xi) SEQUENCE DESCRIPTION: SEQ ID NO: 16:

His Ala Gly Lys Ala Ala Leu Gly Ala Ala Ala Asp Thr Ile Ser Gln
1               5                   10                  15

Gly Thr Gln
```

PEPTIDES FOR THE ACTIVATION OF THE IMMUNE SYSTEM IN HUMANS AND ANIMALS

This application is a continuation of Ser. No. 08/574,701 Dec. 19, 1995 now abandoned.

I. FIELD OF THE INVENTION

The present invention relates to therapeutic methods for the treatment and prevention of diseases via stimulation of a host's immune system. Specifically, the invention relates to methods comprising the use of cationic amphipathic peptides having an α-helical structure and which effect activation of cells of the monocyte/macrophage lineage and/or other lymphoid cells in a human or a non-human animal. The methods and compositions of the present invention are useful for the treatment and prevention of a variety of diseases, including, but not limited to, infectious diseases and cancer.

II. BACKGROUND OF THE INVENTION

In the last few years, a large number of peptides have been identified sharing the characteristic of having an antimicrobial activity. One particular class comprises cationic amphipathic peptides which tend to have an α-helical structure, especially in a low-polarity environment.

It is well-established that such antimicrobial peptides function through a lytic/ionophoric mechanism. Lehrer et al., 1993, *Ann. Rev. Immunol.* 11:105–128; Christensen et al., 1988, *Proc. Natl. Acad. Sci. USA* 85:5072–5076; Cruciani et al., 1991, *Proc. Natl. Acad. Sci. USA* 88:3792–3796; Viljanen et al., 1988, *Infect. Immun.* 56:3724–3730; Skerlavaj et al., 1990, *Infect. Immun.* 58:3724–3730; Okada and Natori, 1985, *Biochem J.* 229:453–458; Matsuyama and Natori, 1990, *J. Biochem.* 108:128–132; Keppi et al., 1989, *Arch. Insect. Biochem. Physiol.* 10:229–239; Ohta et al., 1992, *Agents Chemother.* 36:1460–1465. A common theme among these "lytic" peptides is their permeabilizing effect by "punching holes" into bacterial cytoplasmic membranes. The cationic, amphipathic structure of these peptides appears to facilitate the formation of hydrophilic ion channels in a lipid bilayer whereby the polar amino acids are positioned on one surface of the helix, and the apolar amino acids are positioned on the opposite side of the helix. Lee et al., 1986, *Biochim. Biophys. Acta* 862:211–219.

One family of these peptides with known antimicrobial properties, namely the dermaseptins, has been isolated from the skin of the tree frog, *Phyllomedusa sauvagei*. Others of this family have been isolated in later stages from *Ph. bicolor.* Mor et al., 1991, *Biochemistry* 30:8824; Mor et al., 1994, *Biochemistry* 33:6642; Mor et al., 1994, *Eur. J. Biochem.* 219:145. Each member of this family is a cationic amphipathic peptide with an α-helical structure and is endowed with lytic activity against a wide array of pathogenic microorganisms in vitro.

Another peptide family with similar properties comes from well known, ubiquitous neuropeptides with functional and structural characteristics similar to the dermaseptins. Neuropeptide Y (NPY) (Tatemoto et al., 1982, *Nature* 296:659–660) and peptide YY (PYY) (Tatemoto, 1982, *Proc. Natl. Acad. Sci. USA* 79:2514–24518) two 36-residue peptides, are members of the pancreatic peptide (PP) family, found in the brain and in the lining of the gastrointestinal tract, respectively. They are involved in a variety of important regulatory functions and possess common features of tertiary structure, the so-called PP-fold. Glover et al., 1985, *Eur. J. Biochem.* 142:379–3385. The PP-fold, as characterized by X-ray diffraction analysis of crystals, consists of two antiparallel helices: an N-terminal polyproline helix and a long amphipathic α-helix. To date, all PP family members were reported to induce their various biological effects by activating specific membrane bound receptors. Wahlestedt and Reis, 1993, *Annu. Rev. Pharmacol. Toxicol.* 32:309–352.

Other cationic amphipathic peptides having antimicrobial activity can be found, for example, among many other places, in the PCT Applications WO94/19369, published Sep. 1, 1994; U.S. Pat. No. 5,348,942.

Notably, the Minimal Inhibitory Concentration (MIC) for such peptides in order to exhibit lyticlionophoric, antimicrobial activity has been reported to be in the micromolar range. For example, as it is specifically reported in the U.S. Pat. No. 5,221,664, the MIC value for the antimicrobial peptide "B13-33" in order to exhibit antibacterial activity against *Staphylococcus aureus* is at least four (4) micromolar, the MIC for "Magainin II" against *Pseudonomas aeruginosa* is as high as 256 micromolar. The effective concentrations can only be lowered by the addition of synergistic acting toxic cations, for example silver nitrate (see, U.S. Pat. No. 5,221,664).

Many infectious agents such as *E. coli* and *S. aureus* are pathogenic by virtue of their ability to proliferate in the circulation and in tissue space. These pathogens do not invade host organism cells and hence do not replicate as intracellular agents. As such, these types of pathogens are amenable to eradication by antibiotics, including peptide antimicrobials, that have no ability to enter mammalian cells. In contrast, certain pathogens such as *M. tuberculosis, M. avium* and *M. intracellulare*, and Leishmania sp. propagate primarily inside host organism cells, and in particular circulating cells of the immune system such as macrophages. These organisms are not accessible to the direct lytic effects of antimicrobial agents such as antimicrobial peptides that do not readily penetrate the infected mammalian cell.

The present invention is concerned with a novel use of cationic amphipathic peptides for therapeutic methods. As will be described hereinbelow, such peptides are useful for new methods for stimulating a host's immune system by effecting the activation of cells of the monocyte/macrophage lineage and/or other lymphoid cells. These activated cells then contribute to the elimination of the pathogen. The amount of such peptides required for the methods of the present invention is significantly lower compared to the amount necessary for the lysis of bacterial cells.

III. SUMMARY OF THE INVENTION

The present invention is directed to methods for treating and/or preventing diseases said method comprising the administration to a host an active peptide having a stimulatory effect on the host's immune system. Specifically, the cationic, amphipathic α-helical peptides useful in the invention are pharmaceutically active by effecting activation of cells of the monocyte/macrophage lineage and/or other lymphoid cells in a treated human or non-human animal. Preferably, the peptides used have a length of about eight (8) to about fifty (50) amino acid residues.

In one embodiment, the peptide of the invention may have one of the following sequences:

$(X)_a(Z)_n(X)_b$ and pharmaceutically acceptable salts thereof, wherein:

Z is selected from the primary sequences A-B-C-D, D-A-B-C, D-C-B-A, C-B-A-D, whereby each Z group within one peptide may be identical or different, and whereby $Z_n$ is positively charged and contains about 20% to about 50% hydrophilic amino acid residues, preferably about 25% to about 45% hydrophilic amino acid residues;

A is a hydrophobic or a small amino acid residue, whereby at least one A of two adjacent Z groups is hydrophobic;

C is a hydrophilic or a small amino acid residue, preferably a basic or neutral hydrophilic amino acid residue, whereby at least one C of two adjacent Z groups is basic hydrophilic;

B and D can be any amino acid residue, whereby B and D may be the same or different;

A, B, C, and D of each group may be the same or may be different in some or all of the groups;

$(X)_a$ and $(X)_b$ are amino acid assemblies of any length and composition which may not significantly contribute to the α-helical structure;

$n \geq 2$ and $a,b \geq 0$, with the proviso that $8 \leq a+b+4n \leq 50$.

In another embodiment, the peptide of the invention may have one of the following sequences:

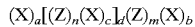

and pharmaceutically acceptable salts thereof, wherein:

Z is selected from the primary sequences A-B-C-D, D-A-B-C, D-C-B-A, C-B-A-D, whereby each Z group within one peptide may be identical or different, and whereby $Z_n$ and $Z_m$ are positively charged and contain about 20% to about 50% hydrophilic amino acid residues, preferably about 25% to about 45% hydrophilic amino acid residues;

A is a hydrophobic or a small amino acid residue, whereby at least one A of two adjacent Z groups is hydrophobic;

C is a hydrophilic or a small amino acid residue, preferably a basic or neutral hydrophilic amino acid residue, whereby at least one C of two adjacent Z groups is basic hydrophilic;

B and D can be any amino acid residue, whereby B and D may be the same or different;

A, B, C, and D of each group may be the same or may be different in some or all of the groups;

$(X)_a$, $(X)_b$ and $(X)_c$ are amino acid assemblies of any length and composition which may not significantly contribute to the α-helical structure;

$n,m,d \geq 1$ and $a,b,c \geq 0$, with the proviso that $8 \leq a+b+d(c+4n)+4m \leq 50$.

According to the present invention, the peptides are administered to a host in an amount effective to activate cells of the monocytes/macrophage lineage and/or other lymphoid cells of said host. Preferably, peptides of the invention are administered in an amount effective to achieve a serum peptide level of about $10^{-9}$ M to about $10^{-5}$ M, typically the amount administered will be to achieve a serum peptide level of about $10^{-9}$ M to about $10^{-6}$ M. Such serum levels may be achieved by the administration of about 0.0005 to about 5.0 mg/kg body weight, typically about 0.0005 to about 0.5 mg/kg body weight. In some embodiments, the peptides are administered in combination with other compounds, including, but not limited to, antibiotics or protease inhibitors. The methods of the present invention are useful for the treatment of a variety of diseases including, but not limited to, infectious diseases and cancer.

IV. BRIEF DESCRIPTION OF THE FIGURES

FIG. 1 depicts the membrane permeation effect of SPYY (filled circles), $SPYY_{14-36}$ (squares) and Cecropin B1 (empty circles) and acidic peptide (triangles).

FIGS. 2A and 2B depict the anti-leishmaniasis effect of SPYY in vivo. Treated and control mice are represented with stars and circles, respectively. Arrows indicate treatment onset. FIG. 2A: Direct examination of the cutaneous lesion. Plotted values represent the mean of the lesion score, standard error deviations were ±15%. FIG. 2B: The level of parasites was assessed by periodic aspiration. Standard error deviations were ±5%.

FIGS. 3A and 3B depict the cure of murine-cutaneous leishmaniasis by SPYY. FIG 3A: Mice infected with *Leishmania major* parasites displaying a cutaneous lesion at the proximal portion of the tail 4 weeks after inoculation. FIG. 3B: Complete skin reconstitution 8 weeks after treatment onset.

FIGS. 4A, 4B and 4C depict the effect of SPYY on cultured macrophages as visualized after Giemsa staining. FIG. 4A: Macrophages infected with *Leishmania major* parasites, before treatment or after 48 hours treatment with the acidic peptide (100 μg/ml). FIG. 4B: Infected macrophages, after 48 hours treatment with SPYY (100 μg/ml). FIG. 4C: Control macrophages (non-infected) after 48 hours treatment with SPYY (100 μg/ml).

FIGS. 5A and 5B depict the dose-dependent kinetics of the leishmanicidal effect. Each point represents the mean of 2 independent experiments performed in duplicates. Standard deviations were ≦10%.

FIGS. 6A, 6B and 6C depict the elimination of intracellular amastigotes. FIG. 6A: Healthy macrophages after 48 hours incubation with DS (100 μg/ml). FIG. 6B: Non-treated infected macrophages. FIG. 6C: Infected macrophages after 48 hours incubation with DS (100 μg/ml).

FIGS. 7A, 7B and 7C depict the immuno-localization of DS on promastigotes and macrophages. FIG. 7A: Promastigotes ($1 \times 10^5$ parasites/ml) were exposed for 5 minutes to DS (10 μg/ml) in RPMI 1640 culture medium at 26° C. and revealed by indirect immuno-fluorescence. FIGS. 7B and 7C: Visualization and quantitative analysis of immunoreactive cells, respectively. Immunoreactivity was revealed using the immunoperoxidase method (see, infra) and a subsequent Mayer hemalun staining.

Figures 10A, 10B, 10C:
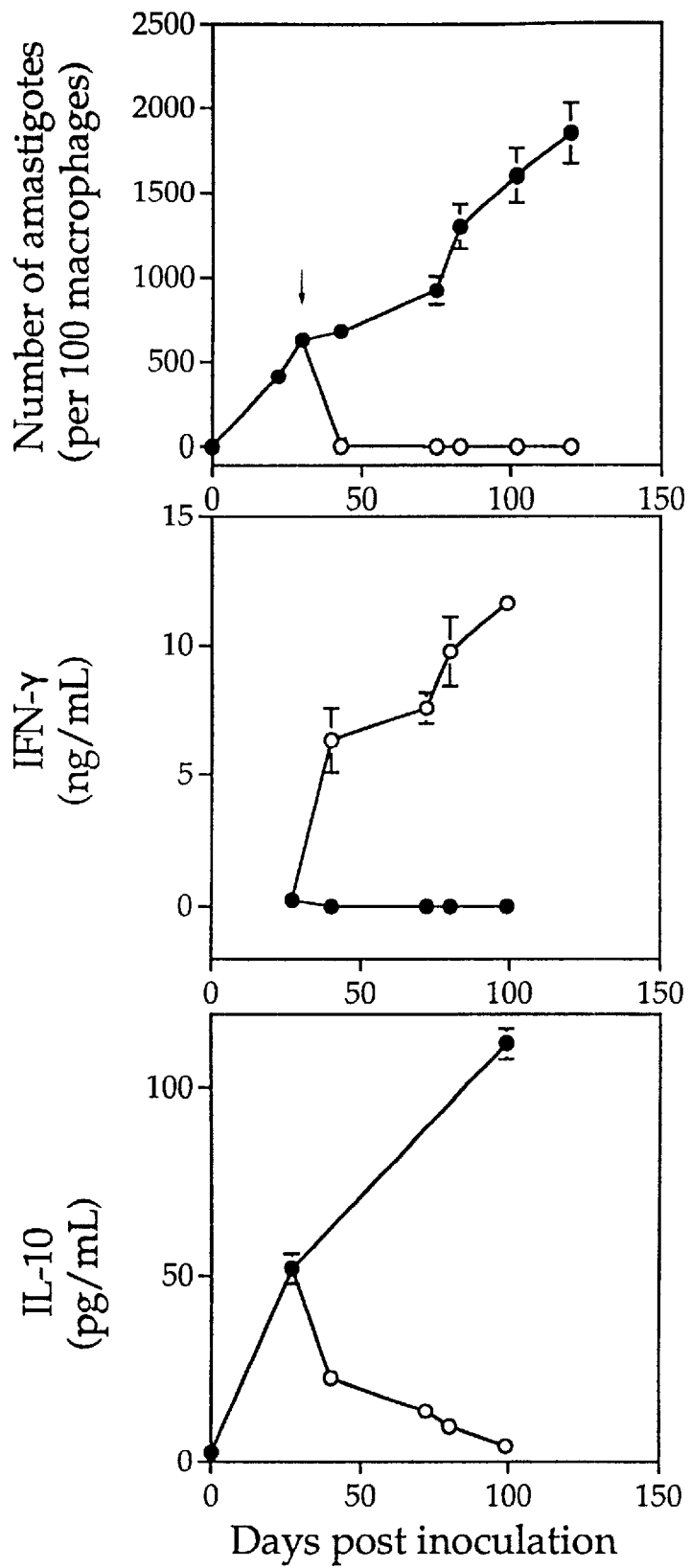

FIGS. 10A, 10B and 10C depict the cure of leishmaniasis in Balb/c mice by treatment with SPYY. FIG. 10A shows the number of parasites, determined by a count of infected macrophages on Giemsa stained smears under light microscope. FIG. 10B depicts the serum concentrations of IFN-γ, FIG. 10C depicts the serum concentration of IL-10 of treated and control mice, which are represented with empty and filled circles, respectively. The arrow indicates the treatment onset.

Figures 11A, 11B, 11C:
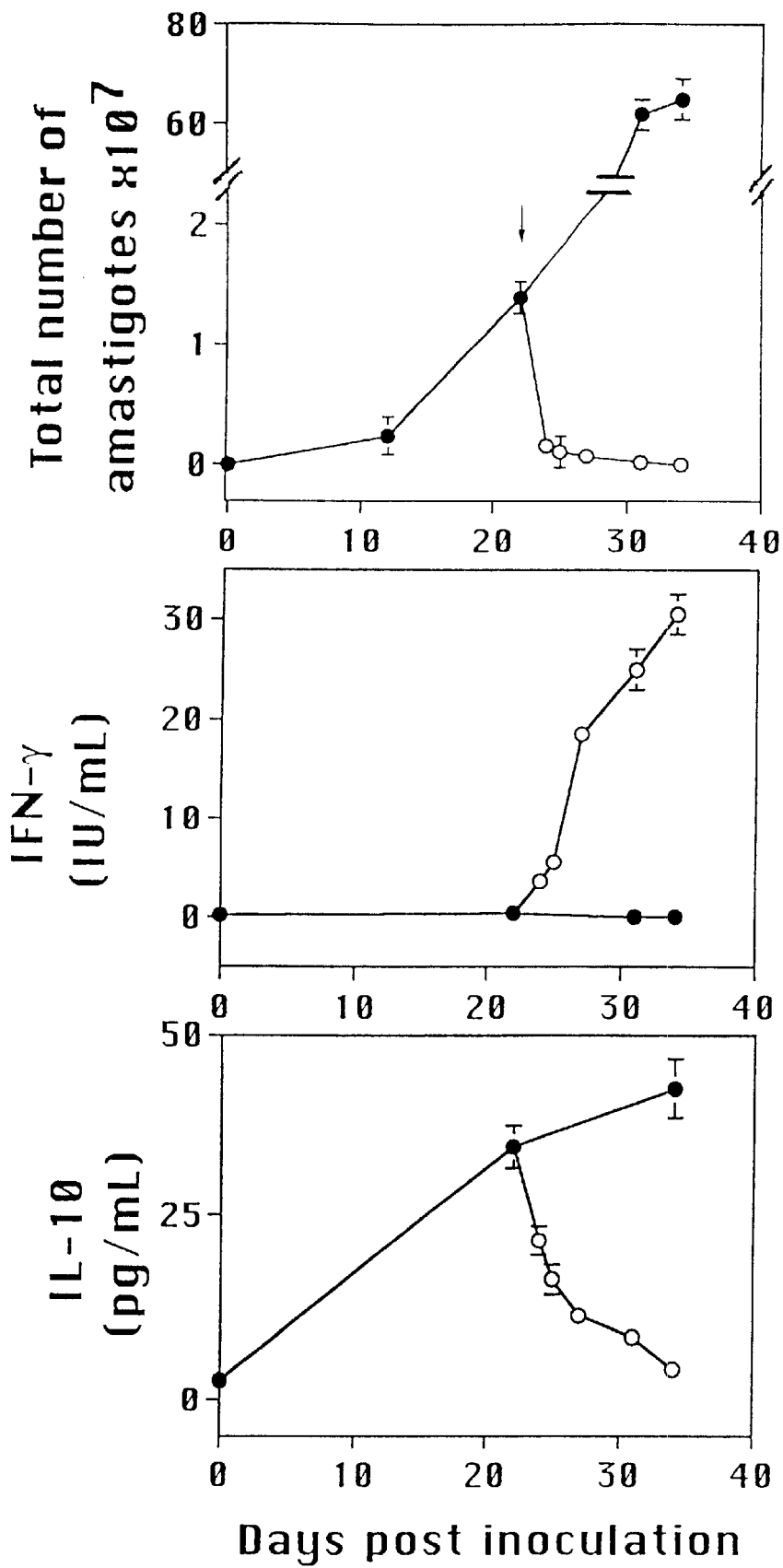

FIGS. 11A, 11B and 11C depict the cure of leishmaniasis in SCID mice with SPYY. FIG. 11A shows the amastigotes number which was estimated using a limiting dilution assay. FIGS. 11B and 11C show IFN-γ and IL-10 serum concentrations, respectively. Treated and control mice are represented with the empty and filled circles, respectively. The arrow indicates the treatment onset.

Figure 12A:
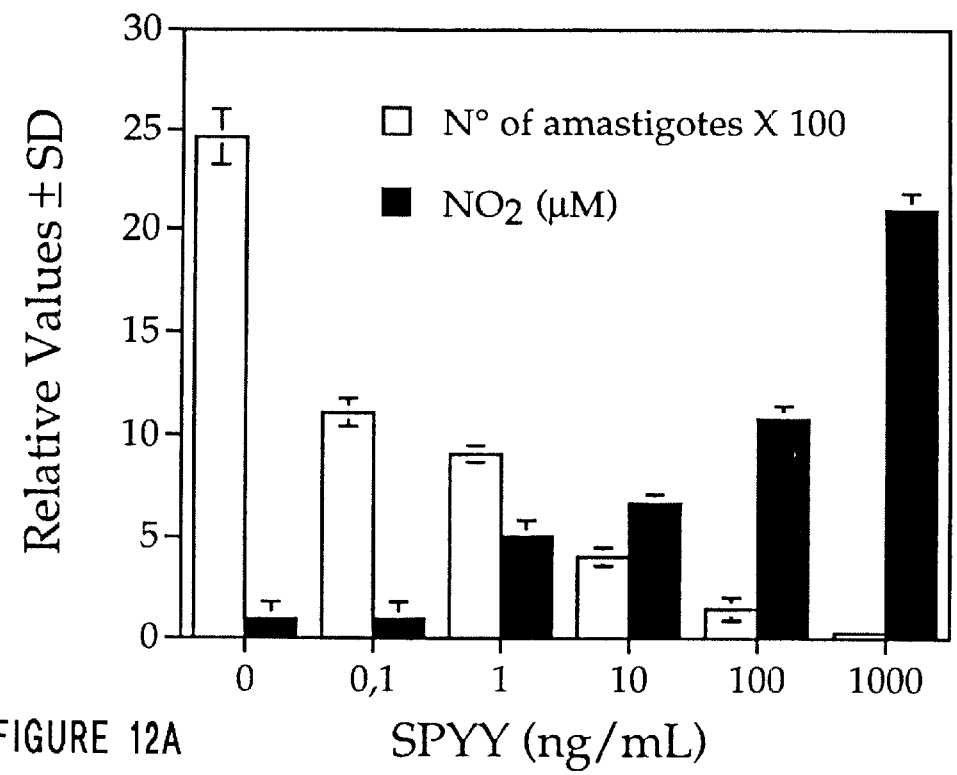
Figure 12B:
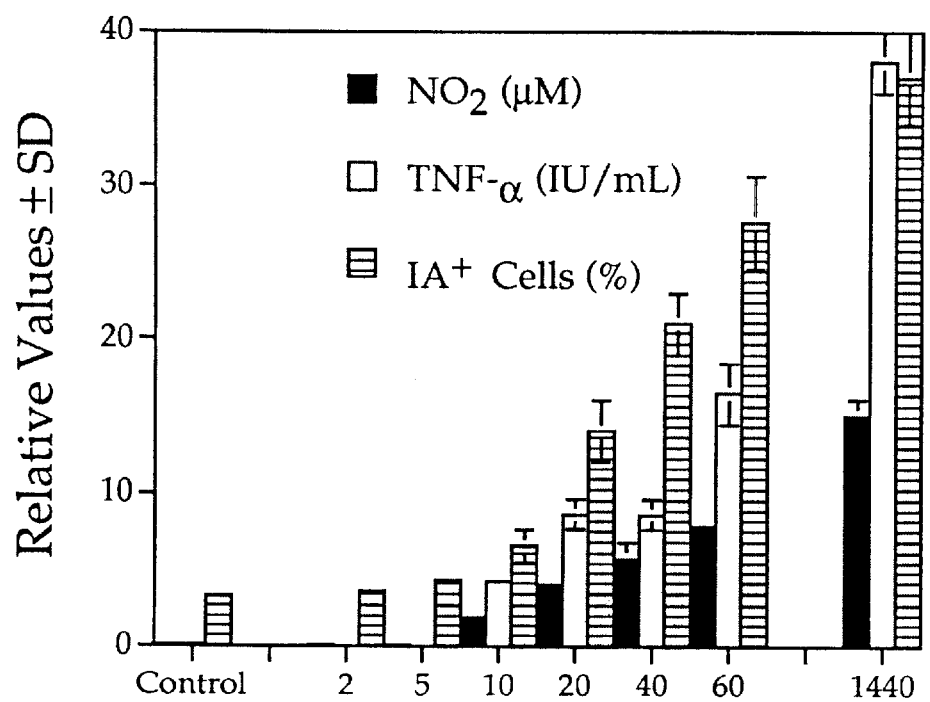

FIGS. 12A and 12B depict the direct activation of macrophages by SPYY. FIG. 12A: Macrophages were incubated with various SPYY concentrations and then exposed to infections; resistance to infection was determined by counting intracellular amastigotes over a total of 500 macrophages in 20 random microscopic fields and by determination of nitrate concentrations using the Greiss reagent. Values are from 2 independent experiments. FIG. 12B shows the time course response of SPYY-treated macrophages by measurement of $NO_2$, TNF-α concentrations, and measurement of I-A cell surface expression. Values shown are from two independent experiments.

Figure 13:
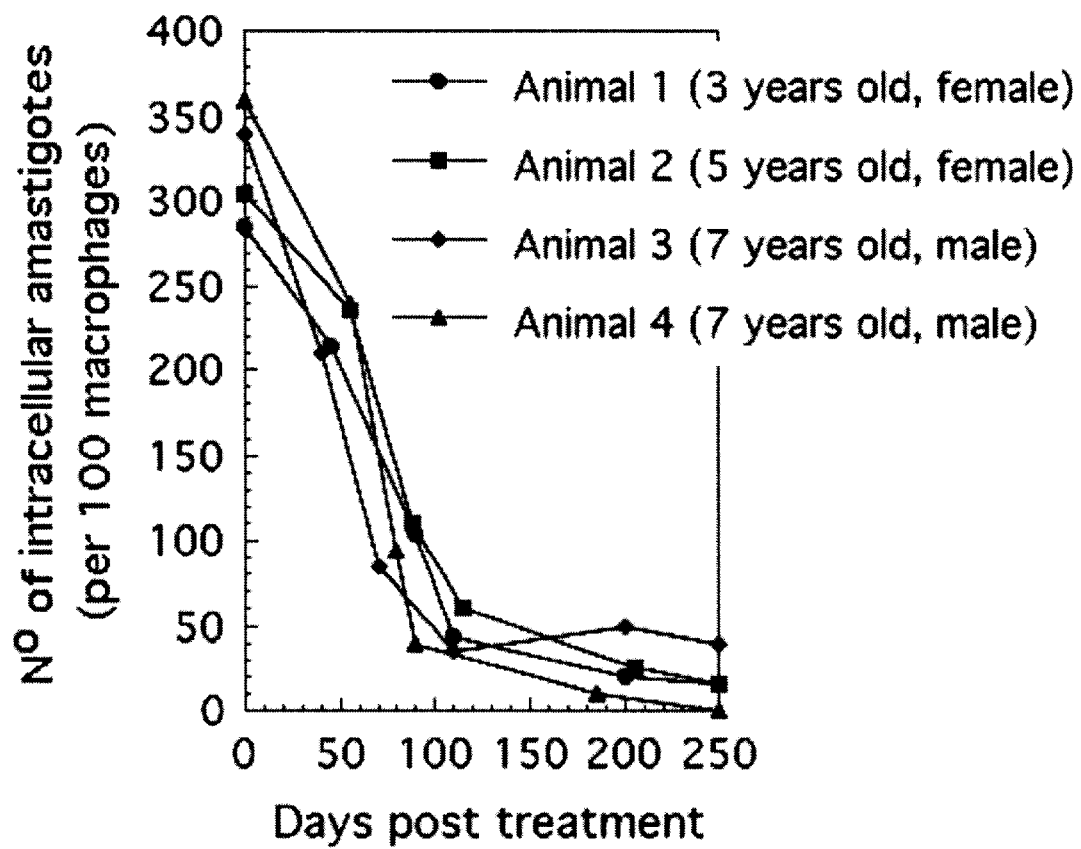

FIG. 13 depicts the reduction of the number of amastigote-infected macrophages in leishmania-infected dogs after treatment with dermaseptin DS s3 $CONH_2$.

V. DETAILED DESCRIPTION OF THE INVENTION

The present invention relates to the novel use of a herein specified class of peptides, some of which are known for their antimicrobial activity in vitro, for therapeutic methods for the treatment and the prevention of a variety of diseases, including, but not limited to, infectious diseases and cancer Specifically, the present invention is based on the inventors' unexpected discovery that a certain class of peptides, which previously have been shown to have antimicrobial activity, stimulates the host's immune system by effecting activation of cells of the monocyte/macrophage lineage and/or other lymphoid cells.

Previously, therapeutic approaches to activate or enhance the immune system have been to administer classic immune system activators such as γ-interferon, TNF-α, and certain interleukins. The problem with these therapeutic approaches, however, are well known: prolonged treatments and cytokine toxicity.

The therapeutic methods provided by the present invention will overcome many of these disadvantages. The active peptides useful for the novel therapeutic methods described hereinbelow effect, for example, macrophage activation within minutes, which contrasts with activation of macrophages obtained via traditional cytokines which can be on the order of five (5) hours.

Moreover, the use of these peptides for the novel methods of the present invention provides further significant improvements over their previously described use. Specifically, prior to the subject invention, due to their ability to lyse micro-organisms in vitro, it has been suggested that such peptides could be useful for the treatment of infections. See, for example, PCT Application WO94/19369, published Sep. 1, 1994; U.S. Pat. Nos. 5,348,942; and 5,221,664. The MIC value for lytic activity of such peptides, however, has been reported to be in the range of one (1) micromolar or above. See, PCT Application WO94/19369, published Sep. 1, 1994; U.S. Pat. No. 5,221,664; and Section II., supra. As the experimental examples disclosed hereinbelow will demonstrate, activation of, for example, macrophages is effected at a significantly lower peptide concentration, i.e., in the range between $10^{-9}$ M and $10^{-6}$ M.

A. Definitions

As used herein, an "α-helical peptide" is a peptide having at least one α-helical turn in a low-polarity environment. Such an "α-helical peptide" may, of course, also comprise non-α-helical portions.

As used herein, an "amphipathic peptide" is a peptide having both hydrophobic and hydrophilic amino acid residues displayed on opposite faces of the peptide structure.

As used herein, an "analogue" or "derivative" is a compound, e.g., a peptide, having more than about 70% sequence but less than 100% sequence similarity with a given compound, e.g., a peptide. Such "analogues" or "derivatives" may be comprised of non-naturally occurring amino acid residues, including by way of example and not limitation, homoarginine, ornithine and norvaline, as well as naturally occurring amino acid residues. Such "analogues" or "derivatives" may also be composed of one or a plurality of D-amino acid residues, and may contain non-peptide interlinkages between two or more amino acid residues.

As used herein, a "cationic peptide" is a peptide which has a preponderance of positively charged amino acids resulting in an isoelectric point (pI) of greater than 7.0. Such positively charged amino acid residues include, but are not limited to, arginine, lysine, histidine, homoarginine and ornithine.

As used herein, an "interhelical domain" is an assembly of amino acid residues of any length and composition which may not contribute to the α-helical structure. It links together two α-helical domains within one peptide. An interhelical domain defines the curvature of a peptide comprising more than one α-helical domain.

As used herein, a "curvature" defines the tertiary structure of a peptide. Within an α-helical domain, the curvature is a result of, for example, steric, electrostatic, etc. interactions between the side chains of the amino acid residues in the sequence. Further, the length and amino acid composition of interhelical domains contributes to the characteristic curvature of each peptide.

As used herein, "pharmaceutically effective amount" is the amount of a compound in which said compound, i.e., an active peptide used in the invention, effects the desired immunomodulating activity, but does not have toxic side effects to an extent that limits clinical use of the compound.

The amino acid notations used herein for genetically encoded amino acids are conventional and are as follows:

| Amino Acid | One-Letter Symbol | Three-Letter Symbol |
|---|---|---|
| Alanine | A | Ala |
| Arginine | R | Arg |
| Asparagine | N | Asn |
| Aspartic acid | D | Asp |
| Cysteine | C | Cys |
| Glutamine | Q | Gln |
| Glutamic acid | E | Glu |
| Glycine | G | Gly |
| Histidine | H | His |
| Isoleucine | I | Ile |
| Leucine | L | Leu |
| Lysine | K | Lys |
| Methionine | M | Met |

-continued

| Amino Acid | One-Letter Symbol | Three-Letter Symbol |
| --- | --- | --- |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |

The peptides used for the methods of the present invention are partially defined in terms of amino acid residues of designated classes. Amino acid residues can be generally subclassified into major subclasses as follows:

1. Hydrophilic:

Acidic. The residue has a negative charge due to loss of a $H^+$ ion at physiological pH and the residue is attracted by aqueous solution so as to seek the surface positions in the conformation of a peptide in which it is contained when the peptide is in aqueous medium at physiological pH. Naturally occurring acidic amino acid residues include aspartic acid and glutamic acid.

Basic. The residue has a positive charge due to association with a $H^+$ ion at physiological pH and the residue is attracted by aqueous solution so as to seek the surface positions in the conformation of a peptide in which it is contained when the peptide is in aqueous medium at physiological pH. Naturally occurring basic amino acid residues include the non-cyclic amino acids arginine, lysine, ornithine, diamino-butyric acid, and the cyclic amino acid histidine.

Polar. The residues are not charged at a physiological pH, but the residue is not sufficiently repelled by aqueous solutions so that it would seek inner positions in the conformation of a peptide in which it is contained when the peptide is in aqueous medium. Naturally occurring polar amino acid residues include asparagine, glutamine, serine threonine, and cysteine in the reduced stage such as the SH-form.

Cysteine residues have the capacity to form disulfide bonds, which are critical for the secondary structure of the peptides of the invention. However, when the —SH group is free, cysteine is-quite hydrophilic, as indicated above.

2. Hydrophobic:

The residues are not charged at physiological pH and the residue is repelled by aqueous solution so as to seek the inner positions in the conformation of a peptide in which it is contained when the peptide is in aqueous medium. Naturally occurring hydrophobic amino acid residues include tyrosine, valine, isoleucine, leucine, methionine, phenylalanine, tryptophan, and cysteine (when in the oxidized stages such as the S—S form).

3. Small:

This description also characterizes certain amino acids as "small" since their side chains are not sufficiently large to confer hydrophobicity. "Small" amino acids are those with four carbons or less when at least one polar group is on the side chain and three carbons or less when not. Naturally occurring small amino acid residues include glycine, serine, alanine, threonine. Serine and threonine are also included in the hydrophilic/polar group (see, supra). Furthermore, the gene-encoded secondary imino acid proline is included in the group designated as small amino acid residues, although it is known to affect the secondary conformation of peptide chains.

It is understood, of course, that in a statistical collection of individual amino acid residues in a structure such as a peptide, some of the peptides will be charged, and some not, and there will be an attraction for or repulsion from an aqueous medium to a greater or lesser extent. To fit the definition of "charged" an excess of residues in the individual molecule is charged at physiological pH. The degree of attraction or repulsion required for classification as polar or nonpolar is arbitrary and, therefore, amino acids specifically contemplated by the invention have been classified as one or the other. Most amino acids not specifically named can be classified on the basis of known behavior.

Certain commonly encountered amino acids, which are not encoded by the genetic code, include, but are not limited to, for example, beta-alanine (beta-Ala), or other omega-amino acids, such as 3-aminopropionic, 2,3-diaminopropionic (2,3-diap), 4-aminobutyric and so forth, alpha-aminisobutyric acid (Aib), sarcosine (Sar), ornithine (Orn), citrulline (Cit), t-butylalanine (t-BuA), t-butylglycine (t-BuG), N-methylisoleucine (N-MeIle), phenylglycine (Phg), and cyclohexylalanine (Cha), norleucine (Nle), 2-naphthylalanine (2-Nal); 1,2,3,4-tetrahydroisoquinoline-3-carboxylic acid (Tic); β-2-thienylalanine (Thi); methionine sulfoxide (MSO); and homoarginine (Har); Acetyl Lys; 2,4-diaminobutyric acid (DBU); p-aminophenylalanine; and homoserine (HSE). These also fall conveniently into particular categories.

Based on the above definitions,

Sar, beta-Ala, 3-aminopropionic, 4-aminobutyric and Aib are small;

Orn, 2,3-diaP, DBU, p-aminophenylalanine, and Har are basic;

t-BuA, c-BuG, N-MeIle, Nle, Mvl, Cha, Phg, 2-Nal, Thi and Tic are hydrophobic;

Cit, Acetyl Lys, Hse, and MSO are polar.

The various omega-amino acids are classified according to size as small (beta-Ala and 3-aminopropionic) and/or as hydrophobic (all others).

Other amino acid substitutions of those encoded in the gene can also be included in the peptide compounds within the scope of the invention and can be classified within this general scheme according to their structure.

In all of the peptides of the invention, one or more amino linkages (—CO—NH—) may optionally be replaced with another linkage which is an isostere such as —CH$_2$NH—, —CH$_2$S—, —CH$_2$CH$_2$, —CH—CH— (cis and trans), —COCH$_2$—, —CH(OH)CH$_2$— and —CH$_2$SO—. This replacement can be made by methods known in the art. The following references describe preparation of peptide analogues which include these alternative-linking moieties. Spatola, 1983, Vega Data 1, Issue 3, "Peptide Backbone Modifications"; Spatola, in: "Chemistry and Biochemistry of Amino Acids Peptides and Proteins," (B. Weinstein, ed.), Marcel Dekker, New York, p. 267 (1983); Morley, 1980, *Trends Pharm. Sci.* 1:463–468; Hudson et al., 1979, *Int. J. Prot. Res.* 14:177–185 (—CH$_2$NH—, —CH$_2$CH$_2$—); Spatola et al., 1986, *Life Sci.* 38:1243–1249 (—CH$_2$—S); Hann, 1982, *J. Chem. Soc. Perkin Trans. I.* 1:307–314 (—CH—CH—, cis and trans); Almquist et al., 1980, *J. Med. Chem.* 23:1392–1398 (—COCH$_2$—); Jennings-White et al., *Tetrahedron. Lett.* 23:2533 (—COCH$_2$—); European Patent Application EP 45665 (1982) (—CH(OH)CH$_2$—); Holladay et al., 1983, *Tetrahedron Lett.* 24:4401–4404 (—C(OH)CH$_2$—); and Hruby, 1982, *Life Sci.* 31:189–199 (—CH$_2$—S—).

B. The Peptides and the Compositions

Generally, the peptides useful in the present invention are peptides having an immunomodulating activity. More specifically, the peptides useful for the compositions and methods of the present invention effect activation of cells of the monocyte/macrophage lineage and/or other lymphoid cells when administered to a human or non-human animal in a pharmaceutically effective amount. Such activating effect on cells of the monocyte/macrophage lineage and/or other lymphoid cells can be determined using a variety of in vivo and/or in vitro assays which are well-known in the art. A preferred assay for measuring, for example, the macrophage stimulating activity of the peptides useful for the methods of the present invention is a TNF-$\alpha$ secretion assay. Such assay is described, among other places, in Horneff et al., 1993, *Clin. Exp. Immunol.* 91:207–213; Chachuoa et al., 1994, *J. Immunotherapy* 15:217–224; Schuurman et al., 1994, *Cancer Immunol. Immunother.* 39:179–184. But again, as the skilled artisan will know, many other assays may be employed.

The peptides useful for the methods of the present invention comprise cationic amphipathic peptides at times presented in a random conformation which tend to increase $\alpha$-helical content of the peptide, especially in low-polarity environments, for example in the presence of lipid bilayers. Other factors can also influence the $\alpha$-helical content of the peptide, such as the type of lipid, ionic strength, pH of the solution, etc. Mor et al., 1994, *Biochemistry* 33:6642–6650. In a hydrophobic environment, such as on the membrane, where such cationic amphipathic peptides tend to acquire an $\alpha$-helical structure, they also tend to self-associate via an interaction of the hydrophobic faces of the peptides. Thereby they may assume an ordered structure such as $\alpha$-helical bundles in a parallel (head to head) or antiparallel (head to tail) fashion, generating an aggregate with a hydrophilic center and a hydrophobic outside. In general, such peptides comprise at least eight (8) amino acid residues, and in many cases have at least twenty (20) amino acid residues. Typically, such peptides have up to about fifty (50) or less amino acid residues.

In most cases, the peptide is a basic (positively charged) peptide having at least eight (8) amino acid residues, wherein at least one domain of the peptide includes about 20% to about 50% hydrophilic amino acid residues. Preferably, about 25% to about 45% of the amino acid residues in this domain are hydrophilic.

In respect to the three-dimensional structure, the amphipathic $\alpha$-helix is divided into four sectors—the hydrophobic sector, the hydrophilic sector and two helical junctions, assuming the following order: junction sector—hydrophilic sector—junction sector—hydrophobic sector. It is known, however, that these sectors are not defined by the primary sequence but by their location in the secondary structure. The hydrophobic sector is usually composed of a group of hydrophobic amino acids residues, which is predominantly located on the lipid interacting, nonpolar face of the helix. Predominant amino acids of this sector are leucine, phenylalanine, valine and isoleucine. The hydrophilic sector is usually composed of a group of hydrophilic amino acid residues (including charged and polar residues), which is primarily located on the polar face of the helix. In the cationic peptide, the predominant naturally occurring amino acid residues are arginine, lysine, histidine, serine and threonine. Acidic amino acids such as aspartic acid and glutamic acid, as well as polar amino acids such as asparagine and glutamine can also be present. The helix junctions provide a motif for peptide-peptide recognition as well as for the assembly of peptide monomers into larger ordered aggregates. In the $\alpha$-helical junction sectors, in general all hydrophobic and hydrophilic amino acid residues can be found, though glycine and proline are most typical in this region.

The amino acid sequence of amphipathic $\alpha$-helical peptides tends to have a strong periodic distribution of hydrophobic amino acid residues along a chain with about three to four amino acid residue repeats. The amino acid residues between such repeats comprising single $\alpha$-helical domains may assume a curved structure, which is an intrinsic and characteristic property of each amphipathic $\alpha$-helix.

The three-dimensional $\alpha$-helical structure defined by the relationship of amino acid residues within each sector of the $\alpha$-helical domain is presided by the primary sequence of each peptide. In the following, preferred primary sequences assuming $\alpha$-helical domains will be described.

In a first preferred embodiment, the hydrophobic amino acid residues are arranged in groups of two (2) adjacent amino acid residues. Each group of two (2) adjacent hydrophobic amino acid residues is spaced from another group of two (2) adjacent hydrophobic amino acid residues by at least one (1), but typically no more than five (5) amino acid residues (herein referred to as "spacer" residues). Preferably, each group of spacer residues is comprised by at least one (1) amino acid residue, but typically by no greater than five (5) amino acid residues, wherein at least one is hydrophilic. More preferably, the group of spacer residues comprises at least one basic or neutral hydrophilic amino acid residue, as the net charge of the peptide is positive.

In a second preferred embodiment, the peptide comprises a chain of at least-two (2) groups of amino acid residues, wherein each group consists of four (4) amino acid residues. Two of the four (4) amino acid residues in each group are hydrophobic amino acid residues, and at least one (1) of the four (4) amino acid residues in each group is hydrophilic preferably a basic or a neutral hydrophilic amino acid residue, as the net charge of the peptide is positive. The forth amino acid residue can, generally, be any amino acid.

In a third preferred embodiment, the peptide comprises a chain of at least two (2) groups of amino acid residues wherein each group consists of four (4) amino acid residues. Every group contains at least one hydrophobic or small amino acid residue and at least one hydrophilic or small amino acid residue. Within two adjacent groups, at least one amino acid residue is hydrophobic, and at least one amino acid residue is hydrophilic. The hydrophilic amino acid residue, in typical cases, is a basic or a neutral hydrophilic amino acid residue, as the net charge of the peptide is positive. Each of the hydrophobic or small amino acid residues and each of the hydrophilic or small amino acid residues are spaced by one (1) spacer amino acid residue. The spacer amino acid residues can, generally, be any amino acid. Two groups of four amino acid residues may be separated by a number of spacer amino acids $\geq 1$, provided that the spacing between such groups and the charge on the amino acid residues does not change the characteristics of the peptide chain which provide amphipathicity and a positive charge and do not adversely affect the folding characteristics of the chain to that which is significantly different from one in which the hereinabove noted group of four (4) amino acid residues.

For example, each of the groups of four (4) amino acid residues may be of the sequence A-B-C-D, D-A-B-C, D-C-B-A, or C-B-A-D, wherein A is a hydrophobic or a small amino acid residue, C is a hydrophilic or a small amino acid residue, preferably a basic or neutral hydrophilic amino acid residue. At least one A of two adjacent groups, however, is hydrophobic and at least one C of two adjacent groups is basic hydrophilic, as the net charge of the peptide is positive. B and D can be any amino acid residue, whereby B and D may be the same or different. Preferably, the peptide chain may comprise about two (2) to about twelve (12) groups of this sequence. The A, B, C, and D of each group may be the same or may be different in some or all of the groups.

The hydrophobic amino acid residues may be selected from the group including, but not limited to, AiB, Cys, Phe, Ile, Leu, Met, Val, Trp, Tyr, norleucine (Nle), norvaline (Nva), and cyclohexylalanine (Cha). The small amino acid residues may be selected from the group including, but not limited to, Ala, Gly, Pro, Ser and Thr. The basic hydrophilic amino acid residues may be selected from the group including, but not limited to, Lys, Arg, His, Orn, homoarginine (Har), 2,4-diaminobutyric acid (Dbu), and p-aminophenylalanine. The neutral hydrophilic amino acid residues may be selected from the group including, but not limited to, Asn, Gln, Ser, Thr and homoserine (Hse).

The peptide chain preferably has at least eight (8) amino acid residues, and no greater than fifty (50) amino acid residues. Each peptide contains at least one α-helical domain which is defined by one of the above-described primary sequences. It is to be understood, however, that the peptide may also comprise domains other than the above-described primary sequences defining the α-helical structure. For example, the peptide may have amino acid residues extending from either or both ends of the α-helical domains of the peptide chain. Alternately, there may be one or more amino acid residues between one or more of the at least two (2) groups above-described primary sequences, each comprising four (4) amino acids, herein referred to as interhelical domains. Of course, also peptides having both interhelical domains and non-helical terminal extensions are understood to be within the scope of the invention.

In one embodiment, the peptide of the invention comprising at least two (2) groups of the above-described primary amino acid sequences defining α-helical structures which comprise sequence defined as A-B-C-D, D-A-B-C-, D-C-B-A, C-B-A-D (see, supra) may have one of the following formulae:

$$(X)_a(Z)_n(X)_b$$

and pharmaceutically acceptable salts thereof,
wherein:
Z is selected from the above-described primary. sequences consisting of A-B-C-D, D-A-B-C, D-C-B-A, C-B-A-D, whereby each Z group within one peptide may be identical or different, and whereby $Z_n$ is positively charged and contains about 20% to about 50% hydrophilic amino acid residues, preferably about 25% to about 45% hydrophilic amino acid residues;
$(X)_a$ and $(X)_b$ are amino acid assemblies of any length and composition which may not significantly contribute to the α-helical structure;
$n \geq 2$ and $a,b \geq 0$;
with the proviso that $8 \leq a+b+4n \geq 50$;
and with the further proviso that at least one A of two adjacent groups is hydrophobic and at least one C of two adjacent groups is basic hydrophilic.

In another embodiment, the peptide of the invention comprising at least two (2) groups of the above-described primary amino acid sequences defining α-helical structures which comprise sequence defined as A-B-C-D, D-A-B-C-, D-C-B-A, C-B-A-D (see, supra) may have one of the following formulae:

$$(X)_a[(Z)_n(X)_c]_d(Z)_m(X)_b$$

and pharmaceutically acceptable salts thereof,
wherein:
Z is selected from the above-described primary sequences consisting of A-B-C-D, D-A-B-C, D-C-B-A, C-B-A-D, whereby each Z group within one peptide may be identical or different, and whereby $Z_n$ and $Z_m$ are positively charged and contain about 20% to about 50% hydrophilic amino acid residues, preferably about 25% to about 45% hydrophilic amino acid residues;
$(X)_a$, $(X)_b$ and $(X)_c$ are amino acid assemblies of any length and composition which may not significantly contribute to the α-helical structure;
$n,m,d \geq 1$ and $a,b,c \geq 0$;
with the proviso that $8 \geq a+b+d(c+4n)+4m \leq 50$;
and with the further proviso that at least one A of two adjacent groups is hydrophobic and at least one C of two adjacent groups is basic hydrophilic.

The peptide chain may include amino acid residues between the hereinabove noted groups of four (4) amino acid residues provided that the spacing between such groups and the charge on the amino acid residues does not change the characteristics of the peptide chain which provide amphipathicity and a positive charge and do not adversely affect the folding characteristics of the chain to that which is significantly different from one in which the hereinabove noted group of four (4) amino acid residues.

Specific representative examples of such peptides can be found in the accompanying sequence listing of PCT Application WO94/19369, published Sep. 1, 1994, including SEQ ID NO:1, SEQ ID NO:2, SEQ ID NO:3, SEQ ID NO:4, and SEQ ID NO:5. They are incorporated herein by reference.

The peptide may have amino acid residues extending from either end of the chain. For example, the chains may have a Ser-Lys sequence before the "Ala" end, and/or an Ala-Phe sequence after the "Lys" end. Other amino acid sequences may also be attached to the "Ala" and/or the "Lys" end.

Similarly, in any peptide chain having at least three (3) groups of amino acid residues of the sequence as described above, the chain may have, for example, a C-D sequence before the first A-B-C-D group. Also other amino acid sequences may be attached to the "A" and/or the "D" end of one of these peptide chains. Also there may be amino acid residues in the chain which space one or more groups of the hereinabove noted four (4) amino acid residues from each other.

In another embodiment of the invention, the peptide may be a magainin peptide.

A magainin peptide is either a magainin such as magainin I, II or III or analogues or derivatives thereof. The magainin peptides preferably include the following basic peptide structure $X_{12}$:

$$—R_{11}—R_{11}—R_{12}—R_{13}—R_{11}—R_{14}—R_{12}—R_{11}—R_{14}—R_{12}—$$
$$R_{11}—R_{11}—R_{11}—R_{14a}—(R_{15})_n—R_{14a}—R_{14}—$$

wherein:
$R_{11}$ is a hydrophobic amino acid;
$R_{12}$ is a basic hydrophilic amino acid;
$R_{13}$ is a hydrophobic, neutral hydrophilic, or basic hydrophilic amino acid;
$R_{14}$ and $R_{14a}$ are hydrophobic or basic hydrophilic amino acid residues; and
$R_{15}$ is glutamic acid or aspartic acid, or a hydrophobic or a basic hydrophilic amino acid, and n is zero (0) or one (1).

In a preferred embodiment, $R_{13}$ is a hydrophobic or neutral hydrophilic amino acid;
$R_{14a}$ is a hydrophobic amino acid; and
$R_{15}$ is glutamic acid or aspartic acid.

Thus, for example, a magainin peptide may include the following structure:

$$Y_{12}-X_{12}$$

where $X_{12}$ is the hereinabove described basic peptide structure and $Y_{12}$ is (i) $R_{12}$
(ii) $R_{14a}-R_{12}$
(iii) $R_{11}-R_{14a}-R_{12}$
(iv) $R_{14}-R_{11}-R_{14a}-R_{12}$ where $R_{11}$, $R_{12}$, $R_{14}$ and $R_{14a}$ are as previously defined A magainin peptide may also have the following structure:

$$X_{12}-Z_{12}$$

where $X_{12}$ is as previously defined and $Z_{12}$ is:

(i) $R_{16}$ where $R_{16}$ is a basic hydrophilic amino acid or asparagine or glutamine.
(ii) $R_{16}-R_{17}$ where $R_{17}$ is a neutral hydrophilic amino acid, a hydrophobic amino acid, or a basic hydrophilic amino acid. Preferably, $R_{17}$ is a neutral hydrophilic amino acid residue.

A magainin peptide may also have the following structure:

$$(Y_{12})_a-X_{12}-(Z_{12})_b$$

where $X_{12}$, $Y_{12}$, and $Z_{12}$ are as previously defined and "a" is zero (0) or one (1) and "b" is zero (0) or one (1).

The magainin peptides may also include the following basic peptide structure $X_{13}$:

$$-R_{14}-R_{11}-R_{14a}-R_{12}-R_{11}-R_{11}-R_{12}-R_{13}-R_{11}-R_{14}-R_{12}-R_{11}-R_{11}-R_{12}-,$$

where $R_{11}$, $R_{12}$, $R_{13}$, $R_{14}$, and $R_{14a}$ are amino acid residues as hereinabove described.

The magainin peptide may also include the following structure:

$$X_{13}-Z_{13}$$

where $X_{13}$ is the hereinabove described basic peptide structure; and $Z_{13}$ is $(R_{11})_n-(R_{11})_n-(R_{11})_n-(R_{14a})_n-(R_{15})_n-(R_{14a})_n-(R_{14})_n-(R_{16})_n-(R_{17})_n$ where $R_{11}$, $R_{14}$, $R_{14a}$, $R_{15}$, $R_{16}$, and $R_{17}$ are as hereinabove described;

n is zero (0) or one (1), and each may be the same or different.

The magainin peptides generally include at least ten (10) amino acid residues and may include up to fifty (50) amino acid residues. A magainin peptide preferably has twenty two (22) or twenty three (23) amino acid residues. Accordingly, the hereinabove described basic peptide structures of a magainin peptide may include additionally amino acid residues at the amino terminus or at the carboxyl terminus, or at both ends.

Representative examples of such magainin peptides can be found in the accompanying sequence listing of PCT Application WO94/19369, published Sep. 1, 1994, including SEQ ID NO:6 ((OH) or (NH$_2$) ) (Magainin I), SEQ ID NO:7 ((OH) or (NH$_2$)) (Magainin II), SEQ ID NO:8 ((OH) or (NH$_2$)) (Magainin III), SEQ ID NO:9 ((OH) or (NH$_2$)), SEQ ID NO:10 ((OH) or (NH$_2$) SEQ ID NO:11 ((OH) or (NH$_2$)). They are incorporated herein by reference.

Magainin peptides are described in Zasloff, 1987, Proc. Natl. Acad. Sci. USA 84:5449–5493. The term "magainin peptides" as used herein refers to the basic magainin structure as well as derivatives and analogues thereof, including but not limited to the representative derivatives or analogues.

In still another embodiment of the invention, the peptide may be a PGLa peptide or an XPF peptide.

A PGLa peptide is either PGLa or an analogue or derivative thereof. The PGLa peptides preferably include the following basic peptide structure $X_{14}$:

$$R_{11}-R_{17}-R_{12}-R_{11}-R_{14}-R_{14}-R_{11}-R_{11}-R_{14}-R_{12}-R_{11}-R_{11}-R_{12}-R_{11}-R_{11}-R_{11}-R_{12}-$$

where $R_{11}$, $R_{12}$, $R_{14}$, and $R_{17}$ are as previously defined.

The PGLa peptides generally include at least seventeen (17) amino acid residues and may include as many as forty (40) amino acid residues. Accordingly, the hereinabove described basic peptide structure for a PGLa peptide may include additional amino acid residues at the amino end or at the carboxyl end or at both the amino and carboxyl end.

Thus, for example, a PGLa peptide may have the following structure:

$$-Y_{14}-X_{14}-$$

where $X_{14}$ is as previously defined and $Y_{14}$ is (i) $R_{11}$;
(ii) $R_{14}-R_{11}$ where $R_{11}$ and $R_{14}$ are as previously defined.

For example, a PGLa peptide may also have the following structure:

$$-X_{14}-Z_{14}-$$

where $X_{14}$ is as previously defined, and $Z_{14}$ is:

(i) $R_{11}$; or
(ii) $R_{11}-R_{11}$ where $R_{11}$ is as previously defined.

A PGLa peptide may also have the following structure:

$$(Y_{14})_a-X_{14}-(Z_{14})_b$$

where $X_{14}$; $Y_{14}$ and $Z_{14}$ are as previously defined, "a" is zero (0) or one (1) and "b" is zero (0) or one (1).

An XPF peptide is either XPF or an analogue or derivative thereof. The XPF peptides preferably include the following basic peptide structure $X_{16}$:

$$R_{11}-R_{17}-R_{12}-R_{11}-R_{14}-R_{18}-R_{17}-R_{11}-R_{14}-R_{12}-R_{11}-R_{11}-R_{12}-R_{11}-R_{11}-R_{11}-R_{12}-R_{12}-(R_{15})_n-R_{11}-,$$

where $R_{11}$, $R_{12}$, $R_{14}$, $R_{15}$, and $R_{17}$ are as previously defined and $R_{18}$ is glutamine or asparagine or a basic hydrophilic, or hydrophobic amino acid and n is zero (0) or one (1).

The XPF peptides generally include at last nineteen (19) amino acid residues and may include up to forty (40) amino acid residues. Accordingly, the hereinabove described basic peptide structure of XPF may include additional amino acid residues at the amino end, or at the carboxyl end or at both the amino and carboxyl ends.

Thus, for example, an XPF peptide may include the following structure:

$$Y_{16}\text{—}X_{16}$$

where $X_{16}$ is as previously defined and $Y_{16}$ is
(i) $R_{11}$ or
(ii) $R_{14}\text{—}R_{11}$
where $R_{11}$ and $R_{14}$ are as previously defined.

An XPF peptide may include the following structure:

$$X_{16}\text{—}Z_{16}$$

where $X_{16}$ is as previously defined and $Z_{16}$ is
(i) $R_{11}$; or
(ii) $R_{11}\text{—}R_{18}$; or
(iii) $R_{11}\text{—}R_{18}\text{-Pro}$; or
(iv) $R_{11}\text{—}R_{18}\text{-Pro-}R_{12}$ An XPF peptide may also have the following structure:

$$(Y_{16})_a\text{—}X_{16}\text{—}(Z_{16})_b$$

where $X_{16}$, $Y_{16}$ and $Z_{16}$ are as previously defined, "a" is zero (0) or one (1), and "b" is zero (0) or one (1).

Preferred are XPF or PGLa peptides, which are characterized by the following primary amino acid sequences as given in the accompanying sequence listing of PCT Application WO94/19369, published Sep. 1, 1994, including SEQ ID NO:12 (NH$_2$) (PGLa), and SEQ ID NO:13 (XPF). They are incorporated herein by reference.

A review of XPF and PGLa can be found in Hoffman et al., 1983, *EMBO J.* 2:711–714; Andreu et al., 1985, *Biochem. J. 149:531–535*; Gibson et al., 1986, *J. Biol. Chem.* 261:5341–5349; and Giovannini et al., 1987, *Biochem. J.* 243:113–120.

In yet another embodiment, the peptide may be a CPF peptide or appropriate analogue or derivative thereof.

CPF peptides as well as analogues and derivatives thereof are herein sometimes referred to collectively as CPF peptides.

The CPF peptide may be one which includes the following basic peptide structure $X_{20}$:

$$\text{—}R_{21}\text{—}R_{21}\text{—}R_{22}\text{—}R_{22}\text{—}R_{21}\text{—}R_{21}\text{—}R_{23}\text{—}R_{21}\text{—}R_{21}\text{—}R_{21}\text{—}$$
$$R_{23}\text{—}R_{21}\text{—}R_{21}\text{—}R_{24}\text{—}R_{25}\text{—}R_{21}\text{—}:$$

wherein:

$R_{21}$ is a hydrophobic amino acid;

$R_{22}$ is a hydrophobic amino acid or a basic hydrophilic amino acid;

$R_{23}$ is a basic hydrophilic amino acid;

$R_{24}$ is a hydrophobic or neutral hydrophilic amino acid; and $R_{25}$ is a basic or neutral hydrophilic amino acid.

The hereinabove basic structure is hereinafter symbolically indicated as $X_{20}$.

The hydrophobic amino acid residues are Ala, Cys, Phe, Gly, Ile, Leu, Met, Val, Trp, Tyr, norleucine (Nle), norvaline (Nva), and cyclohexylalanine (Cha).

The neutral hydrophilic amino acid residues are Asn, Gln, Ser, Thr, and homoserine (Hse).

The basic hydrophilic amino acid residues are Lys, Arg, His, Orn, homoarginine (Har), 2,4-diaminobutyric acid (Dbu), and p-aminophenylalanine.

The CPF peptide may include only the hereinabove noted amino acid residues or may include additional amino acid residues at the amino and/or carboxyl end or both the amino and carboxyl end. In general, the peptide does not include more than forty (40) amino acid residues.

The CPF peptides including the above basic structure preferably have from one (1) to four (4) additional amino acid residues at the amino end.

Accordingly, such preferred peptides may be represented by the structural formula:

$$Y_{20}\text{—}X_{20}$$

where $X_{20}$ is the hereinabove described basic peptide structure and $Y_{20}$ is
(i) $R_{25}\text{—}$; or
(ii) $R_{22}\text{—}R_{25}$; or
(iii) $R_{21}\text{—}R_{22}\text{—}R_{25}$; or
(iv) $R_{22}\text{—}R_{21}\text{—}R_{22}\text{—}R_{25}$;
preferably:

$$\text{Glycine —}R_{21}\text{—}R_{22}\text{—}R_{25},$$

where $R_{21}$, $R_{22}$, and $R_{25}$ are as previously defined.

The carboxyl end of the basic peptide structure may also have additional amino acid residues which may range from one (1) to thirteen (13) additional amino acid residues.

In a preferred embodiment, the basic structure may have from one (1) to seven (7) additional amino acid residues at the carboxyl end, which may be represented as follows:

$$X_{20}\text{—}Z_{20}$$

where $X_{20}$ is the hereinabove defined basic peptide structure
and $Z_{20}$ is
(i) $R_{21}\text{—}$; or
(ii) $R_{21}\text{—}R_{21}$; or
(iii) $R_{21}\text{—}R_{21}\text{—}R_{24}$; or
(iv) $R_{21}\text{—}R_{21}\text{—}R_{24}\text{—}R_{24}$; or
(v) $R_{21}\text{—}R_{21}\text{—}R_{24}\text{—}R_{24}\text{—}R_{26}$; or
(vi) $R_{21}\text{—}R_{21}\text{—}R_{24}\text{—}R_{24}\text{—}R_{26}\text{—}$ Gln; or
(vii) $R_{21}\text{—}R_{21}\text{—}R_{24}\text{—}R_{24}\text{—}R_{26}\text{—}$ Gln-Gln;
where $R_{21}$ and $R_{24}$ are as previously defined; and
$R_{26}$ is proline or a hydrophobic amino acid.

Preferred peptides may be represented by the following structural formula:

$$(Y_{20})_a\text{—}X_{20}\text{—}(Z_{20})_b$$

where $X_{20}$, $Y_{20}$ and $Z_{20}$ are as previously defined and "a" is zero (0) or one (1) and "b" is zero (0) or one (1).

Representative examples of CPF peptides which may be employed, some of which have been described in the literature, include sequences as given in the accompanying sequence listing of PCT Application WO 94/19369, published Sep. 1, 1994, including SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, and SEQ ID NO:26. They are incorporated herein by reference. A review of the CPF peptides can be found in Richter et al., 1986, *J. Biol. Chem.* 261:3676–3680; Wakabayashi et al., 1985, *Nucleic Acids Res.* 13:1817–1828; and Gibson et al., 1986, *J. Biol. Chem.* 261:5341–5349. Further examples of derivatives and analogues of CPF peptides useful in the present invention are described in U.S. Pat. No. 5,073,542.

In still another embodiment, the peptide may include one of the following basic structures $X_{31}$ through $X_{37}$, wherein:

$X_{31}$ is —$[R_{31}—R_{32}—R_{32}—R_{33}—R_{31}—R_{32}—R_{32}]_n$—;
$X_{32}$ is —$[R_{32}—R_{32}—R_{33}—R_{31}—R_{32}—R_{32}—R_{31}]_n$—;
$X_{33}$ is —$[R_{32}—R_{33}—R_{31}—R_{32}—R_{32}—R_{31}—R_{32}]_n$—;
$X_{34}$ is —$[R_{33}—R_{31}—R_{32}—R_{32}—R_{31}—R_{32}—R_{32}]_n$—;
$X_{35}$ is —$[R_{31}—R_{32}—R_{32}—R_{31}—R_{32}—R_{32}—R_{33}]_n$—;
$X_{36}$ is —$[R_{32}—R_{32}—R_{31}—R_{32}—R_{32}—R_{33}—R_{31}]_n$—;
$X_{37}$ is —$[R_{32}—R_{31}—R_{32}—R_{32}—R_{33}—R_{31}—R_{32}]_n$—;
wherein:

$R_{31}$ is a basic hydrophilic amino acid;

$R_{32}$ is a hydrophobic amino acid;

$R_{33}$ is a neutral hydrophilic, basic hydrophilic, or hydrophobic amino acid, and n is from two (2) to five (5).

The basic hydrophilic amino acid residues may be selected from the class consisting of Lys, Arg, His, Orn, homoarginine (Har), 2,4-diaminobutryric acid (Dbu), and p-aminophenylalanine.

The hydrophobic amino acid residues may be selected from the class consisting of Ala, Cys, Phe, Gly, Ile, Leu, Met, Pro, Val, Trp and Tyr, norleucine (Nle), norvaline (Nva), and cyclohexylalanine (Cha).

The neutral hydrophilic amino acid residues may be selected from the class consisting of Asn, Gln, Ser, Thr, and homoserine (Hse).

In accordance with one embodiment, when the peptide includes the structure $X_{31}$, the peptide may include the following structure:

$$Y_{31}—X_{31}$$

where $X_{31}$ is as hereinabove described, and $Y_{31}$ is:
(i) $R_{32}$;
(ii) $R_{32}—R_{32}$;
(iii) $R_{31}—R_{32}—R_{32}$;
(iv) $R_{33}—R_{31}—R_{32}—R_{32}$;
(v) $R_{32}—R_{33}—R_{31}—R_{32}—R_{32}$; or
(vi) $R_{32}—R_{32}—R_{33}—R_{31}—R_{32}—R_{32}$, where $R_{31}$, $R_{32}$, and $R_{33}$ are as hereinabove described.

In accordance with another embodiment, when the peptide includes the structure $X_{31}$, the peptide may include the following structure:

$$X_{31}—Z_{31}$$

where $X_{31}$ is as hereinabove described, and $Z_{31}$ is:
(i) $R_{31}$;
(ii) $R_{31}—R_{32}$;
(iii) $R_{31}—R_{32}—R_{32}$;
(iv) $R_{31}—R_{32}—R_{32}—R_{33}$;
(v) $R_{31}—R_{32}—R_{32}—R_{33}—R_{31}$; or
(vi) $R_{31}—R_{32}—R_{32}—R_{33}—R_{31}—R_{32}$.

In accordance with yet another embodiment, the peptide may include the following structure:

$$(Y_{31})_a—X_{31}—(Z_{31})_b,$$

where $Y_{31}$ and $Z_{31}$ are as previously defined, "a" is zero (0) or one (1), and "b" is zero (0) or one (1).

When the peptide includes the structure $X_{33}$, the peptide may include the following structure:

$$Y_{32}—X_{32}$$

where $X_{32}$ is as hereinabove described, and $Y_{32}$ is:
(i) $R_{31}$;
(ii) $R_{32}—R_{31}$;
(iii) $R_{32}—R_{32}—R_{31}$;
(iv) $R_{31}—R_{32}—R_{32}—R_{31}$;
(v) $R_{33}—R_{31}—R_{32}—R_{32}—R_{31}$; or
(vi) $R_{32}—R_{33}—R_{31}—R_{32}—R_{32}—R_{31}$.

In another embodiment, when the peptide includes the structure $X_{32}$, the peptide may include the following structure:

$$X_{32}—Z_{32}$$

where $X_{32}$ is as hereinabove described, and $Z_{32}$ is:
(i) $R_{32}$;
(ii) $R_{32}—R_{32}$;
(iii) $R_{32}—R_{32}—R_{33}$;
(iv) $R_{32}—R_{32}—R_{33}—R_{31}$;
(v) $R_{32}—R_{32}—R_{33}—R_{31}—R_{32}$; or
(vi) $R_{32}—R_{32}—R_{33}—R_{31}—R_{32}—R_{32}$.

In accordance with yet another embodiment, the peptide may include the following structure:

$$(Y_{32})_a—X_{32}—(Z_{32})_b,$$

where $Y_{32}$ and $Z_{32}$ are as previously defined, a is 0 or 1, and b is 0 or 1.

In accordance with another embodiment, when the peptide includes the structure $X_{33}$, the peptide may include the following structure:

$$Y_{33}—X_{33}$$

where $X_{33}$ is as hereinabove described, and $Y_{33}$ is:
(i) $R_{32}$;
(ii) $R_{31}—R_{32}$;
(iii) $R_{32}—R_{31}—R_{32}$;
(iv) $R_{32}—R_{32}—R_{31}—R_{32}$;
(v) $R_{31}—R_{32}—R_{32}—R_{31}—R_{32}$;
(vi) $R_{33}—R_{31}—R_{32}—R_{32}—R_{31}—R_{32}$;

where $R_{31}$, $R_{32}$, $R_{33}$ are as hereinabove described.

In accordance with another embodiment, when the peptide includes the structure $X_{33}$, the peptide may include the following structure:

$$X_{33}—Z_{33}$$

where $X_{33}$ is as hereinabove described, and $Z_{33}$ is:
(i) $R_{32}$;
(ii) $R_{32}—R_{33}$;
(iii) $R_{32}—R_{33}—R_{31}$;
(iv) $R_{32}—R_{33}—R_{31}—R_{32}$;
(v) $R_{32}—R_{33}—R_{31}—R_{32}—R_{32}$;
(vi) $R_{32}—R_{33}—R_{31}—R_{32}—R_{32}—R_{31}$.

In accordance with yet another embodiment, the peptide may include the following structure:

$$(Y_{33})_a—X_{33}—(Z_{33})_b$$

where $Y_{33}$ and $Z_{33}$ are as previously defined, "a" is zero (0) or one (1), and "b" is zero (0) or one (1).

In yet another embodiment, when the peptide includes the structural $X_{34}$, the peptide may include the following structure.

$$Y_{34}—X_{34}$$

where $X_{34}$ is as hereinabove described, and $Y_{34}$ is:
(i) $R_{32}$;
(ii) $R_{32}—R_{32}$;
(iii) $R_{31}—R_{32}—R_{32}$;
(iv) $R_{32}—R_{31}—R_{32}—R_{32}$;
(v) $R_{32}—R_{32}—R_{31}—R_{32}—R_{32}$; or
(vi) $R_{31}—R_{32}—R_{32}—R_{31}—R_{32}—R_{32}$;
where $R_{31}$, $R_{32}$, $R_{33}$ are as hereinabove described.

In still another embodiment, when the peptide includes the structure $X_{34}$, the peptide may include the following structure:

$$X_{34}—Z_{34}$$

where $X_{34}$ is as hereinabove described, and $Z_{34}$ is:
(i) $R_{33}$;
(ii) $R_{33}—R_{31}$;
(iii) $R_{33}—R_{31}—R_{32}$;
(iv) $R_{33}—R_{31}—R_{32}—R_{32}$;
(v) $R_{33}—R_{31}—R_{32}—R_{32}—R_{31}$; or
(vi) $R_{33}—R_{31}—R_{32}—R_{32}—R_{32}—R_{32}$.

In yet another embodiment, the peptide may include the following structure:

$$(Y_{34})_a—X_{34}—(Z_{34})_b$$

where $X_{34}$ and $Z_{34}$ are as previously defined, "a" is zero (0) or one (1), and "b" is zero (0) or one (1).

In a still further embodiment, when the peptide includes the structure $X_{35}$, the peptide may include the following structure:

$$Y_{35}—X_{35}$$

where $X_{35}$ is as hereinabove described, and $Y_{35}$ is:
(i) $R_{33}$;
(ii) $R_{32}—R_{33}$;
(iii) $R_{32}—R_{32}—R_{33}$;
(iv) $R_{31}—R_{32}—R_{32}—R_{33}$;
(v) $R_{32}—R_{31}—R_{32}—R_{32}—R_{33}$; or
(vi) $R_{32}—R_{32}—R_{31}—R_{32}—R_{32}—R_{33}$;
where $R_{31}$, $R_{32}$, and $R_{33}$ are as hereinabove described.

In another embodiment, when the peptide includes the structure $X_{35}$, the peptide may include the following structure:

$$X_{35}—Z_{35}$$

where $X_{35}$ is as hereinabove described, and $Z_{35}$ is:
(i) $R_{31}$;
(ii) $R_{31}—R_{32}$;
(iii) $R_{31}—R_{32}—R_{32}$;
(iv) $R_{31}—R_{32}—R_{32}—R_{31}$;
(v) $R_{31}—R_{32}—R_{32}—R_{31}—R_{32}$; or
(vi) $R_{31}—R_{32}—R_{32}—R_{31}—R_{32}—R_{32}$.

In yet another embodiment, the peptide may include the following structure:

$$(Y_{35})_a—X_{35}—(Z_{35})_b$$

where $X_{35}$ and $Z_{35}$ are as previously defined, "a" is zero (0) or one (1), and "b" is zero (0) or one (1).

In a further embodiment, when the peptide includes the structure $X_{36}$ the peptide may include the following structure:

$$Y_{36}—X_{36}$$

where $X_{36}$ is a hereinabove described, and $Y_{36}$ is:
(i) $R_{31}$;
(ii) $R_{33}—R_{31}$;
(iii) $R_{32}—R_{33}—R_{31}$;
(iv) $R_{32}—R_{32}—R_{33}—R_{31}$;
(v) $R_{31}—R_{32}—R_{32}—R_{33}—R_{31}$; or
(vi) $R_{32}—R_{31}—R_{32}—R_{31}—R_{33}—R_{31}$;
where $R_{31}$, $R_{32}$, and $R_{33}$ are as hereinabove described.

In another embodiment, when the peptide includes the structure $X_{36}$, the peptide may include the following structure:

$$X_{36}—Z_{36}$$

where $X_{36}$ is as hereinabove described, and $Z_{36}$ is:
(i) $R_{32}$;
(ii) $R_{32}—R_{32}$;
(iii) $R_{32}—R_{32}—R_{31}$;
(iv) $R_{32}—R_{32}—R_{31}—R_{32}$;
(v) $R_{32}—R_{32}—R_{31}—R_{32}—R_{32}$; or
(vi) $R_{32}—R_{32}—R_{31}—R_{32}—R_{32}—R_{33}$.

In yet another embodiment, the peptide may include the following structure:

$$(Y_{36})_a—X_{36}—(Z_{36})_b$$

where $Y_{36}$ and $Z_{36}$ are as previously defined, "a" is zero (0) or one (1), and "b" is zero (0) or one (1).

In one embodiment, when the peptide includes the structure $X_{37}$, the peptide may include the structure:

$$Y_{37}—X_{37}$$

where $X_{37}$ is as hereinabove described, and $Y_{37}$ is:
(i) $R_{32}$;
(ii) $R_{31}—R_{32}$;
(iii) $R_{33}—R_{31}—R_{32}$;
(iv) $R_{32}—R_{33}—R_{31}—R_{32}$;
(v) $R_{32}—R_{32}—R_{33}—R_{31}—R_{32}$; or
(vi) $R_{31}—R_{32}—R_{32}—R_{33}—R_{31}—R_{32}$;
where $R_{31}$, $R_{32}$, and $R_{33}$ are as hereinabove described.

In accordance with a further embodiment, when the peptide includes the structure $X_{37}$, the peptide may include the following structure:

$$X_{37}—Z_{37}$$

where $X_{37}$ is as hereinabove described, and $Z_{37}$ is:
(i) $R_{32}$;
(ii) $R_{32}—R_{31}$;
(iii) $R_{32}—R_{31}—R_{32}$;

(iv) $R_{32}$—$R_{31}$—$R_{32}$—$R_{32}$;
(v) $R_{32}$—$R_{31}$—$R_{32}$—$R_{32}$—$R_{33}$; or
(vi) $R_{32}$—$R_{31}$—$R_{32}$—$R_{32}$—$R_{33}$—$R_{31}$.

In accordance with yet another embodiment, the peptide may include the following structure:

$$(Y_{37})_a\text{—}X_{37}\text{—}(Z_{37})_b$$

where $Y_{37}$ and $Z_{37}$ are as previously defined, "a" is zero (0) or one (1), and "b" is zero (0) or one (1).

In a preferred embodiment, n is three (3).

Examples of such peptides can be found in the accompanying sequence listing of PCT Application WO94/19369, published Sep. 1, 1994, including SEQ ID NO:27, SEQ ID NO:28, SEQ ID NO:29, SEQ ID NO:30, SEQ ID NO:31, SEQ ID NQ:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, and SEQ ID NO:69. They are incorporated herein by reference.

In SEQ ID NO:67 and SEQ ID NO:68, $X_{aa}$ is p-aminophenylalanine (see, accompanying sequence listing of PCT Application WO94/19369, published Sep. 1, 1994).

In still another embodiment, the amphipathic peptide includes the following basic structure $X_{40}$:

$$R_{31}\text{—}R_{32}\text{—}R_{32}\text{—}R_{33}\text{—}R_{34}\text{—}R_{32}\text{—}R_{32}\text{—}R_{31}\text{—}R_{32}\text{—}R_{32}\text{—}R_{32}\text{—}R_{34}\text{—}R_{32}\text{—}R_{32},$$

where $R_{31}$, $R_{32}$, and $R_{33}$ are as hereinabove described, and $R_{34}$ is a basic hydrophilic or hydrophobic amino acid.

In accordance with one embodiment, the peptide may include the following structure:

$$Y_{40}\text{—}X_{40}$$

where $X_{40}$ is as hereinabove described, and $Y_{40}$ is:
(i) $R_{32}$;
(ii) $R_{32}$—$R_{32}$;
(iii) $R_{34}$—$R_{32}$—$R_{32}$;
(iv) $R_{33}$—$R_{34}$—$R_{32}$—$R_{32}$;
(v) $R_{32}$—$R_{33}$—$R_{34}$—$R_{32}$—$R_{32}$;
(vi) $R_{32}$—$R_{32}$—$R_{33}$—$R_{34}$—$R_{32}$—$R_{32}$; or
(vii) $R_{31}$—$R_{32}$—$R_{32}$—$R_{33}$—$R_{34}$—$R_{32}$—$R_{32}$;
where $R_{31}$, $R_{32}$, $R_{33}$ and $R_{34}$ are as hereinabove described.

In one embodiment, the peptide may include the following structure:

$$X_{40}\text{—}Z_{40}$$

where $X_{40}$ is as hereinabove described, and $Z_{40}$ is:
(i) $R_{31}$;
(ii) $R_{31}$—$R_{32}$;
(iii) $R_{31}$—$R_{32}$—$R_{32}$;
(iv) $R_{31}$—$R_{32}$—$R_{32}$—$R_{33}$;
(v) $R_{31}$—$R_{32}$—$R_{32}$—$R_{33}$—$R_{34}$;
(vi) $R_{31}$—$R_{32}$—$R_{32}$—$R_{33}$—$R_{34}$—$R_{32}$; or
(vii) $R_{31}$—$R_{32}$—$R_{32}$—$R_{33}$—$R_{34}$—$R_{32}$—$R_{32}$;
where $R_{31}$, $R_{32}$, $R_{33}$ and $R_{34}$ are as hereinabove described.

In yet another embodiment the peptide may include the following structure:

$$(Y_{40})_a\text{—}X_{40}\text{—}(Z_{40})_b$$

where $Y_{40}$ and $Z_{40}$ are as previously defined, "a" is zero (0) or one (1) and "b", is zero (0) or one (1).

Examples of such peptides can be found in the accompanying sequence listing of PCT Application WO94/19369, published Sep. 1, 1994, including SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, SEQ ID NO:85, SEQ ID NO:86, and SEQ ID NO:87. They are incorporated herein by reference.

In still another embodiment, the peptide may include the following structural formula:

—(Lys Ile Ala Lys Lys Ile Ala)$_n$, wherein n is from two (2) to five (5), preferably three (3).

In another embodiment, the peptide may include the following structural formula:

—(Lys Phe Ala Lys Lys Phe Ala)$_n$ wherein n is from-two (2) to five (5), preferably three (3).

In accordance with another embodiment, the peptide may include the following structural formula:

—(Lys Phe Ala Lys Lys Ile Ala)$_n$ wherein n is from three (3) to five (5), preferably three (3).

Examples of such peptides are given in the accompanying sequence listing of PCT Application WO94/19369, published Sep. 1, 1994, including SEQ ID NO:88, SEQ ID NO:89, SEQ ID NO:90, SEQ ID NO:91, SEQ ID NO:92, SEQ ID NO:93, and SEQ ID NO:94. They are incorporated herein by reference.

In yet another embodiment, the peptide may be cecropin or analogues or derivatives thereof (collectively referenced to as cecropins). Cecropins are described in Lee et al., 1989, *Proc. Natl. Acad. Sci. USA* 86:9159–9162; sipos et al., 1992, *Europ. J. Biochem.* 209:163–169; Agerberth et al., 1993, *Eur. J. Biochem.* 216:623–629; Gunshefski et al., 1994, *Cornea* 13:237–242; Callaway et al., 1993, *Antimicrobial Agents and Chemotherapy* 37:1614–1619; Gazit et al., 1994, *Biochemistry* 33;10681–10692; *Ann. Rev. Microbiol.* 41, pages 103–26 (1987), in particular at page 108; Christensen et al., *Proc. Natl. Acad. Sci. USA* 85:5072–5076; U.S. Pat. No. 5,206,154.

In yet another embodiment, the peptide may be sarcotoxin or analogues or derivatives thereof (collectively referenced to as sarcotoxins). Sarcotoxins and analogues and derivatives thereof are described in Alan R. Liss, Inc., 1987, *Molecular Entomology*, pages 369–78, in particular at page 375.

In still another embodiment, the amphipathic peptide includes the following basic structure $X_{50}$:

$$R_{41}\text{—}R_{42}\text{—}R_{42}\text{—}R_{41}\text{—}R_{42}\text{—}R_{42}\text{—}R_{41}\text{—}R_{41}\text{—}R_{42}\text{—}R_{41}\text{—}R_{41}$$

wherein:
$R_{41}$ is a hydrophobic amino acid; and
$R_{42}$ is a basic hydrophilic or neutral hydrophilic amino acid.

In one embodiment, the peptide includes the basic structure:

where $X_{50}$ is as hereinabove described and $Y_{50}$ is:
(i) $R_{41}$;
(ii) $R_{42}$—$R_{41}$; or
(iii) $R_{42}$—$R_{42}$—$R_{41}$; wherein $R_{41}$ and $R_{42}$ are as hereinabove described.

In one specific embodiment, $R_{41}$ is leucine. In another specific embodiment, $R_{42}$ is lysine. Representative examples of peptide in accordance with this aspect of the present invention can be found in the accompanying sequence listing of PCT Application WO94/19369, published Sep. 1, 1994, including SEQ ID NO:95, SEQ ID NO:96, SEQ ID NO:97, and SEQ ID NO:98. They are incorporated herein by reference.

In another embodiment, the amphipathic peptide includes the following basic structure $X_{52}$:

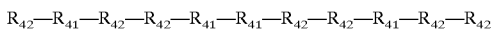

wherein:
$R_{41}$ is a hydrophobic amino acid; and
$R_{42}$ is a basic hydrophilic or neutral hydrophilic amino acid.

In one embodiment $R_{41}$ is leucine. In another embodiment, $R_{42}$ is lysine.

In one embodiment, the peptide includes the basic structure:

where $X_{52}$ is as hereinabove described, and $Y_{52}$ is:
(i) $R_{42}$;
(ii) $R_{41}$—$R_{42}$;
(iii) $R_{41}$—$R_{42}$—$R_{42}$;
(iv) $R_{42}$—$R_{42}$—$R_{41}$—$R_{42}$; or
(v) $R_{42}$—$R_{42}$—$R_{41}$—$R_{41}$—$R_{42}$.

Representative examples of peptide in accordance with this aspect of the present invention can be found in the accompanying sequence listing of PCT Application WO94/19369, published Sep. 1, 1994, including SEQ ID NO:99, which is incorporated herein by reference.

In another embodiment, the peptide includes the basic structure:

where $X_{52}$ is as hereinabove described, and $Z_{52}$ is:
(i) $R_{41}$;
(ii) $R_{41}$—$R_{41}$;
(iii) $R_{41}$—$R_{41}$—$R_{42}$;
(iv) $R_{41}$—$R_{41}$—$R_{42}$—$R_{42}$; or
(v) $R_{41}$—$R_{41}$—$R_{42}$—$R_{42}$—$R_{41}$.

Representative examples of peptide in accordance with this aspect of the present invention can be found in the accompanying sequence listing of PCT Application WO94/19369, published Sep. 1, 1994, including SEQ ID NO:100, which is incorporated herein by reference.

In another embodiment, the peptide may include the structure:

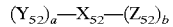

where $X_{52}$, $Y_{52}$ and $Z_{52}$ are as hereinabove described, and "a" is zero (0) or one (1), and "b" is zero (0) or one (1).

In still another embodiment, the peptide includes the following basic structure $X_{54}$:

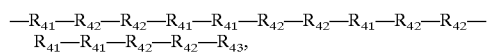

where
$R_{41}$ and $R_{42}$ are as hereinabove described, and
$R_{43}$ is a neutral hydrophilic amino acid.

Representative examples of peptide in accordance with this aspect of the present invention can be found in the accompanying sequence listing of PCT Application WO94/19369, published Sep. 1, 1994, including SEQ ID NO:101, and SEQ ID NO:102. They are incorporated herein by reference.

In accordance with yet another embodiment, the peptide includes the following structure $X_{56}$:

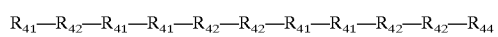

where
$R_{41}$ and $R_{42}$ are as hereinabove described, and
$R_{44}$ is a neutral hydrophilic amino acid or proline.

In still another embodiment, the peptide may include the following structure:

where $X_{56}$ is the basic peptide structure hereinabove described, and $Y_{56}$ is:
(i) —$R_{41}$;
(ii) —$R_{41}$—$R_{41}$;
(iii) —$R_{42}$—$R_{41}$—$R_{41}$;
(iv) —$R_{41}$—$R_{42}$—$R_{41}$—$R_{41}$;
(v) —$R_{41}$—$R_{41}$—$R_{42}$—$R_{41}$—$R_{41}$;
(vi) —$R_{42}$—$R_{41}$—$R_{41}$—$R_{42}$—$R_{41}$—$R_{41}$; or
(vii) —$R_{42}$—$R_{42}$—$R_{41}$—$R_{41}$—$R_{41}$—$R_{42}$—$R_{41}$—$R_{41}$;
where $R_{41}$ and $R_{42}$ are as hereinabove described.

In still another embodiment, the peptide may include the structure:

where $X_{56}$ is as hereinabove described, and $Z_{56}$ is:
(i) —$R_{42}$;
(ii) —$R_{42}$—$R_{42}$;
(iii) —$R_{42}$—$R_{42}$—$R_{41}$;
(iv) —$R_{42}$—$R_{42}$—$R_{41}$—$R_{41}$;
(v) —$R_{42}$—$R_{42}$—$R_{41}$—$R_{41}$—$R_{42}$;
(vi) —$R_{42}$—$R_{42}$—$R_{41}$—$R_{41}$—$R_{42}$—$R_{42}$; or
(vii) —$R_{42}$—$R_{42}$—$R_{41}$—$R_{41}$—$R_{42}$—$R_{42}$—$R_{41}$.

Representative examples of peptide in accordance with this aspect of the present invention can be found in the accompanying sequence listing of PCT Application WO94/19369, published Sep. 1, 1994, including SEQ ID NO:103, and SEQ ID NO:104. They are incorporated herein by reference.

In yet another embodiment, the peptide may have the structure:

$(Y_{56})_a$—$X_{56}$—$(Z_{56})_b$ where $X_{56}$, $Y_{56}$, and $Z_{56}$ are as hereinabove described, "a" is zero (0) or one (1) and "b" is zero (0) or one (1).

In still another embodiment, the peptide includes the following basic structure $X_{58}$:

$R_{41}$—$R_{41}$—$R_{42}$—$R_{42}$—$R_{41}$—$R_{42}$—$R_{42}$—$R_{41}$—$R_{41}$—$R_{42}$—$R_{42}$—$R_{41}$—$R_{43}$;

where $R_{41}$, $R_{42}$ and $R_{43}$ are as hereinabove described.

In still another embodiment, the peptide may include the structure:

$Y_{58}$—$X_{58}$ where $X_{58}$ is as hereinabove described, and $Y_{58}$ is:
(i) —$R_{41}$;
(ii) —$R_{42}$—$R_{41}$;
(iii) —$R_{42}$—$R_{42}$—$R_{41}$;
(iv) —$R_{41}$—$R_{42}$—$R_{42}$—$R_{41}$;
(v) —$R_{41}$—$R_{41}$—$R_{42}$—$R_{42}$—$R_{41}$;
(vi) —$R_{42}$—$R_{41}$—$R_{41}$—$R_{42}$—$R_{42}$—$R_{41}$; or
(vii) —$R_{42}$—$R_{42}$—$R_{41}$—$R_{41}$—$R_{42}$—$R_{42}$—$R_{41}$;
where $R_{41}$ and $R_{42}$ are as hereinabove described.

In still another embodiment, the peptide includes the structure:

$X_{58}$—$X_{58}$ where $X_{58}$ is as hereinabove described, and $Z_{58}$ is:
(i) —$R_{41}$;
(ii) —$R_{41}$—$R_{45}$;
(iii) —$R_{41}$—$R_{45}$—$R_{45}$;
(iv) —$R_{41}$—$R_{45}$—$R_{45}$—$R_{43}$;
(v) —$R_{41}$—$R_{45}$—$R_{45}$—$R_{43}$—$R_{41}$;
(vi) —$R_{41}$—$R_{45}$—$R_{45}$—$R_{43}$—$R_{41}$—$R_{43}$;
(vii) —$R_{41}$—$R_{45}$—$R_{45}$—$R_{43}$—$R_{41}$—$R_{43}$—$R_{43}$;
(viii) —$R_{41}$—$R_{45}$—$R_{45}$—$R_{43}$—$R_{41}$—$R_{43}$—$R_{43}$—$R_{45}$; or
(ix) —$R_{41}$—$R_{45}$—$R_{45}$—$R_{43}$—$R_{41}$—$R_{43}$—$R_{43}$—$R_{45}$—$R_{43}$;

where $R_{41}$ and $R_{43}$ are as hereinabove described, and $R_{45}$ is proline.

Representative examples of peptide in accordance with this aspect of the present invention can be found in the accompanying sequence listing of PCT Application WO94/19369, published Sep. 1, 1994, including SEQ ID NO:105, which is incorporated herein by reference.

In one embodiment, the peptide may have the structure:

$(Y_{58})_a$—$X_{58}$—$(Z_{58})_b$ where $X_{58}$, $Y_{58}$, and $Z_{58}$ are as hereinabove described, "a" is zero (0) or one (1), and "b" is zero (0) or one (1).

In another embodiment, the peptide includes the following basic structure $X_{60}$:

$R_{41}$—$R_{41}$—$R_{43}$—$R_{42}$—$R_{41}$—$R_{41}$—$R_{41}$—$R_{41}$—$R_{41}$—$R_{41}$—$R_{42}$—$R_{41}$—$R_{41}$—$R_{42}$—$R_{42}$—$R_{41}$—$R_{41}$—$R_{42}$—$R_{42}$—$R_{41}$;

where $R_{41}$, $R_{42}$, and $R_{43}$ are as hereinabove described.

Representative examples of peptide in accordance with this aspect of the present invention can be found in the accompanying sequence listing of PCT Application WO94/19369, published Sep. 1, 1994, including SEQ ID NO:106, which is incorporated herein by reference.

In another embodiment, the peptide may include the structure:

$X_{60}$—$Z_{60}$ where $X_{60}$ is as hereinabove described, and $Z_{60}$ is:
(i) —$R_{42}$;
(ii) —$R_{42}$—$R_{42}$;
(iii) —$R_{42}$—$R_{42}$—$R_{41}$;
(iv) —$R_{42}$—$R_{42}$—$R_{41}$—$R_{41}$;
(v) —$R_{42}$—$R_{42}$—$R_{41}$—$R_{41}$—$R_{42}$;
(vi) —$R_{42}$—$R_{42}$—$R_{41}$—$R_{41}$—$R_{42}$—$R_{42}$; or
(vii) —$R_{42}$—$R_{42}$—$R_{41}$—$R_{41}$—$R_{42}$—$R_{42}$—$R_{41}$.

In yet another embodiment, the peptide has a structure selected from the group consisting of:
(a) $R_{41}$—$R_{42}$—$R_{42}$—$R_{41}$—$R_{42}$—$R_{42}$—$R_{41}$;
(b) $R_{41}$—$R_{41}$—$R_{42}$—$R_{42}$—$R_{41}$—$R_{42}$—$R_{42}$—$R_{41}$;
(c) $R_{42}$—$R_{41}$—$R_{41}$—$R_{42}$—$R_{42}$—$R_{41}$—$R_{42}$—$R_{42}$—$R_{41}$;
(d) $R_{42}$—$R_{42}$—$R_{41}$—$R_{41}$—$R_{42}$—$R_{42}$—$R_{41}$—$R_{42}$—$R_{42}$—$R_{41}$; or
(e) $R_{41}$—$R_{42}$—$R_{42}$—$R_{41}$—$R_{41}$—$R_{42}$—$R_{42}$—$R_{41}$—$R_{42}$—$R_{42}$—$R_{41}$;

where $R_{41}$ and $R_{42}$ are as hereinabove described.

Representative examples of peptide in accordance with this aspect of the present invention can be found in the accompanying sequence listing of PCT Application WO94/19369, published Sep. 1, 1994, including SEQ ID NO:107, SEQ ID NO:108, SEQ ID NO:109, SEQ ID NO:110, SEQ ID NO:111, SEQ ID NO:112, and SEQ ID NO:113. They are incorporated herein by reference.

In still another embodiment, the peptide may have a COOH or $CONH_2$ group at the carboxy-terminus, as for example represented by a structural formula found in the accompanying sequence listing of PCT Application WO94/19369, published Sep. 1, 1994, including SEQ ID NO:115, which is incorporated herein by reference.

As further variation of the theme, the peptide may be an analogue of such peptide wherein at least one of amino acid residues one (1) through seven (7), nine (9), eleven (11), twelve (12), fourteen (14), sixteen (16), or eighteen (18) is deleted from the peptide (see, accompanying sequence listing of PCT Application WO94/19369, published Sep. 1, 1994, SEQ ID NO:115).

Alternately, at least one of amino acid residues one (1), three (3), seven (7), nine (9), eleven (11), twelve (12), fourteen (14), sixteen (16), or eighteen (18) is deleted from the peptide. In other embodiments, amino acid residues one (1) through three (3), one (1) through four (4), one (1) through five (5), one (1) through six (6), and one (1) through seven (7) are deleted from the peptide. Examples of such peptides can be found at the same place as SEQ ID NO:116 and SEQ ID NO:117. They are incorporated herein by reference.

In still another embodiment, the peptide includes the following structural formula $X_{62}$:

$R_{41}$—$R_{41}$—$R_{42}$—$R_{41}$—$R_{41}$—$R_{42}$—$R_{42}$—$R_{41}$—$R_{41}$—$R_{42}$—$R_{42}$—$R_{41}$—$R_{42}$—$R_{42}$, wherein:

$R_{41}$ is a hydrophobic amino acid, and $R_{42}$ is a basic hydrophilic or neutral hydrophilic amino acid.

In one embodiment, $R_{41}$ is leucine, and in another embodiment, $R_{42}$ is lysine.

Representative examples of peptide in accordance with this aspect of the present invention can be found in the accompanying sequence listing of PCT Application WO94/19369, published Sep. 1, 1994, including SEQ ID NO:118, which are incorporated herein by reference.

In still another embodiment, the peptide includes the following structural formula $X_{64}$:

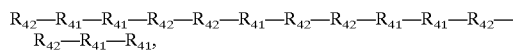
$R_{42}$—$R_{41}$—$R_{41}$—$R_{42}$—$R_{42}$—$R_{41}$—$R_{42}$—$R_{42}$—$R_{41}$—$R_{41}$—$R_{42}$—$R_{42}$—$R_{41}$—$R_{41}$, wherein:

$R_{41}$ is a hydrophobic amino acid, and $R_{42}$ is a basic hydrophilic or neutral hydrophilic amino acid.

In one embodiment, $R_{41}$ is leucine, and in another embodiment, $R_{42}$ is lysine.

Representative examples of peptide in accordance with this aspect of the present invention can be found in the accompanying sequence listing of PCT Application WO94/19369, published Sep. 1, 1994, including SEQ ID NO:119, which are incorporated herein by reference.

In still another embodiment, the peptide includes the following structural formula $X_{66}$:

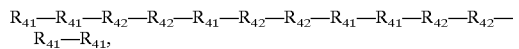
$R_{41}$—$R_{41}$—$R_{42}$—$R_{42}$—$R_{41}$—$R_{42}$—$R_{42}$—$R_{41}$—$R_{41}$—$R_{42}$—$R_{42}$—$R_{41}$—$R_{41}$, wherein:

$R_{41}$ is a hydrophobic amino acid, and $R_{42}$ is a basic hydrophilic or neutral hydrophilic amino acid.

In still another embodiment, the peptide may include the following structure:

$X_{66}$—$Z_{66}$ where $X_{66}$ is as hereinabove described and $Z_{66}$ is:

(i) —$R_{42}$;

(ii) —$R_{42}$—$R_{41}$; or (iii) —$R_{42}$—$R_{41}$—$R_{41}$.

In one specific embodiment $R_{41}$ is leucine, and in another specific embodiment, $R_{42}$ is lysine.

Representative examples of peptide in accordance with this aspect of the present invention can be found in the accompanying sequence listing of PCT Application WO94/19369, published Sep. 1, 1994, including SEQ ID NO:120, which is incorporated herein by reference.

In yet another embodiment, the peptide may be an adenoregulin or derivatives or analogues thereof (collectively referred to as adenoregulins). Adenoregulin was isolated from the skin of the frog *Phyllomedusa bicolor* and is described in Donly et al., 1992, *Proc. Natl. Acad. Sci USA* 89:10960–10963; and Amiche et al., 1993, *Biochem. Biophys. Res. Comm.* 191:983–990.

In yet another embodiment, the peptide may be a caerulein or derivatives or analogues thereof or of its precursor (collectively referred to as caeruleins). Caeruleins were isolated from the skin of the frog *Xenopus laevis* and are described in Richter et al., 1988, *J. Biol. Chem.* 261:3676–3680; and Gibson et al., 1986, *J. Biol. Chem.* 261:5341–5349.

In yet another embodiment, the peptide may be a Bacterial/Permeability-Increasing Protein (BPI) or peptides derivatives or analogues derived thereof (collectively referred to as BPIs). BPI proteins and peptides are described in Ooi et al., 1987, *J. Biol. Chem.* 262:14891–14898; Qi et al., 1994, *Biochem. J.* 298:711–718; Gray and Haseman, 1994, *Infection and Immunity* 62:2732–2739; Little et al., 1994, *J. Biol. Chem.* 269:1865–1872; and the U.S. Pat. No. 5,348,942. In particular, the generic peptide formulae and the specific examples set forth in U.S. Pat. No. 5,348,942 are specific embodiments of this invention and are incorporated herein by reference.

In yet another embodiment, the peptide may be perforin or derivatives or analogues thereof (collectively referred to as perforin). Perforin is described in Henkart, et al., 1984, *J. Exp. Med.* 160:695.

In yet another embodiment, the peptide may be insect defensins or analogues or derivatives thereof (collectively referred to as insect defensins). Insect defensins are also known as "sapecins". Insect defensins have multiple structural domains one of which is α-helical. Typically, they have six cysteines which are engaged in three intramolecular disulfide bridges, which define their characteristic structural domain pattern, an amino-terminal loop, a central α-helix and a carboxy-terminal β-sheet. As such, insect defensins differ markedly from mammalian defensins and β-defensins which have a different disulfide pattern and exist as three-stranded antiparallel β-sheets. Multiple members of the insect defensin family have been characterized, e.g., sapecin B, has been isolated from the flesh fly *Sarcophaga peregrina*. Based on the structure of this peptide, a number of synthetic peptides has been systematically developed consisting of terminal basic motifs (e.g., a RLK or a KLK motif at both ends) and internal oligo-leucine sequences. Alvarez-Bravo et al., 1994, *Biochem. J.* 302:535–538. Sapecin B and other members of the insect defensin/sapecin family are described in Yamada and Natori, 1994, *Biochem. J.* 298:623–628; Alvarez-Bravo et al., 1994, *Biochem. J.* 302:535–538; Kim et al., 1994, *FEBS Letters* 342:189–192; Shimoda et al., 1994, *FEBS Letters* 339:59–62; Yamada and Natori, 1993, *Biochem. J.* 291:275–279; Homma et al., 1992, *Biochem. J.* 288:281–284; Hanzawa et al., 1990, *FEBS Letters* 269:413–420; Kuzuhara et al., 1990, *J. Biochem.* 107:514–518; Matsuyama and Natori, 1990, *J. Biochem.* 108:128–132; U.S. Pat. No. 5,017,486; European Patent No. 303,859; European Patent No. 280,859; U.S. Pat. Nos. 5,008,371; 5,106,735; and 5,118,789.

In yet a further embodiment the peptide may be rabbit or human FALL-39/CAP-18 (Cationic Antimicrobial Protein) or analogues or derivatives thereof (collectively referred to as CAP-18s). CAP-18 was isolated from mammalian granulocytes. CAP-18s are described in PCT Application wo 94/02589 and references cited therein; Agerberth et al., 1995, *Proc. Natl. Acad. Sci. USA* 92:195–199; Larrick et al., 1991, *Biochem. Biophys. Res. Comm.* 179:170–175; Hirata et al., 1990, Endotoxin: Advances in Experimental Medicine and Biology (Herman Friedman, T. W. Klein, Masayasu Nakano, and Alois Nowotny, eds.); Tossi et al., 1994, *FEBS Letters* 339:108–112; Larrick et al., 1994, *J. Immunol.* 152:231–240; Hirata et al., 1994, *Infection and Immunity* 62:1421–1426; and Larrick et al., 1993, *Antimicrobial Agents and Chemotherapy* 37:2534–2539;

In yet a further embodiment the peptide may be PMAP (Porcine Myeloid Antibacterial Peptide) or analogues or derivatives thereof (collectively referred to as PMAPs), including PMAP-23, PMAP-36, and PMAP-37. PMAPs are further described in Zanetti et al., 1994, *J. Biol. Chem.*

269:7855–7858; Storici et al., 1994, *FEBS Letters* 37:303–307; and Tossi et al., 1995, *Eur. J. Biochem.* 228:941–948.

In yet another embodiment the peptide may be aibellin or analogues or derivatives thereof (collectively referred to as aibellins). Aibellin was isolated from the culture broth of the fungus *Verticimonosporium ellipticum* D1528, and is further described in Hino et al., 1994, *J. Dairy Sci.* 77:3426–3431; Kumazawa et al., 1994, *J. Antibiot.* 47:1136–1144; and Hino et al., 1993, *J. Dairy Sci.* 76:2213–2221.

In yet a further embodiment the peptide may be caerin or analogues or derivatives thereof (collectively referred to as caerins). Caerins were isolated from the skin or glands of Litoria splendida and Li toria caerulea and are further described in Stone et al., 1992, *J. Chem. Soc. Perkin Trans.* 1:3173–3178; and PCT WO92/13881, published Aug. 20, 1992. In yet another embodiment, the peptide may be a bombinin or analogues or derivatives thereof (collectively referred to as bombinins). Bombinins were isolated from *Bombina variegata* (Simmaco et al., 1991, *Europ. J. Biochem.* 199:217–222) and *Bombina orientalis* (Gibson et al., 1991, *J. Biol. Chem.* 266:23103–23111).

In a yet further embodiment the peptide may be a brevenin or analogues or derivatives thereof (collectively referred to as brevenins). Brevenins were isolated from the Japanese frog Rana brevipoda porsa and are further described in Morikawa et al., 1992, *Biochem. Biophys. res. Comm.* 189:184–190; and Japanese Patent Application No. 6,080, 695A.

In a yet further embodiment the peptide may be esculentin or analogues or derivatives thereof (collectively referred to as esculentins). Esculentins were isolated from the Japanese frog Rana esculenta and are further described in Simmaco et al., 1993, *FEBS Letters* 324: 159–161; and Simmaco et al., 1994, *J. Biol. Chem.* 269:11956–11961.

In yet a further embodiment the peptide may be lactoferrins or analogues or derivatives thereof (collectively referred to as lactoferrins). Lactoferrins are further described in U.S. Pat. Nos. 5,317,084; 5,304,633; European Patent Application No. 519,726 A2; European Patent application No. 503,939 A1PCT Application WO 93/22348, published Nov. 11, 1993; PCT Application WO90/13642; and Tomita et al., in: "Lactoferrin structure and function", (Hutchens, T. W., et al., edt.), Plenum Press, NY, 1994, pp 209–218.

In yet a further embodiment the peptide may be a CEMA peptide or analogues or derivatives thereof (collectively referred to as CEMAs). CEMAs are synthetic cecropin-melittin hybrids, generated by fusion of selected cecropin and melittin sequences with additional modifications. They are further described in PCT Application WO94/04688, published Mar. 3, 1994.

In yet another embodiment, the peptide may be a dermaseptin-b or derivatives or analogues thereof (collectively referred to as dermaseptin-bs). Dermaseptin-bs were isolated from the skin of the frog *Phyllomedusa bicolor* and are described in Mor et al., 1994, *Biochemistry* 33:6642– 6650; Amiche et al., 1994, *J. Biol. Chem.* 269:17847–17852; and Strahlevitz et al., 1994, *Biochemistry* 33:10951–10960.

In a preferred embodiment, the peptide may be a dermaseptin or analogues or derivatives thereof (collectively referred to as dermaseptins). Dermaseptins were isolated from the skin of the frog *Phyllomedusa sauvagei* and are described in Mor et al., 1991, *Biochemistry* 30:8824–8830; Pouny et al., 1992, *Biochemistry* 31:12416–12423; Hernandez et al., 1992, *Eur. J. Cell. Biol.* 59:414–424; Mor et al., 1994, *J. Biol. Chem.* 269:1934–1939; Mor and Nicolas, 1994, *Eur. J. Biochem.* 219:145–154; Mor et al., 1994, *J. Biol. Chem.* 269:31635–31641; and the co-owned French Patent Application No. 9,507,831.

In another preferred embodiment, the peptide may be a Pancreatic Polypeptide (PP) or analogues or derivatives thereof (collectively referred to as PPs). The family of PPs includes PP derived from endocrine cells of pancreatic islets, NPYY derived from CNS- and PNS-derived neurons, and PYY derived from gut endocrine cells of *Rana ridibunda*. Pollock et al., 1988, *J. Biol. Chem.* 263:9746–9751; Chartrel et al., 1991, *Proc. Natl. Acad. Sci. USA* 88:3862–3866; and Conlon et iron al., 1992, *Peptides* 13:145–149. The family further includes A the most preferred SPYY, isolated from the skin of the frog Phyllomedusa bicolor and are described in Mor et al., 1994, *Proc. Natl. Acad. Sci. USA* 91:10295–10299.

In a preferred embodiment, the peptide is identified in SEQ ID NO:1:
YPPKPESPGEDASPEEMNKYLTALRHYINLVTRQRY
and pharmaceutically acceptable salts thereof.

In another preferred embodiment, the peptide is identified in SEQ ID NO:2:
YPPKPENPGEDASPEEMTKYLTALRHYINLVTRQRY
and pharmaceutically acceptable salts thereof.

In yet another preferred embodiment, the peptide is identified in SEQ ID NO:3
YPSKPDNPGEDAPAEDMAKYYSALRHYINLITRQRY
and pharmaceutically acceptable salts thereof.

In yet another preferred embodiment, the peptide is identified in SEQ ID NO:4:
YPAKPEAFGEDAS PEELSRYYASLRHYLNLVTRQRY
and pharmaceutically acceptable salts thereof.

In yet another preferred embodiment, the peptide is identified in SEQ ID NO:5:
YPSKPDNPGEDAPAEDLARYYSALRHYINLITRQRY
and pharmaceutically acceptable salts thereof.

In yet another preferred embodiment, the peptide is identified in SEQ ID NO:6:
PEEMNAKYLTALRHYINLVTRQRY
and pharmaceutically acceptable salts thereof.

In yet another preferred embodiment, the peptide is identified in SEQ ID NO:7:
ALWKTMLKKLGTMALHAGKAALGAAADTISQGTQ
and pharmaceutically acceptable salts thereof.

In yet another preferred embodiment, the peptide is identified in SEQ ID NO:8:
ALWFTMLKKLGTMALHAGKAALGAAANTISQGTQ
and pharmaceutically acceptable salts thereof.

In yet another preferred embodiment, the peptide is identified in SEQ ID NO:9:
ALWKNMLKGIGKLAGKAALGAVKKLVGAS
and pharmaceutically acceptable salts thereof.

In yet another preferred embodiment, the peptide is identified in SEQ ID NO:10:
ALWMTLLKKVLKAAAKAALNAVLVGANA
and pharmaceutically acceptable salts thereof.

In yet another preferred embodiment, the peptide is identified in SEQ ID NO:11:
ALWKTMLKKLGTMALHAG
and pharmaceutically acceptable salts thereof.

In yet another preferred embodiment, the peptide is identified in SEQ ID NO:12:
GLWSKIKTAGKSVAKAAAKAAVKAVTNAV
and pharmaceutically acceptable salts thereof.

In yet another preferred embodiment, the peptide is identified in SEQ ID NO:13:
AMWKDVLKKIGTVALHAGKAALGAVADTISQ
and pharmaceutically acceptable salts thereof.

In yet another preferred embodiment, the peptide is identified in SEQ ID NO:14:
GLWSKIKEVGKEAAKAAAKAAGKAALGAVSEAV
and pharmaceutically acceptable salts thereof.

Additional examples of cationic amphipathic α-helical peptides useful for the present invention can be found, among many other places, in PCT Application WO US94/06176, published Dec. 22, 1994; PCT Application WO94/04688; and Pires et al., 1993, *Gene* 134:7–13.

In one embodiment of the invention, the peptides or analogues or derivatives thereof useful in the present invention may have linkages other than peptide linkages, including, but not limited to —(CO)O—, —(CO)S—, —O—(CO)—NH—, —(CO)—NH—, etc. Such linkages are well-known in the art and are described, for example, in Kahns et al., 1991, *Pharm. Research* 8:1533–1538.

In another embodiment of the invention, any or all of the amino acid residues of the peptides or analogues or derivatives thereof useful in the present invention which are not glycine may be a D-amino acid residue. Although the scope of this particular embodiment is not intended to be limited to any theoretical reasoning, such modifications of the above-described peptides may increase their resistance to proteolytic enzymes while retaining biological activity.

In another embodiment of the invention, any or all of the amino acid residues of the peptides or analogues or derivatives thereof useful in the present invention which are not glycine may be a D-amino acid residue. In the specific case that all amino acid residues except glycine are D-amino acids, these peptides are referred to as enantio-peptides. Although the scope of this particular embodiment is not intended to be limited to any theoretical reasoning, such modifications of the above-described peptides may increase their resistance to proteolytic enzymes while retaining biological activity.

In another embodiment of the invention, all of the amino acid residues of the peptides or analogues or derivatives thereof useful in the present invention are L-amino acid residues, which are linked by normal peptide bonds but in the reverse sequence n . . . ,3,2,1). This class of peptides is also referred to as retro peptides.

In still another embodiment of the invention, any or all of the amino acid residues of the peptides or analogues or derivatives thereof useful in the present invention which are not glycine are D-amino acid residue, which are linked by normal peptide bonds but in the reverse sequence (n . . . ,3,2,1). In the specific case that all amino acid residues except glycine are D-amino acids, this class of peptides is referred to as retroenantio peptides.

In still another embodiment of the invention, the peptides or analogues or derivatives thereof useful in the present invention may have intrahelical linkages to stabilize the helix or intrahelical linkages to form ordered helical bundles. Since linkages are well-known in the art and include, but are not limited to, —(CO)O—, —(CO)S—, —O—(CO)—NH—, —NH—(CO)—NH—, etc. For example, an amide linkage might be formed between lysine and glutamic acid. Such linkages are well known in the art and are described, for the amide linkage between lysine to glutamic acid interhelically to stabilized the helix or intrahelically to form an ordered helices bundles.

In still another embodiment of the invention, the peptides or analogues or derivatives thereof useful in the present invention may comprise a disulfide linkage between two strands of helices in parallel or antiparallel fashion to form dimeric helices bundles.

In still another embodiment of the invention, the peptides or analogues of derivatives thereof useful in the present invention may be covalently linked in either parallel or antiparallel fashion to a template molecule. The amphipathic α-helices may be organized through covalent attachments to the template molecule in a number which is defined by the stoichiometry of the assembled bundle around a central hydrophilic pore. This approach is further described in Tomich et al., 1994, *Int. J. Peptide Protein Res.*, 43:597–607; Tam et al., 1995, *J. Amer. Chem. Soc.*, 117:3893–3899, Sasaki, 1989, *J. Am. Chem. Soc.*, 111:380–381, Rivier et al., 1992, *J. Am. Chem. Soc.*, 114:1463–1470.)

In a still further embodiment, the active peptide(s) or analogues derivatives useful in the invention may be modified at their N- and/or C-terminal ends. Such modifications are well known in the art and are described in, for example, "Compositions and Treatment with Biologically Active Peptides Having C-Terminal Substitutions", WO 92/22317, published Dec. 23, 1992, and "Amino Acids and Peptides Having Modified Terminals", WO 94/15909, published Jul. 21, 1994.

For example, the amino terminus of the peptide may be in the free amino form or may be acylated by a group of the formula RCO-, wherein R represents a hydrocarbyl group of 1–18 carbon atoms. The hydrocarbyl group is saturated or unsaturated and is typically, for example, methyl, ethyl, i-propyl, t-butyl, n-pentyl, octanoyl, cyclohexyl, cyclohexene-2-yl, hexene-3-yl, hexyne-4-yl, and the like. Other modifications at the N-terminus include, but are not limited to, substitutions with a lauryl group. General information about N-terminal modifications and substitutions can be found, among other places, in Molinero et al., 1990, *Peptides* (Giralt et al., edts.), pp 436–437.

Modifications of the C-terminus include, but are not limited to, substitutions by C-terminal esters, C-terminal hydrazides, C-terminal hydroxylamines, or C-terminal amides. The carboxyl terminus may also be derivatized by formation of an ester with an alcohol of the formula ROH, or may be amidated by an amine of the formula $NH_3$, or $RNH_2$, or $R_2NH$, wherein each R is independently hydrocarbyl of 1–18 carbon atoms as defined above. Amidated forms of the peptides wherein the C-terminus has the formula $CONH_2$ are preferred.

Modification of either or both the N- or C-termini might increase the biological half-life of the active peptide(s) or analogues or derivatives thereof, although again it is to be understood that the scope of the invention is understood not to be limited to any such theoretical reasoning.

As the peptides of the invention contain substantial numbers of basic amino acids, the peptides of the invention may be supplied in the form of the acid addition salts. Typical acid addition salts include those of inorganic ions such as chloride, bromide, iodide, fluoride or the like, sulfate, nitrate, or phosphate, or may be salts of organic anions such as acetate, triflouro acetate, formate, benzoate and the like. The acceptability of each of such salts is dependent on the intended use, as is commonly understood.

The compositions of the present invention used for the treatment and for prevention of diseases specified hereinbelow (see, Section V./D.) comprise at least one of the above described peptides as active component in an amount effective to activate cells of the monocyte/macrophage lineage and/or other lymphoid cells of the host. Generally, at least one active peptide is present in an amount to achieve a serum level of the peptide of about $10^{-9}$ M to $10^{-5}$ M, typically the amount administered will be to achieve a serum peptide level of about $10^{-9}$ M into about $10^{-6}$ M. However, such amount effective to activate the host's immune system may vary for particular diseases and/or modes of treatment and may be determined by the skilled artisan for every individual case by employing suitable in vivo and/or in vitro assays which are well-known in the art. A preferred assay for measuring, for example, the macrophage stimulating activity of the peptides useful for the methods of the present invention is a TNF-α secretion assay described, for example, Horneff et al., 1993, *Clin. Exp. Immunol.* 91:207–213; Chachuoa et al., 1994, *J. Immunotherapy* 15:217–224; Schuurman et al., 1994, *Cancer Immunol. immunother.* 39:179–184. But again, as the skilled artisan will know, many other assays can be employed.

In certain embodiments of the invention, the compositions may comprise additional components which, for example, may act synergistically with the immunomodulating peptide.

In one embodiment, the peptides of the invention may be employed in combination such that a plurality of peptides are administered to a host in an amount effective to activate cells of the monocyte/macrophage lineage and/or other lymphoid cells The combined administration of a plurality of active peptides may be advantageous in that the different peptides may have synergistic/potentiating effects. Although the combined administration of peptides is not intended to be limited to such cases, the amount of such peptides effective to activate cells of the monocyte/macrophage lineage and/or other lymphoid cells might be smaller when a plurality of active peptides is employed. The different peptides may be administered in a combination dosage or separately.

Again, although the compositions used in the present invention are not intended to be limited to such theoretical cases, the amount of the active peptides effective to activate cells of the monocyte/macrophage lineage and/or other lymphoid cells might be smaller when such peptide is administered together with a conventional antibiotic.

In another embodiment, the peptides or analogues or derivatives thereof useful in the present invention may be administered in combination with conventional antibiotics. The active peptide(s) and the antibiotic may act in a synergistic/potentiating manner. Preferably, the conventional antibiotic is selected from the group consisting of bacitracins, gramicidin, polymyxin, vancomycin, teichoplanin, aminoglycosides, hydrophobic antibiotics, penicillins, monobactams, or derivatives or analogues thereof.

Bacitracins, gramicidin, polymyxin, vancomycin, teichoplanin, and derivatives and analogues thereof, are a group of peptide antibiotics. Aminoglycoside antibiotics include tobramycin, kanamycin, amikacin, the group of gentamycins, netilmicin, kanamycin, and derivatives and analogues thereof. Penicillins used may include but are not limited to benzyl penicillin, ampicillin, methicillin (dimethoxyphenyl penicillin), ticaricillin, penicillin V (phenoxymethyl penicillin), oxacillin, cloxacillin, dicloxacillin, flucloxacillin, amoxicillin, and amidocillin. Examples of preferred hydrophobic antibiotics which may be used in the present invention are macrolides such as erythromycin, roxythromycin, and clarithromycin. Further 9-N-alkyl derivatives of erythromycin, midecamycin acetate, azithromycin, flurithromycin, ribabutin, rokitamycin, 6-0-methyl erythromycin-A known as TE-031 (Taisho), rifapentine, benzypiperazinyl rifamycins such as CGP-7040, CGP-5909, CGP,279353 (Ciba-Geigy), an erythromycin-A derivative with a cyclic carbamate fused to the $C_{11}/C_{12}$ position of a macrolide ring know as A-62514 (Abbott), AC-7230 (Toyo Jozo), banzoxazinorifamycin, diffacidin, dirithromycin, a 3-N-piperdinomethylzaino methyl rifamycin SV know as FCE-22250 (Farmitalia), M-119-a (Kirin Brewery), a 6-0-methyl-1-4"-0-carbamoyl erythromycin known as A-63075 (Abbott), 3-formylrifamycin SV-hydrazones with diazabicycloalkyl side chains such as CGP-27557 and CGP-2986 (Ciba-Geigy), and 16-membered macrolides having a 3-0-alpha-L-cladinosyl moiety, such as 3-0-alpha-L-cladinosyldeepoxy rosaramicin, tylosins and acyl demycinosyl tylosins.

In addition to the macrolides hereinabove described, rifamycin, carbenicillin, and nafcillin may be employed as well.

A special set of antibiotics is used for the treatment of mycobacterial infections such as TB. Examples of antibiotics specifically efficacious for mycobacteria are isonaizid, ethionamide, ethambutol and pyrazidamide. In addition, rifampin is frequently used in combination with the mycobacteria-specific drugs listed above.

Other antibiotics which may be used (hydrophilic or hydrophobic) are antibiotics which are 50S ribosome inhibitors such a lincomycin, clindamycin, chloramphenicol, etc.; further, antibiotics which have a large lipid like lactone ring, including mystatin, pimaricin, etc.

The peptide or the peptide in combination with an antibiotic may be administered by direct administration to a target cell or by systemic including parenteral oral, intravenous, subcutaneous, intramuscular, transmucosal, nasal, pulmonary, transdermal, etc., or topical administration to a host which includes the target cell, in order to prevent, destroy or inhibit the growth of a target cell. Target cells whose growth may be prevented, inhibited, or destroyed by the administration of the peptides and antibiotic include gram-positive and gram-negative bacteria, mycobacteria, fungal cells and protozoa parasites.

The peptide and the antibiotic may be administered in a composition comprising both the active peptide(s) and the antibiotic(s) or in separate compositions.

The antibiotic, such as those hereinabove described, or derivatives or analogues thereof, when used topically, is generally employed in a concentration of about 0.10 to about 10%. When used systemically, the peptide or derivative or analogue thereof is generally employed in an amount to achieve a serum peptide level of about $10^{-9}$ M to about $10^{-5}$ M, more typically of about $10^{-9}$ M to about $10^{-6}$ M.

In general, such serum levels may be achieved by incorporating the peptide into a composition to be administered systemically at a dose of from 0.0005 mg/kg to about 5.0 mg/kg body weight typically about 0.0005 to about 0.5 mg/kg body weight. In general, the peptide need not be administered at a dose exceeding 5 mg/kg body weight. Peptide dosages may be those of hereinabove described, ie., the active peptide(s) is administered in an amount effective to activate cells of the monocyte/macrophage lineage and/or other lymphoid cells in a human or non-human animal.

In yet another embodiment, the peptides of the present invention may be administered in combination with an antiparasitic agent or an antifungal agent.

Antiparasitic agents which may be employed include, but are not limited to, anti-protozoan agents. Examples of specific anti-parasitic agents which may be employed include, but are not limited to, ketoconazole and fluronazole. It is also to be understood that certain anti-parasitic agents any also have anti-fungal activity, and that certain anti-fungal agents may have anti-parasitic activity. As far example, amphiterocin B or fluronazole.

The peptide and the antiparasitic or the antifungal agent may be administered in a composition comprising both the active peptide(s) and the antiparasitic or the antifungal agent or in separate compositions.

In yet another embodiment, the peptides of the present invention may be administered in combination with antihistamine drug.

Pentavalent antimonial compounds are the standard of treatment for leishmaniasis. Examples include stibogluconate sodium (Pentostam) and meglumine antimoniate (Glucantime). In addition, pentamidine (Lomidine), amphotericin B and allopurinol are used for this indication.

In still another embodiment, the peptides of the present invention may be administered in combination with an antibiotic which inhibits DNA gyrase, which is an enzyme involved in the formation of bonds between individual coiling strands of replicating bacterial DNA. Thus, DNA gyrase is necessary for the normal replication of bacterial DNA, and, therefore, antibiotics which inhibit DNA gyrase inhibit the normal replication of bacterial DNA.

Examples of antibiotics which inhibit DNA gyrase include nalidixic acid, oxolinic acid, cinoxacin, and quinolone antibiotics which include ciprofloxacin, norfloxacin, ofloxacin, enoxacin, pefloxacin lomefloxacin, fleroxacin, tosulfloxacin, temafloxacin, and rufloxacin.

In still another embodiment, the peptides or analogues or derivatives thereof may be administered in combination with an agent for the treatment of cancer, including but not limited to cytotoxic and/or cytostatic compounds, e.g., cyclophosphamide, cisplatin, doxorubicin, hexamethylamine, or VP-16. The peptide and the anticancer agent may be administered in a combined composition separately.

In still another embodiment, the peptides or analogues or derivatives thereof useful in the present invention may be employed in combination with agents that inhibit proteases. Such agents include, but are not limited to, bestatin, amastatin, aprotinin, pepstatin, and leupeptin. The peptide(s) and protease inhibitor(s) may be administered as a single composition or in separate compositions. The single or separate compositions may, of course, include materials, active or inactive, in addition to the peptide(s) or protease inhibitor(s).

In employing both the peptide(s) and protease inhibitor (s), whether administered or prepared in a single composition or in a separate compositions, the peptide and the protease inhibitor are employed in amounts effective to activate cells of the monocyte/macrophage lineage and/or other lymphoid cells Although the scope of this particular embodiment is not intended to be limited to any theoretical reasoning, it is believed that in effect the protease inhibitor potentiates the action of the peptide, and the peptide potentiates the action of the protease inhibitor. Accordingly, the effective amount of the peptide may be lower as it is for the administration of the active peptide without a protease inhibitor.

C. Preparation of the Peptides and Compositions

The peptides of the compositions used for the methods of the present invention may be produced by known techniques and obtained in substantially pure form. For example, the peptides may be synthesized on an automated peptide synthesizer or by conventional solution phase chemistry. Most commonly used currently are solid phase synthesis techniques; indeed, automated equipment for systematically constructing peptide chains can be purchased. Solution phase synthesis can also be used but is considerably less convenient for small scale synthesis but can be the preferred method for production scale synthesis. When synthesized using these standard techniques, amino acids not encoded by the gene and D-enantiomers can be employed in the synthesis. Thus, one very practical way to obtain the compounds of the invention is to employ these standard chemical synthesis techniques.

In addition to providing the peptide backbone, the N- and/or C-terminus can be derivatized, again using conventional chemical techniques. The compounds of the invention may optionally contain an acyl group, preferably an acetyl group at the amino terminus. Methods for acetylating or, more generally, acylating, the free amino group at the N-terminus are generally known in the art; in addition, the N-terminal amino acid may be supplied in the synthesis in acylated form.

If the peptides of the intention are prepared under physiological conditions, the side-chain amino groups of the basic amino acids will be in the form of the relevant acid addition salts.

Because the peptides are cationic at a physiological pH, the peptides can be prepared in the form of a salt including, but not limited to, triflouro acetate, acetate, hydrochloride, etc. Berge et al., 1977, *J. of Pharm. Science* 66:1–19.

Formation of disulfide linkages, if desired, is conducted in the presence of mild oxidizing agents. Chemical oxidizing agents may be used, or the compounds may simply be exposed to the oxygen of the air to effect these linkages. Various methods are known in the art. Processes useful for disulfide bond formation have been described by Stewart et al., 1984, "Solid Phase Peptide Synthesis" 2d Ed. Pierce Chemical Company Rockford, Ill.; Ahmed et al., 1975, *J. Biol. Chem.* 250:8477–8482. An additional alternative is described by Kamber et al., 1980, *Hely Chim. Acta.*63:899–915. A method conducted on solid supports is described by Albericio, 1985, *Int. J. Pept. Protein Res.* 26:92–97.

A particularly preferred method is solution oxidation using molecular oxygen.

Alternately, the peptides may be purified from their natural source by methods which are well-established in the art. Examples of such methods can be found, among other places, in Mor et al., 1994, *Proc. Acad. Sci. USA* 91:10295–10299; Mor et. al., 1991, *Biochemistry* 30:8824–8830; Mor et. al, 1994, *Biochemistry* 33:6642–6650.

If the peptide backbone is comprised entirely of gene-encoded amino acids, or if some portion of it is so composed, the peptide or the relevant portion may also be synthesized using recombinant DNA techniques. The DNA encoding the peptides of the invention may itself be synthesized using commercially available equipment; codon choice can be integrated into the synthesis depending on the nature of the host.

Synthesized and recombinantly produced forms of the compounds may require subsequent derivatization to modify the N- and/or C-terminus and, depending on the isolation procedure, to effect the formation of cystine bonds as described hereinabove. Depending on the host organism used for recombinant production, some or all of these conversions may already have been effected.

For recombinant production, the DNA encoding the peptides of the invention is included in an expression system which places these coding sequences under control of a suitable promoter and other control sequences compatible with an intended host cell. Types of host cells available span almost the entire range of the plant and animal kingdoms. Thus, the compounds of the invention could be produced in bacteria or yeast (to the extent that they can be produced in a nontoxic or refractile form or utilize resistant strains) as well as in animal cells, insect cells and plant cells. Indeed, modified plant cells can be used to regenerate plants containing the relevant expression systems so that the resulting transgenic plant is capable of self protection vis-a-vis these infective agents.

The compounds of the invention can be produced in a form that will result in their secretion from the host cell by fusing to the DNA encoding the peptide, a DNA encoding a suitable signal peptide, or may be produced intracellularly. They may also be produced as fusion proteins with additional amino acid sequence which may or may not need to be subsequently removed prior to the use of these compounds as antimicrobials or antivirals.

Thus, the compounds of the invention can be produced in a variety of modalities including chemical synthesis, recombinant production, isolation from natural sources, or some combination of these techniques.

D. Use of the Peptides and Compositions: Methods for the Treatment of Diseases

The present invention provides methods for the treatment of a variety of diseases. Generally, the therapeutic methods of the present invention comprise the administration of compositions comprising one or a plurality of the cationic amphipathic α-helical peptides as disclosed herein and are based on the modulating effects of such peptides on the immune system. Specifically, the compositions used for the methods of the invention contain an amount of such peptides effective to activate cells of the monocyte/macrophage lineage and/or other lymphoid cells in the serum of a human or non-human host. According to their activity as modulators of the immune system, the compositions of the invention have a broad range of applications in the treatment and the prevention of diseases.

The compositions may be administered either prophylactically or therapeutically. Accordingly, the human or non-human host may be afflicted by a disease, or, alternately, may be healthy and the composition be administered solely for the purpose of preventing the host from developing a disease.

In one embodiment, the compositions of the invention are used for the treatment or prevention of infectious diseases, such as diseases caused by a variety of microorganisms including gram-positive and gram-negative bacteria, mycobacteria, filamentous fungi, yeast, protozoa, and the like, including parasites and certain viruses. Diseases treated with the compositions and by the methods of the invention include, but are not limited to, malaria, trypaniasomiasis, leishmaniasis, amebiasis, filariasis, bilariasis, echinococcosis, leprosy, tuberculosis, opportunistic infection with *M. avium* and *M. intracellulare* (collectively referred to as *M. avium* complex [MAC]), cholera, meningococcal meningitis, polio, hepatitis, acute diarrhea, and HIV infection/AIDS. As the skilled artisan will appreciate many other diseases will be subject for treatments comprising embodiments of the methods of the present invention, according to their broad applicability.

In another embodiment the compositions and methods of the invention may be used for promoting or enhancing the process of wound healing in an afflicted human or non-human host. For example, the active peptides may reverse the inhibition of wound healing caused by conditions which depress or comprise the immune system or by infection. The compositions and methods may further be used to for the treatment of external burns and to treat and/or prevent skin and burn infections.

In another aspect of the invention, the compositions are used for the treatment or prevention of cancer. As cancer development involves the generation of abnormal cells in the afflicted organism, activation of the immune system might be an effective method for the treatment, or, alternately, prevention of such group of diseases. The compositions of the invention may be administered alone or in combination with other modes of cancer treatments, such as radiation therapy, chemotherapy, or surgery. Chemotherapeutic agents administered in combination with the peptides of the present invention may include chemotherapeutic agents, i.e., cytotoxic and/or cytostatic compounds including, but not limited to, cyclophosphamide, cisplat in, doxorubicin, hexamethylamine, and VP-16. The peptide may be administered before, during or after such radiation treatment, chemotherapy, or surgery. The administration of the compositions comprising the peptides of the present invention may, for example, result in a enhanced immunological response and in the destruction of malignant cells.

E. Formulations and Routes of Administration

The peptides useful in the present invention and/or analogues or derivatives thereof may be administered to a host, for example a human or non-human animal, in an amount effective to activate cells of the monocyte/macrophage lineage and/or other lymphoid cells.

The peptide or protein may be administered to a host in vivo, such as, for example, through systemic administration such as subcutaneous, intravenous, intramuscular, intraperitoneal administration, etc. In employing such systemic administrations the active peptide is present in an amount effective to activate cells of the monocyte/macrophage lineage and/or other lymphoid cells. Generally, active peptide is present in an amount to achieve a serum level of the peptide of about $10^{-9}$ M to about $10^{-5}$ M. Preferably, the serum level will be about $10^{-9}$ M to about $10^{-6}$ M. In accordance with the different embodiments of the invention where the active peptide is administered in combination with an adjuvant or another active compound the effective amount of such peptide may vary.

The amount of peptide to be incorporated into a composition to be administered systemically to achieve such serum levels may be determined by assays that are well-known to those of skill in the pharmaceutical arts. In general, such serum levels may be achieved by incorporating the peptide into a composition to be administered systemically at a dose of from 0.0005 mg/kg to about 5.0 mg/kg body weight typically about 0.0005 to about 0.5 mg/kg body weight. In general, the peptide need not be administered at a dose exceeding 5 mg/kg body weight.

The pharmaceutical compositions comprising the active peptides provided by the present invention may be manufactured in a manner that is itself known, e.g., by means of conventional mixing, dissolving, granulating, dragee-making, levigating, emulsifying, encapsulating, entrapping or lyophilizing processes. Pharmaceutical compositions may be formulated in conventional manner using one or more physiologically acceptable carriers comprising excipients and auxiliaries which facilitate processing of the active compounds into preparations which can be used pharmaceutically. Proper formulation is dependent upon the route of administration chosen.

For injection, the agents of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form with bulking agents for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as by recent novel drug delivery technologies that is described in Wealey, 1991, *Critical Reviews in Therapeutic Drug Carrier Systems* 8:331–394; Roehrborn et al., 1995, *Antimicrobial Agents and Chemotherapy* 39:1752–1755; Sanders, 1990, *European Journal of Drug Metabolism and Pharmacokinetics* 15:95–102.

Some of the compounds of the invention may be provided as salts with pharmaceutically compatible counterions. Pharmaceutically compatible salts may be formed with many acids, including but not limited to hydrochloric, sulfuric, acetic, lactic, tartaric, malic, succinic, etc. Salts tend to be more soluble in aqueous or other protonic solvents that are the corresponding free base forms.

Pharmaceutical compositions suitable for use of the compounds provided by the present invention include compositions wherein the active ingredients are contained in an effective amount to achieve its intended purpose. More specifically, a therapeutically effective amount means an amount effective to prevent development of or to alleviate the existing symptoms of the subject being treated. Determination of the effective amounts for effecting desired biological, chemical or other effects is well within the capability of those skilled in the art.

Selected embodiments of the present invention will now be described in the following examples. However, the scope of the present invention is not understood to be limited to the examples given.

VI. EXPERIMENTAL EXAMPLES

A. Example 1

SPYY Induced Activation Of Macrophages

Skin peptide YY (SPYY) and other related neuroactive peptides are shown to be endowed with broad spectrum antibiotic activity in vitro. The C-terminal α-helical domain that is common in these peptides is responsible for lysis of microorganisms, probably through membrane permeation. When administered to Balb/c mice which developed cutaneous leishmaniasis consequently to infection with *Leishmania major* protozoan parasites, SPYY induces healing of the treated mice. According to the old theory, healing may be due to the participation of cell mediated immunity as, in vitro, killing of intracellular parasites correlated with nitric oxide production. However, as the following experimental example shows, the potent therapeutic effect of SPYY results from its ability to activate cells of the monocyte/macrophage lineage and/or other lymphoid cells.

Chromatography of skin extract of the South American tree frog *Phyllomedusa bicolor* displays three distinct antifungal fractions Mor et al., 1994, *Biochemistry* 33:6642–6650. The activity of two of these fractions is due to two closely related peptides belonging to the dermaseptin family of antimicrobial peptides, the antifungal activity of the third fraction is due to the recently identified Skin Peptide YY (SPYY) (YPPKPESPGEDASPEEMNKYLTALRHYINLVTRQRY-NH$_2$) SEQ ID NO: 1 whose structure closely resembled that of NPY and PYY, exhibiting 72% and 94% amino acid positional identity respectively. Mor et al., 1994, *Proc. Natl. Acad. Sci. USA* 91:10295–10299.

To establish its antimicrobial activity, the synthetic replica of SPYY was investigated for its ability to affect the viability of various prokaryotic and eukaryotic cells in culture media. To control for any compounds carried over in the peptide preparation, a helical acidic synthetic peptide (EEEKRENEDEEKQDDEQSEM) SEQ ID NO: 116 was prepared and used in parallel in all the following experiments under the same conditions. The effect of the acidic peptide was generally equivalent to the untreated control experiments. The ability to inhibit cell proliferation is reported in terms of minimal inhibitory concentration, defined as the lowest peptide dose at which 100% inhibition growth was observed after 24 hours of incubation. As shown in TABLE I, SYPP inhibited the proliferation of a large spectrum of pathogenic microorganisms including bacteria, yeasts, filamentous fungi and protozoa at peptide concentration ranging between 10 and 100 µg/ml.

Interestingly, a short peptide version of SPYY, PEEMNKYLTALRHYINLVTRQRY-NH$_2$ (SPYY$_{14-36}$) SEQ ID NO: 6 representing the C-terminal α-helical portion of SPYY which is highly conserved among the PP family members showed that the truncation of the N-terminal 13 residues did not alter the peptide's antimicrobial properties (TABLE I). In fact, SPYY$_{14,36}$ displayed a comparable molar potency as that of the parent molecule against most microorganisms assayed.

Methods. Peptide synthesis and purification was as described in Mor et al., 1994, *Proc. Natl. Acad. Sci. USA* 91:10295–10299. Antimicrobial assays were performed as described in Mor and Nicolas, 1994, *J. Biol. Chem.* 269:1934–1939. The effect on leishmania was assessed after 1 hour peptide exposure by counting living cells following trypan blue inclusion. Promastigotes were cultured (1×10$^5$ cells/ml) at 26° C. Amastigotes were purified from the cutaneous lesion of infected mice, as described in Monjour et al., 1984, *Ann. Trop. Med. Parasitol.* 78:423–425, and cultured (1×10$^4$ cells/ml) at 37° C. Reversibility of inhibition was assessed by incubating 0.5 ml suspension containing 1×10$^6$ cells/ml in culture media in presence of peptide concentration of 0.2 mg/ml. After various incubation periods, aliquots were centrifuged at 900 g, the pellet washed and reincubated for 24 hours in fresh culture medium.

TABLE I

Spectrum of antimicrobial activity of SPYY and SPYY14-36.

| Organism | SPYY | SPYY$_{14-26}$ | MIC$^a$ (µg/ml) DS$^b$ |
|---|---|---|---|
| Aeromonas caviae | 60 ± 12 | 40 ± 10 | 50 ± 10 |
| Escherichia coli | 15 ± 3 | 10 ± 2 | 5 ± 1 |
| Enterococcus faecalis | 20 ± 5 | 10 ± 2 | 25 ± 5 |
| Nocardia brasiliensis | 30 ± 6 | 20 ± 5 | 100 ± 40 |
| Cryptococcus neoformans | 25 ± 5 | 20 ± 5 | 15 ± 3 |
| Candida albicans | 25 ± 5 | 15 ± 3 | 60 ± 12 |
| Microsporum canis | 10 ± 2 | 40 ± 10 | 50 ± 10 |
| Tricophyton rubrum | 15 ± 3 | 15 ± 3 | 100 ± 20 |
| Arthroderma simii | 15 ± 3 | 10 ± 2 | 100 ± 20 |
| Aspergillus fumigatus | 100 ± 20 | 80 ± 20 | 100 ± 20 |
| Leishmania major (promastigotes) | 25 ± 5 | ND | 25 ± 5 |
| Leishmania major (amastigotes) | 25 ± 5 | ND | 25 ± 5 |

$^a$each minimal inhibitory concentration (MIC) was determined from 2 independent experiments performed in duplicate. No inhibition was observed with the acidic peptide up to 200 µg/ml.
$^b$The spectrum of dermaseptin (DS) is shown for comparison (Mor and Nicolas, 1994, J. Biol. Chem. 269:1934–1939)
ND, not determined.

To verify the reversibility of inhibition, treated suspensions were thoroughly washed at various periods and reincubated in fresh medium. Washed microorganisms that were exposed to SPYY for 24 hours, did not proliferate after 48 hours of incubation. These results remained unchanged when suspensions were exposed to SPYY for 1 hour or 10 minutes. This indicated that the effect was rapid and irreversible Antimicrobial activity was investigated for the SPYY related peptides human NPY and PYY. Despite differences in primary structure (located mostly within the N-terminal segment), the three peptides exhibited inhibitory activity at comparable concentrations under the same experimental conditions.

Figure 1:
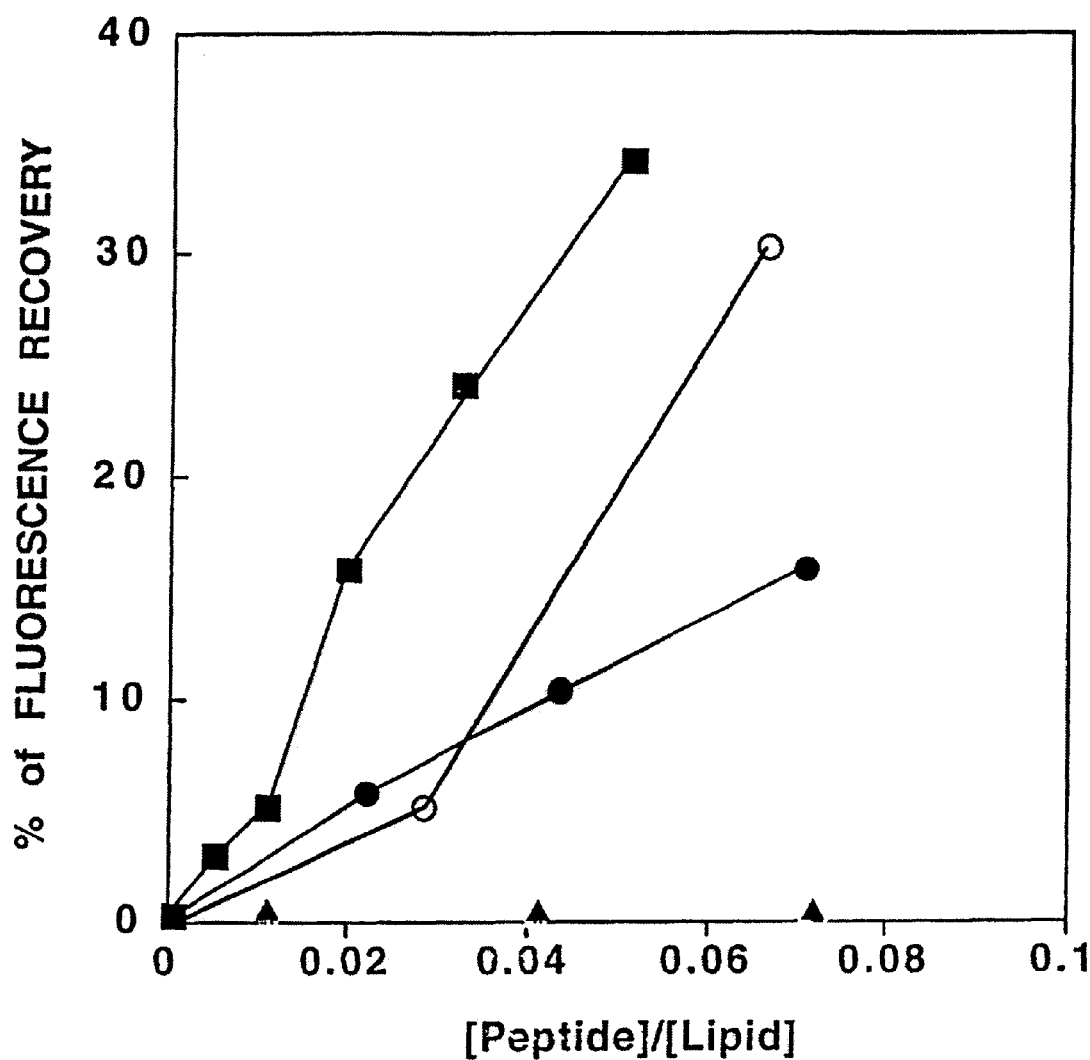

SPYY and its shorter version, were also examined for the efficacy in perturbing the lipid packing and causing leakage of vesicular contents by utilizing the Dissipation of Diffusion Potential Assay (FIG. 1). Albeit with different potencies, both peptides permeated phospholipid vesicles, a property that is characteristic of well defined antimicrobial peptides, e.g., cecropin (Steiner et al., 1988, *Biochim. Biophys. Acta* 939:260–266), magainin (Westerhoff et al., 1989, *Proc. Natl. Acad. Sci. USA* 86:6597–6601) or dermaseptin (Pouny et al., 1992, *Biochemistry* 31:12416–12423).

Methods: Small unilamellar vesicles (SUV) were prepared by sonication of PC/PS (1:1 w/w) and cholesterol (10% by weight) as described in Shai et al., 1991, *J. Biol. Chem.* 266:22346–54. Membrane permeation was assessed using the diffusion potential assay. Sims et al., 1974, *Biochemistry* 13:3315–3330; Shai et al., 1991, *J. Biol. Chem.* 266:22346–54. Increasing concentrations of the peptide were mixed with SUV that had been pretreated with the fluorescent potential-sensitive dye (diS-C$_2$-5) and valinomycin. Recovery of fluorescence was monitored as a function of time and usually occurred within 1 to 10 minutes. Maximal activity of the peptides was plotted versus peptide/lipid molar ratio. Each point represents the mean of 3 to 6 separate experiments with standard deviation of ±5%.

To determine the efficacy of SPYY in affecting pathogenic agents in vivo, the murine-induced leishmaniasis model was employed in which mice were inoculated with *Leishmania major*, a protozoan parasite that is responsible for a world wide human disease. Hart, Ed., 1989, Leishmaniasis, Plenum, New York. 30 days after inoculation, infected mice developed high parasite levels, accompanied with characteristic cutaneous lesions that attained 3 cm diameter in average. Treatment consisted of three intravenous injections of SPYY, five days apart.

Figure 2A:
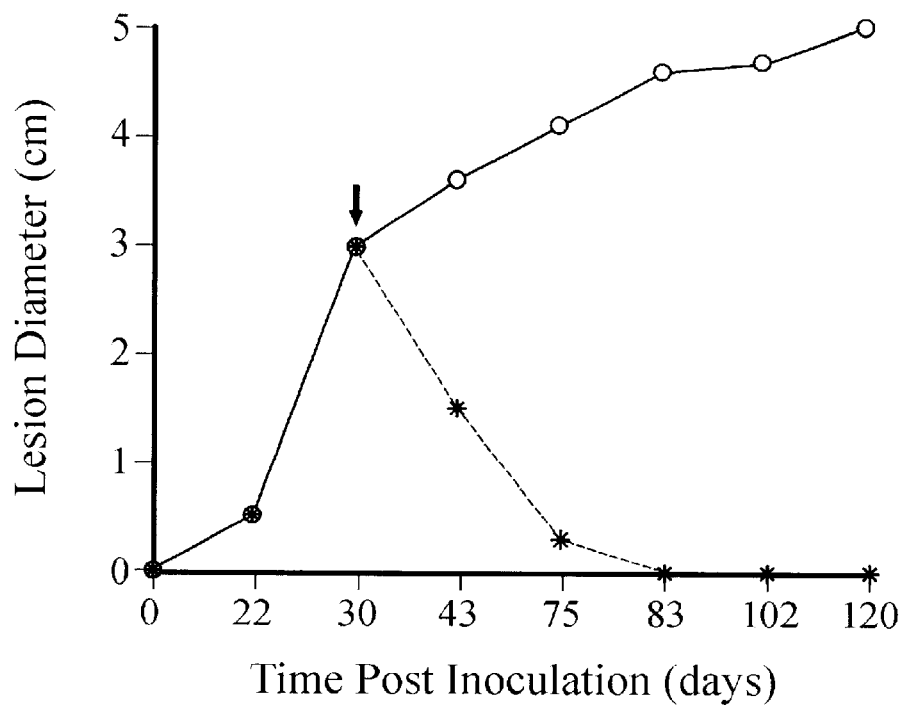
Figure 2B:
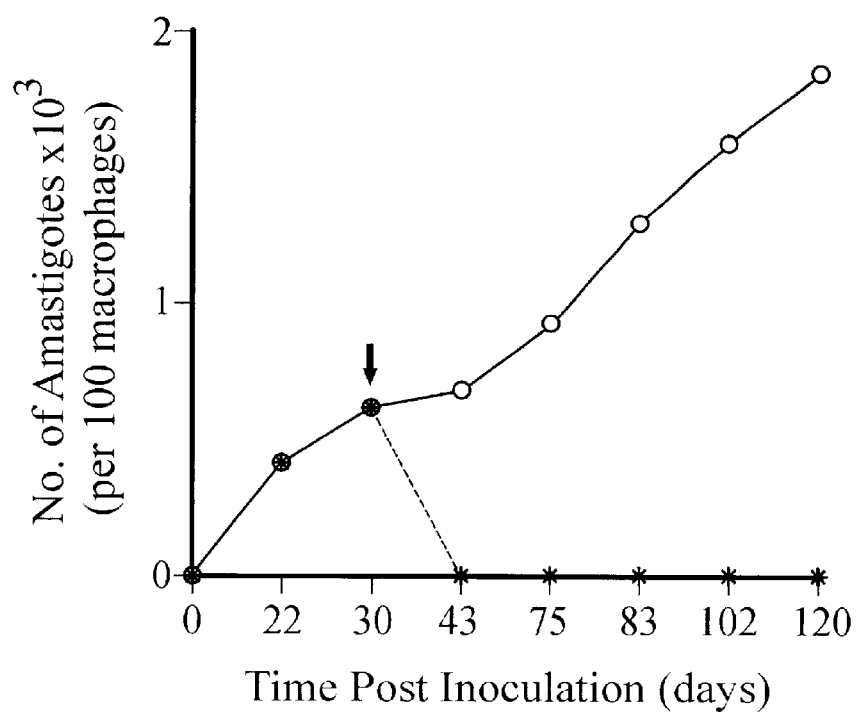
Figure 3A:
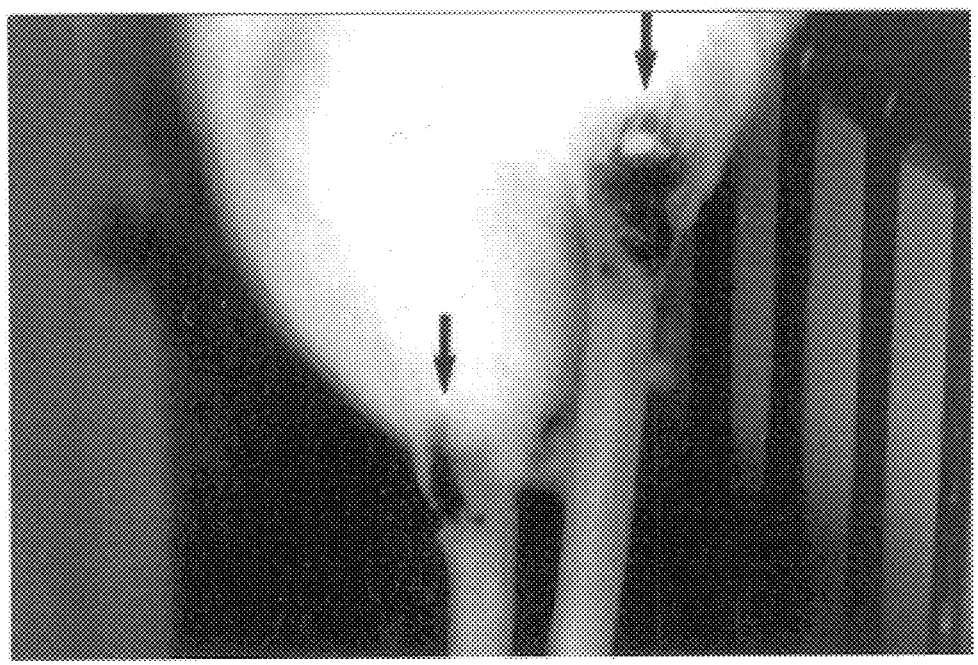
Figure 3B:
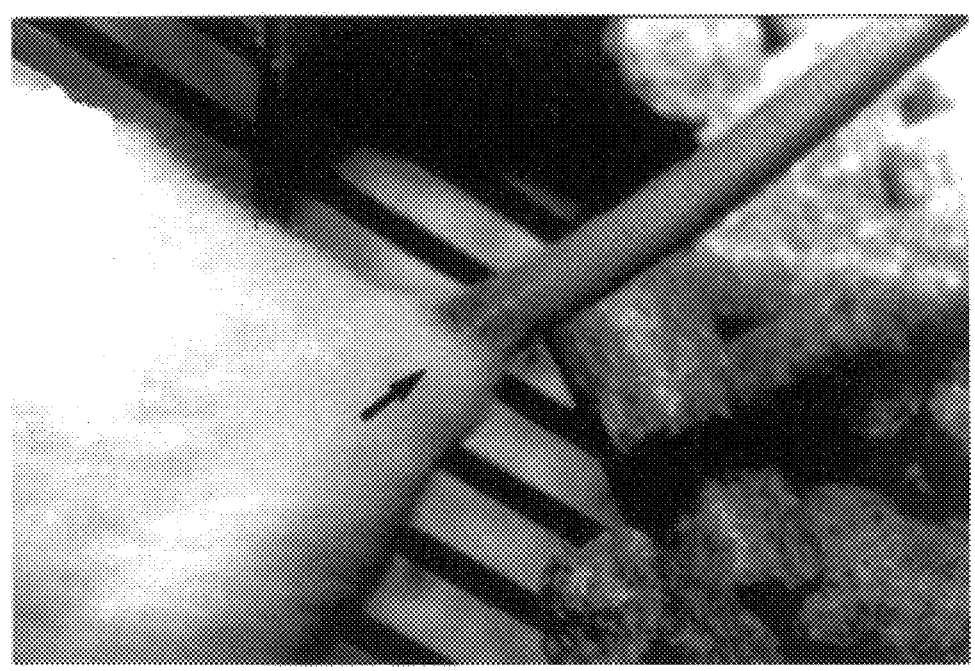

At day 13 of treatment onset, the direct examination revealed significant decline in size of the inflammatory area (FIG. 2A). Within 6 to 8 weeks, the lesion disappeared and the skin was completely reconstituted (FIGS. 3A and 3B). Samples drawn at day 13 of treatment onset from treated and untreated mice were analyzed and compared with respect to the number of infected macrophages (FIG. 2B). Analysis of these samples revealed a population of <2% infected macrophages compared with >66% for the untreated mice. The viability of intracellular parasites was verified by culture of aliquots from the drawn samples in RPMI 1640 complete medium at 26° C. This should induce differentiation of viable amastigotes to the motile promastigote form within 24 hours. Whereas samples from untreated mice yielded >$10^6$ promastigotes/ml, treated samples did not yield observable promastigotes after 7 days of incubation. Analysis of samples drawn at day 45 of treatment displayed no infected macrophages compared with 70% infected macrophages for samples drawn from untreated mice. Whereas untreated mice developed progressively higher parasite levels and died within 3 months after inoculation, the SPYY-treated mice remained parasite free >6 months after treatment as verified through the culture of aspirates from the original ulcer site as well as the culture of lymph nodes or the spleen.

Methods: To determine the serum half life of SPYY, 200 kg were injected via the tail vein in 200 $\mu$l physiological water to healthy mice. Blood samples withdrawn at 1.5, 6, 13 and 30 min were centrifuged at 900 g and 10 $\mu$l of the resulting serum were subjected to reversed-phase HPLC. Separation conditions and peptide identification were as described. Using this method, the half life was determined to be 5.5±0.5 minutes. Infected mice were obtained by inoculation of 22 Balb/c female mice, 6 to 8 weeks old, with 1×106 Leishmania major promastigotes at the proximal portion of the tail. Frommel et al., 1988, Infection and Immunity 56:843–848. Treatment of 10 of these mice consisted in 3 intravenous injections, via the tail vein, at days 30, 35 and 40 from inoculation. Doses injected were respectively 100, 50 and 50 $\mu$g in 0.2 ml physiological water. For the control experiments, 6 mice were injected with 0.2 ml physiological water containing the acidic peptide at the same doses. Another 6 mice were injected with just physiological water. No significant differences were observed between these controls (p<0.001). The level of parasites was assessed by periodic aspiration of 50 $\mu$l fluid from the inflammatory area (Vouldoukis et al., 1987, Presse Med. 16:76–77), followed by count of infected macrophages on Giemsa stained smears. Number of cells was evaluated from a total of 500 cells counted in 20 separate fields. Variations were ±5%.

Figures 4A, 4B, 4C:
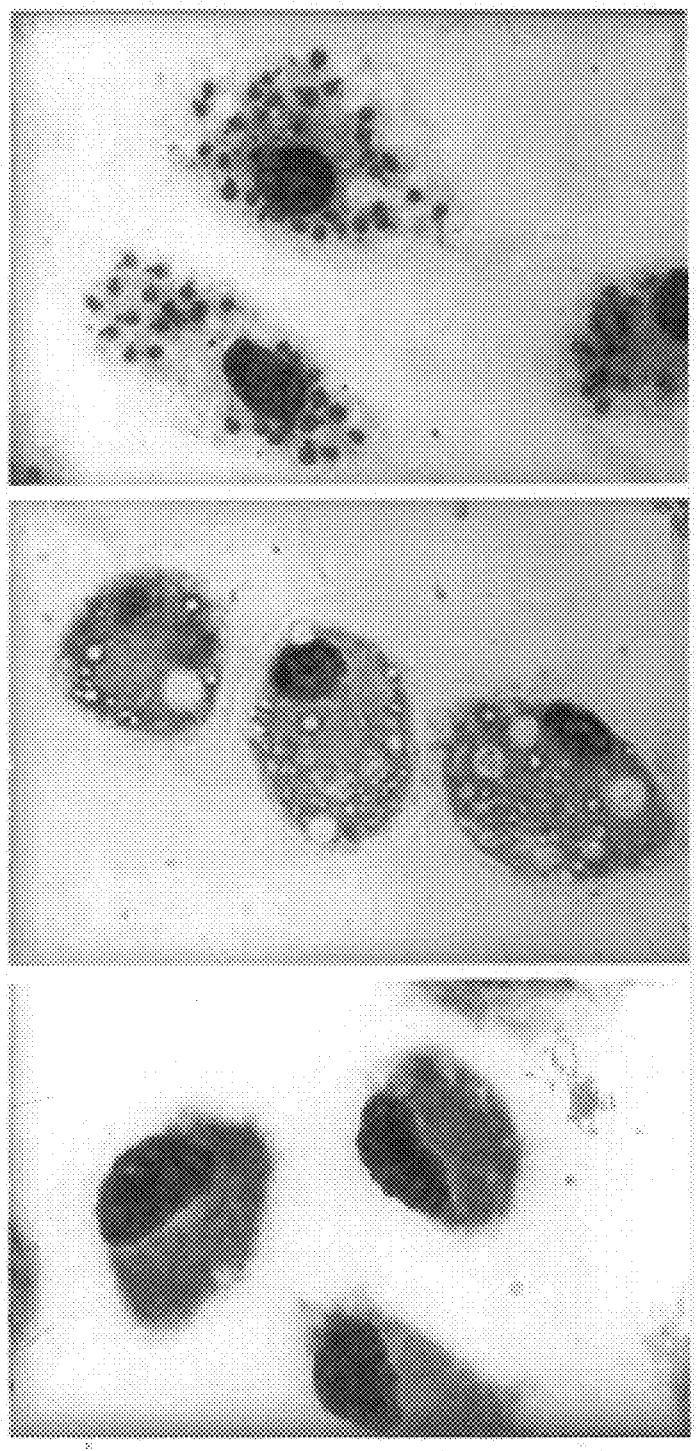

To gain insight into the mechanism of intracellular parasite elimination, infected macrophages were directly exposed to SPYY in vitro. After incubation, the number of infected macrophages was counted and culture supernatant was analyzed (TABLE II). After 24 hour treatment, the population of infected macrophages dropped to 1–5% compared with untreated cells. After 48 hours treated macrophages were transferred from an incubation temperature of 37° C. to 26° C., amastigote to promastigote differentiation was not observed after 7 days, thus confirming the killing of all intracellular parasites. No toxic signs were observed for the macrophages, while the cured macrophages displayed emptied vacuoles as evidenced after Giemsa staining (FIGS. 4A, 4B and 4C).

Analysis of the culture supernatant revealed that SPYY treatment included nitric oxide production, and parasite elimination correlated well with the $NO_2$ content which rose from <2 to 21 and 32 $\mu$M respectively after 24 and 48 hour incubation (TABLE II). Moreover, when infected macrophages were exposed to SPYY in the presence of the NO-synthase inhibitor L-NMMA (N-mono-methyl-L-arginine) for 24 hours, macrophages remained roughly as infected as in the control experiment, the level of $NO_2$ dropped to 9 $\mu$M. Replacing L-NMMA with its non-inhibitor analog D-NMMA (N-mono-methyl-D-arginine) resulted in a parasite killing outcome close to that observed with SPYY treatment in the absence of inhibitor.

Thus, these results demonstrate that in addition to its direct antimicrobial property, SPYY induces activation of macrophages. Indeed, the production of high levels of NO radicals is believed to be the main endogenous mechanism of macrophage-mediated killing of intracellular microorganisms. Support for this hypothesis was provided by the facts that (i) when directly assayed against Listeria ivanovii (strain 487) in culture medium, SPYY was unable to inhibit bacterial proliferation up to a peptide concentration of 250 $\mu$g/ml, yet, when macrophages infected with L. ivanovii were subjected to SPYY treatment, SPYY reduced the number of infected macrophages in a dose dependent manner, i.e., from 56 to 28, 24 and 180 respectively for peptide concentrations of 25, 50 and 100 $\mu$g/ml. (ii) SPYY was inefficient in curing infected macrophages when SPYY treatment was preceded by cells exposure to brefeldin A, an ER-to-Golgi transport inhibitor (TABLE II).

Methods: Infected macrophages were prepared essentially as described in Frommel et al., 1988, Infection and Immunity 56:843–848. Briefly, peritoneal resident macrophages ($2\times10^5$/ml) were exposed to infectious Leishmania major strain MRHO/SU/59/Neal P. ($1\times10^5$ promastigotes/ml) at the stationary phase of growth, in RPMI 1640 complete medium at 37° C. (in a humidified $5CO_2/95\%$ air incubator). After 24 hours of incubation, cells were washed and further incubated for 24 hours in the presence of SPYY (50 $\mu$g/ml) and/or L-NMMA (1 mM), D-NMMA (imM), BFA (50 ng/ml). The nitric oxide ($NO_2$) content was assayed in a microtiterplate by mixing 50 $\mu$L of culture supernatant with 100 $\mu$l of Griess reagent. The $A_{550}$ was read 10 minutes later and the $NO_2$ concentration was determined by reference to a standard curve of 5–1000 $\mu$M $NaNO_2$ as described in Green et al., 1981, Proc. Natl. Acad. Sci. USA 78:7764–7768. The level of infected cells was determined after wash, fixation and Giemsa staining, by counting 500 macrophages in 20 random microscopic fields in 2 separate culture dishes.

TABLE II

Leishmanicidal activity observed for SPYY-treated macrophages.

|  | No. infected macrophages | Total No. amastigotes | $NO_2$ ($\mu$M) |
|---|---|---|---|
| Macrophages + SPYY | — | — | 20 ± 2 |
| Infected macrophages | 350 ± 4 | 930 ± 10 | <2 |
| Infected macrophages + SPYY | 5 ± 9 | 10 ± 5 | 21 ± 2 |
| Infected macrophages + SPYY + L-NMMA | 290 ± 6 | 900 ± 10 | 9 ± 1 |

TABLE II-continued

Leishmanicidal activity observed for SPYY-treated macrophages.

| | No. infected macrophages | Total No. amastigotes | NO$_2$ ($\mu$M) |
|---|---|---|---|
| Infected macrophages + SPYY + D-NMMA | 25 ± 2 | 30 ± 5 | 18 ± 2 |
| Infected macrophages + BFA + SPYY | 270 ± 8 | 890 ± 10 | ND |

*Cultures were pretreated with BFA for 15 min prior to SPYY addition.
ND, not determined.

B. Example 2

Dermaseptin Induced Activation of Macrophages

As the following example will demonstrate, the natural peptide antibiotic, dermaseptin ALWKTMLKKLGTMAL-HAGKAALGAAADTISQGTQ SEQ ID NO: 7 (Mor et al., 1991, *Biochemistry* 30:8824) kills Leishmania parasites both directly and through macrophage activation.

Figure 5A:
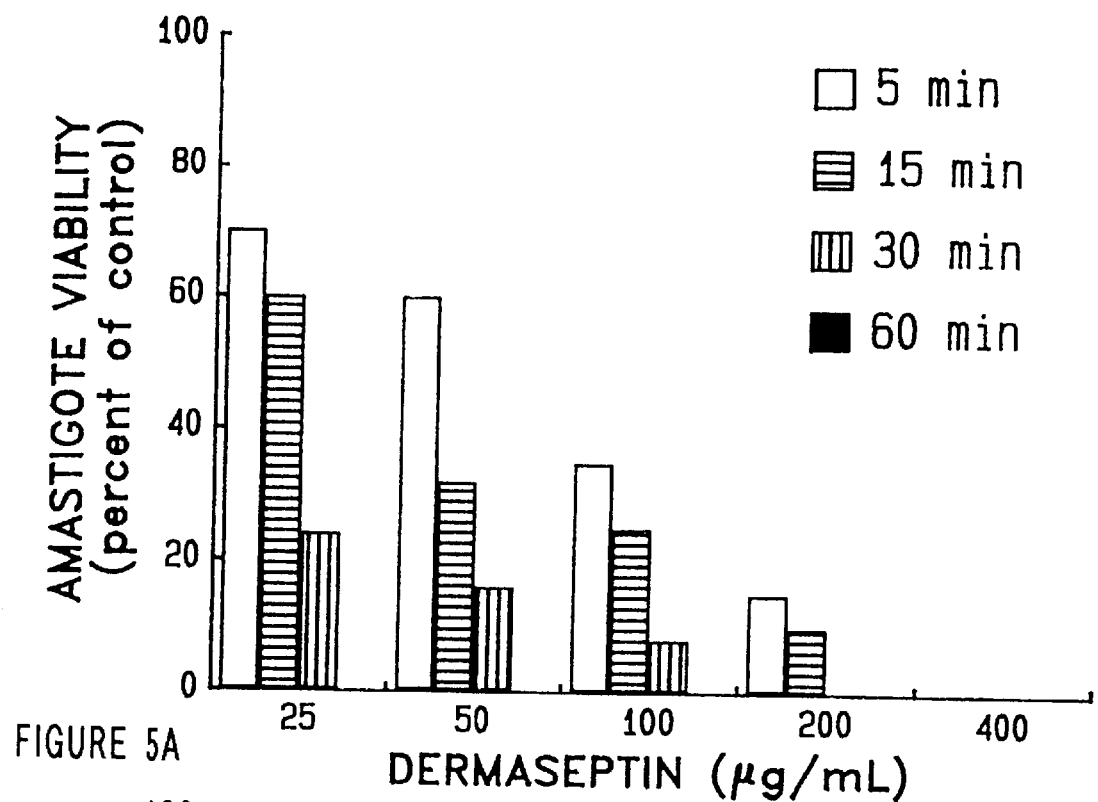
Figure 5B:
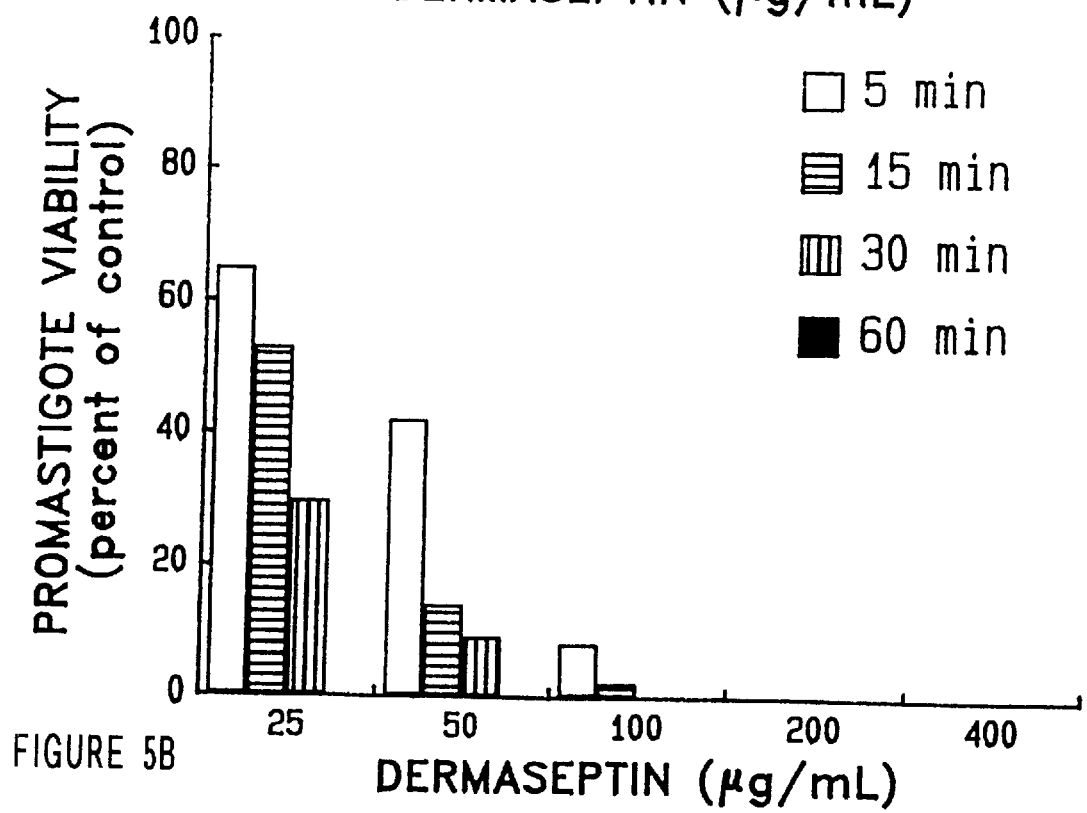

The efficacy of dermaseptin (DS) to kill parasites directly was investigated using *Leishmania major*, the responsible parasite for cutaneous leishmaniasis in man and animals. To control for any compounds carried over in the peptide preparation, an inactive peptide analog, $DS_{16-34}$ (Mor and Nicolas, 1994, *J. Biol. Chem.* 269:1934), was used in parallel in all experiments. As shown in FIGS. 5A and 5B, DS induced direct lysis of *Leishmania major* at the two stages of differentiation. At 25 μg/ml, 100% amastigotes or promastigotes were non viable within 1 hour incubation. For shorter incubation periods, the lytic effect was dose-dependent, the effect of DS on promastigotes of *Leishmania donovani*, the causal agent for visceral disease, was examined in culture medium as described in FIG. 5A amd 5B. Within 1 hour incubation, DS induced 100% parasite killing at 12 μg/ml ($LD_{50\%}$=6 μg/ml).

Methods. Dose-dependent kinetics of the leishmanicidal effect. Peptide synthesis and purification was as described in Mor et al., 1991, *Biochemistry* 30:8824. Amastigotes were purified from the cutaneous lesion of infected mice (Monjour et al., 1984, *Ann. Trop. Med. Parasitol.* 78:423) and cultured (1×10$^4$ parasites/ml) at 37° C. Promastigotes were cultured (1×10$^5$ parasites/ml) at 26° C. After incubation with DS and Trypan blue inclusion, living parasites (stained) were counted in aliquots from treated cultures and compared with non treated cultures. Each point represents the mean of 2 independent experiments performed in duplicates. Standard deviations were 510.

The effect of DS on intracellular amastigotes was investigated using cultures of infected murine macrophages. DS reduced the frequency of infection from 66% to <1% (TABLE III). The viability of intracellular parasites was verified by further incubation in drug free medium at 26° C. This should induce differentiation of viable amastigotes to the motile promastigote form within 24 hours as observed for control samples. The DS treated samples did not yield observable promastigotes after 7 days of incubation, indicating 100% killing of intracellular parasites.

Methods. Resident peritoneal macrophage (2×10$^5$ /ml) from Balb/c, C3H/HeN (C3H) and CB-17/Icr (SCID, bred in specific pathogen-free conditions) mice were infected as described in Frommel et al., 1988, *Infection and Immunity*, 56:843, using infectious *Leishmania major* strain MRHO/SU/59/Neal P. at the stationary phase of growth. Infected macrophages were then cultured (in a humidified 5% $CO_2$-95% air incubator) for 24 hours in the presence or absence of DS (50 μg/ml), L-NMMA (1 mM) and D-NMMA (1 mM). After incubation, the level of infected cells was determined after wash, fixation and Giemsa staining, by counting 500 macrophages in 20 random microscopic fields. Values shown in FIGS. 5A and 5B are from 2 independent experiments. Nitrites were measured using the Griess method by mixing 50 μL of culture supernatant with 100 μl of Griess reagent. The $A_{550}$ was read 10 minutes later and the $NO_2$ concentration was determined by reference to a standard curve of 5–1000 μM $NaNO_2$ as described in Green et al., 1981, *Proc. Natl. Acad. Sci. USA* 78:7764. The TNF-α was measured using L929 cell line and the 3(4,5-dimethyl-thiazoyl-2yl)2,5-diphenyltetrazolium bromide calorimetric assay to assess cell viability. The observed TNF activity was confirmed by blockage with anti-murine TNF antibody. Green et al., 1984, *J. Immunol. Methods* 70:257; Titus et al., 1988, *J. Exp. Med.* 170:2097. Sensitivity was lU TNF/ml. In parallel, I-A$^+$ macrophage were counted after being washed with fresh medium, fixed with acetone and incubated for 20 minutes in the presence of anti-I-Ad monoclonal antibodies (dilution of 1/100). Quantitation of I-A cell surface expression was performed using the immuno-peroxidase method (Vector Laboratories, Burlingame, Calif.) and a subsequent Mayer hemalum staining. For the control experiment, anti-IA$^d$ antibody was replaced with anti-I-A$^k$, an antibody that does not recognize the I-A antigen Cyclic nucleotides were measured by specific radio-immunoassay (Amersham Les Ulis, France) as recommended by the manufacturer.

TABLE III

Leishmanicidal activity of DS-treated murine infected macrophages.

| Cultures | IMΦ (No.) | Amastigotes (Total No.) | Nitrates ($\mu$M) | TNF-α (U/ml) | cAMP (nM) | cGMP (nM) | I-A+ (%) |
|---|---|---|---|---|---|---|---|
| Macrophages from Balb/c mice | | | | | | | |
| IMΦ | 330 ± 24 | 893 ± 43 | 2 ± 0.3 | <2 | ND | ND | 3 ± 1 |
| IMΦ + DS | 2 ± 1 | 5 ± 2 | 25 ± 3 | 64 | 6 | 4 | 53 ± 3 |
| IMΦ + DS + L-NMMA | 202 ± 12 | 881 ± 24 | 7 ± 0.7 | 4 | <0.01 | 0.7 | 29 ± 4 |
| IMΦ + DS + D-NMMA | 10 ± 1 | 34 ± 6 | 18 ± 2 | 16 | <0.01 | 2 | 43 ± 4 |
| Macrophages from C3H mice | | | | | | | |
| IMΦ | 230 ± 22 | 600 ± 40 | 3 ± 1 | <2 | ND | ND | 14 ± 2 |
| IMΦ + DS | 2 ± 1 | 3 ± 2 | 55 ± 5 | 640 | ND | ND | 68 ± 4 |
| IMΦ + DS + L-NMMA | 176 ± 12 | 462 ± 20 | 11 ± 1 | 16 | ND | ND | 48 ± 4 |
| IMΦ + DS + D-NMMA | 6 ± 1 | 13 ± 2 | 48 ± 2 | 640 | ND | ND | 65 ± 2 |

TABLE III-continued

Leishmanicidal activity of DS-treated murine infected macrophages.

| Cultures | IMΦ (No.) | Amastigotes (Total No.) | Nitrates (μM) | TNF-α (U/ml) | cAMP (nM) | cGMP (nM) | I-A+ (%) |
|---|---|---|---|---|---|---|---|
| Macrophages from SCID mice | | | | | | | |
| IMΦ | 370 ± 30 | 1200 ± 60 | 1.5 ± 0 | UD | ND | ND | 6 ± 1 |
| IMΦ + DS | 3 ± 1 | 6 ± 2 | 25 ± 3 | 64 | ND | ND | 56 ± 3 |
| IMΦ + DS + L-NMMA | 212 ± 12 | 810 ± 40 | 6 ± 0.7 | <2 | ND | ND | 42 ± 2 |
| IMΦ + DS + D-NMMA | 8 ± 1 | 11 ± 2 | 23 ± 2 | 32 | ND | ND | 51 ± 1 |

Cyclic nucleotides were measured by specific radio-immunoassay (Amersham Les Ulis, Frances) as recommended by the manufacturer.
IMΦ, infected macrophages;
ND not determined;
UD undetectable.

Intracellular parasite killing correlated with release of NO and TNF-α as well as cyclic nucleotides in the culture supernatants. Both cAMP and cGMP are known to inhibit the proliferation in a broad spectrum of cancer cells, directly or indirectly via induction of TNF-α production. Sheth et al., 1988, *Immunology* 63 :187; Wu et al., 1993, *Science* 262:1065; Cook and McCornilek, 1993, *Science* 262:1069; Gong et al., 1990, *Immunobiology* 182:44. Likewise, numerous studies showed that activated macrophages kill various pathogens and tumor cells via the NO pathway. Moncada et al., 1991, *Pharmacol. Rev.* 43:109; Liew et al., 1990, *Immunol.* 44:4793; James and Glaven, 1990, *J. Immunol.* 143:4208; Adams et al., 1990, *J. Immunol.* 144:2725; Munoz-Fernandez et al., 1992, *Immunol. Lett.* 33:35; Drapier et al., 1988, *Eur. J. Immunol.* 18:1587; Cunha et al., 1993, *J. Immunol.* 150:1908.

These results suggested that DS induced macrophage activation which led to intracellular parasite killing. Activation was confirmed by detection of I-A surface antigen on the DS-treated macrophage (I-A molecules are essential for the antigen presenting function of macrophage). Scher et al., 1980, *J. Exp. Med.* 152:1684. The population of I-A+ macrophage to anti-IA$^d$ antibodies increased from 3% up to 53%.

The effects induced by DS were all restricted in the presence of NO synthase inhibitor L-NMMA (much less by D-NMMA) which confirmed the critical role of nitric oxide radicals in the leishmanicidal effect. Green et al., 1990, *J. Immunol.* 144:278; Liew et al., 1990, *J. Immunol.* 144:4794; Liew et al., 1991, *Eur. J Immunol.* 21:3009.

Figures 6A, 6B, 6C:
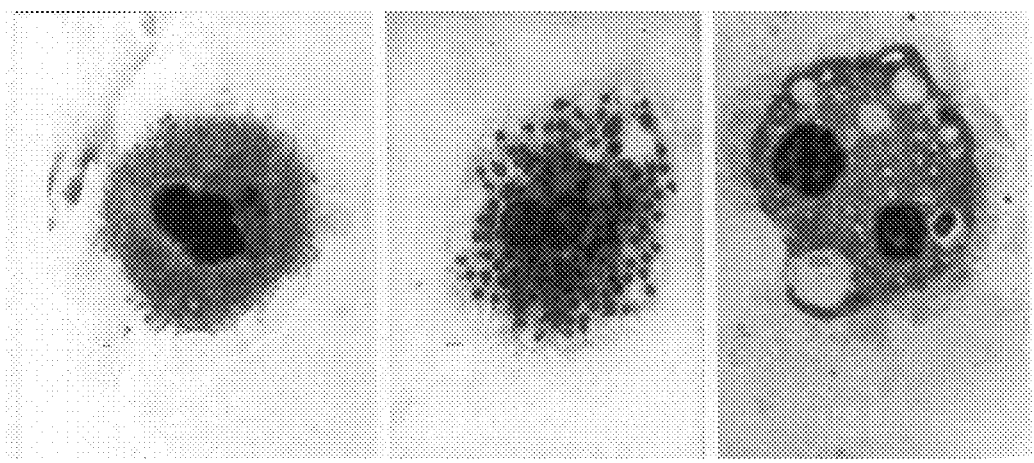
Figure 7A:
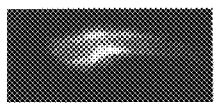
Figure 7B:
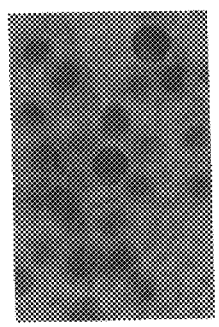
Figure 7C:
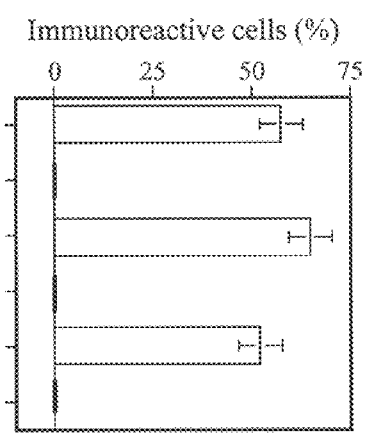

Activation and parasite killing were further observed using macrophage from either highly resistant C3H mice or from severe combined immunodeficiency (SCID) mice. Although the DS treatment was not toxic for macrophage (FIGS. 6A and 6B) DS did interact with macrophage as evidenced by immuno-localization of the peptide at the macrophage surface (FIGS. 7A, 7B and 7C). Specificity of the immuno-staining was verified by the use of presaturated anti-DS antibodies, the omission of DS and the use of preimmune serum instead of anti-DS immune serum. In the three cases, immuno-staining was abolished. In addition, peptide interaction was not observed with other cell types such as lymphocytes. The significance of these interactions is discussed below.

Methods. For the immuno-localization of DS on promastigotes and macrophages, promastigotes (1×10$^5$ parasites/ml) were exposed for 5 minutes to DS (10 μg/ml) in RPMI 1640 culture medium at 26° C. and revealed by indirect immuno-fluorescence using anti-DS antibodies (serum dilution of 1/500). Hernandez et al., 1992, *Eur. J. Cell Biol.* 59:414; Pouny et al., 1992, *Biochemistry,* 31:12416; Strahilevitz et al., 1994, *Biochemistry,* 33:10951. For visualization and quantitative analysis of the immunoreactive cells, peritoneal macrophages and spleen lymphocytes were cultured with DS (10 μg/ml) for 5 hours, then washed with fresh RPMI 1640, fixed with acetone and incubated for 30 minutes with anti-DS antibodies. Immunoreactivity was revealed using the immuno-peroxidase method (Vector Laboratories, Burlingame, Calif.) and a subsequent Mayer hemalun staining.

The efficacy of activated macrophage to resist infection was investigated using pretreated macrophage prior to being exposed to infectious parasites. After 1 hour treatment, DS induced a dose-dependent production of nitrites and TNF-α in the culture supernatants (TABLE IV). Also, pretreatment of macrophage induced a dose dependent resistance to infection, macrophage continued to release TNF-α after the promastigote challenge and expressed significant levels of I-A surface antigen. Activation and resistance to infection also correlated in DS-treated macrophage from C3H and SCID mice. Interestingly, as the data presented in TABLE IV reveal, the minimal efficient dose to achieve immunomodulating activity is between 0.0015 and 0.0031 μg/ml which is equals a concentration of approximately 10 nM. Thus, the immunomodulating effect of dermaseptin is at least 100× lower than their MICs for antimicrobial activity in vitro.

Methods. Peritoneal macrophages (2×10$^5$/ml) were cultured with DS for 1 h, subsequently nitrites and TNF-α were measured in the culture supernatants. After thorough wash, resistance to infection was investigated by exposing treated macrophages to 1×10$^5$ promastigotes for 24 h. Culture conditions, cell counts and analysis of culture supernatants were as described hereinabove.

TABLE IV

Activation and resistance to infection in DS-treated macrophages.

| DS (μg/ml) | Nitrates (μM) | TNF-α (U/ml) | Infected Cells | Total No. of amastigotes | I-A+ (%) | TNF-α (U/ml) |
|---|---|---|---|---|---|---|
| Macrophages from Balb/c mice | | | | | | |
| None | UD | UD | 298 ± 24 | 893 ± 43 | 3 ± 1 | <2 |
| 0.0007 | 1.2 ± 0.1 | UD | 112 ± 11 | 252 ± 44 | 10 ± 1 | <2 |
| 0.0015 | 1.4 ± 0.1 | UD | 54 ± 10 | 124 ± 18 | 15 ± 1 | <2 |
| 0.0031 | 5.1 ± 0.5 | <2 | 12 ± 3 | 23 ± 4 | 31 ± 2 | 8 |
| 0.0062 | 6.6 ± 0.7 | <2 | 10 ± 2 | 18 ± 2 | 40 ± 3 | 8 |
| 0.0125 | 8.1 ± 0.7 | <2 | 8 ± 1 | 17 ± 3 | 45 ± 3 | 8 |
| 0.025 | 9.1 ± 0.8 | 4 | 7 ± 1 | 10 ± 1 | 47 ± 3 | 8 |
| 0.05 | 9.5 ± 0.5 | 4 | 6 ± 1 | 8 ± 1 | 50 ± 4 | 16 |
| 0.1 | 10.1 ± 0.4 | 4 | 4 ± 1 | 6 ± 1 | 51 ± 3 | 16 |
| Macrophages from C3H mice | | | | | | |
| None | UD | UD | 234 ± 17 | 678 ± 32 | 7 ± 2 | <2 |
| 0.1 | 11.8 ± 1 | 8 | 2 ± 1 | 4 ± 1 | 65 ± 4 | 32 |
| Macrophages from SCID mice | | | | | | |
| None | UD | UD | 342 ± 30 | 1012 ± 54 | 5 ± 1 | <2 |
| 0.1 | 5.8 ± 0.2 | 4 | 11 ± 1 | 16 ± 2 | 42 ± 2 | 8 |

Analysis of culture supernatants were as described in legend of Table III.
UD, undetectable.

To investigate the peptide's efficacy in affecting leishmania parasites in vivo, murine cutaneous-leishmaniasis models were used in which mice inoculated with *Leishmania major* promastigotes were allowed to develop a characteristic cutaneous lesion that attained a mean diameter of 2.9±0.6 cm at day 27 of inoculation. Frommel et al., 1988, Infection and Immunity 56:843. Treatment consisted of 3 peptide injections at intervals of 5 days and was compared with the effect induced by sodium stibogluconate, the current anti-leishmaniasis drug of choice. After injections, samples drawn periodically from the lesion area were analyzed for assessment of parasites evolution.

As set forth in TABLE V, administration of DS resulted in cure of 100% of the diseased mice. At day 13 of treatment, the parasite load was reduced by >99% while a significant increase was observed in control mice. Aspirated samples were cultured at 26° C. in RPMI complete medium to verify the viability of intracellular parasites. Samples from $DS_{16-34}$-treated and from untreated mice yielded >105 promastigotes/ml while samples from the DS-treated mice did not yield observable promastigotes after 7 days of incubation, confirming that dermaseptin induced 100% parasite killing in vivo.

There was a marked decline in size of the inflammatory area at day 13 of treatment. From then on, the lesion diameter progressively decreased until about 7 weeks when complete skin reconstitution was observed (FIG. 8).

Three months after the observed healing, mice were verified for residual cryptic parasites that might be reactivated ultimately. This included direct examination of skin as well as footpads, spleen and draining lymph nodes which were all parasite free after 12 days of culture at 26° C.

Figure 8:
FIG. 8 depicts the cure of murine cutaneous leishmaniasis. Twelve weeks post inoculation, the cutaneous lesion displayed in the tail of the untreated mouse (left) is reduced with sodium stibogluconate and completely healed with DS treatment (right and center), respectively.

As set forth in TABLE V and in FIG. 8, although treatment with sodium stibogluconate was partially effective in reducing both the number of parasites and the lesion size, complete healing or skin cicatrization were not observed. Likewise, the untreated and the $DS_{16-34}$-treated mice developed progressively higher parasite levels that led to death from the forth month on.

Methods: Female mice, 6 to 8 weeks old, were inoculated with *Leishmania major* promastigotes ($1 \times 10^6$) at the proximal portion of the tail as described in Frommel et al., 1988, *Infection and Immunity* 56:843. Treatment consisted in 3 intravenous injections via the tail vein of 0.2 ml physiological water obtaining either DS, $DS_{16-34}$ or sodium stibogluconate (NaSG) (100, 50 and 50 μg, respectively at days 1,5 and 10). Control mice were injected with saline. Six mice were used for each experiment. To assess parasite evolution, 50 μl fluid were periodically drawn by aspiration from the inflammatory area as described in Vouldoukis et al., 1987, *Press Med.* 16:76. Count of infected macrophages was performed on Giemsa stained smears of 25 μl, the remaining 25 μl were cultured in 7 ml RPMI 1640 complete medium for 7 days at 26° C. for verification of parasite viability. Simultaneously, evolution of the cutaneous lesion was assessed by direct measurement of the necrotic zone of the lesion.

TABLE V

Effects of drug administration on infected Balb/c mice.

| | 0d[b] | 13 d | 45 d | 53 d | 90 d |
|---|---|---|---|---|---|
| | Total number of amastigotes (Mean ± SD)[a] | | | | |
| Control | 3120 ± 435 | 3375 ± 450 | 4605 ± 520 | 6435 ± 590 | 9230 ± 670 |
| DS | 2900 ± 430 | 30 ± 10 | 0 | 0 | 0 |

TABLE V-continued

Effects of drug administration on infected Balb/c mice.

| | Od[b] | 13 d | 45 d | 53 d | 90 d |
|---|---|---|---|---|---|
| $DS_{16-34}$ | 2930 ± 400 | 3250 ± 450 | 4530 ± 510 | 6100 ± 575 | 8750 ± 600 |
| NaSG | 3040 ± 375 | 1555 ± 210 | 630 ± 155 | 460 ± 110 | 380 ± 40 |
| | Average width of necrotic area in cm (Mean ± SD)[c] | | | | |
| Control | 3.1 ± 0.6 | 3.5 ± 0.7 | 4.0 ± 0.8 | 4.5 ± 0.7 | 4.9 ± 0.6 |
| DS | 2.9 ± 0.6 | 1.4 ± 0.4 | 0.2 ± 0 | (0) | (0) |
| $DS_{16-34}$ | 2.9 ± 0.7 | 3.3 ± 0.3 | 3.0 ± 0.6 | 4.0 ± 0.5 | 4.0 ± 0.6 |
| NaSG | 2.9 ± 0.6 | 2.3 ± 0.5 | 2.0 ± 0.5 | 1.8 ± 0.4 | 1.7 ± 0.2 |

[a]Number of counted cells was 500 ± 50 macrophages, evaluated in 20 separate fields on Giemsa stained smears.
[b]Determined before treatment, i.e., 27 days after inoculation.
[c]Lesion score ± standard error of the mean.
(0) Stands for complete disappearance of the lesion and reconstitution of uniform skin.

Figure 9:
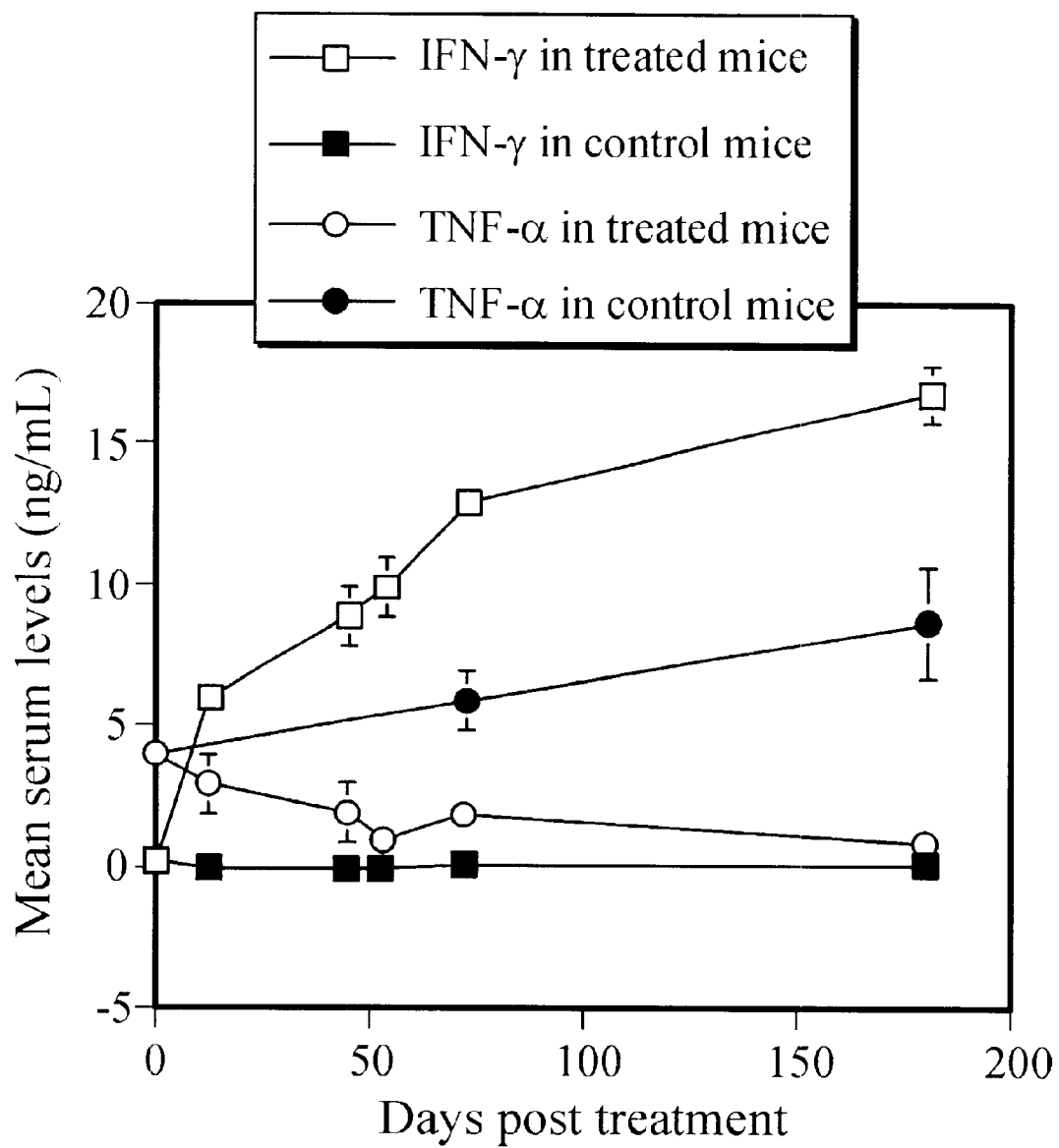
FIG. 9 depicts the cytokine concentrations in serum of treated and untreated Balb/c mice. Serum levels were determined by enzyme-immunoassay (Kit Genzyme®) using murine anti-IFN-γ or anti-TNF-α monoclonal antibodies and the corresponding rabbit polyclonal antibodies conjugated to peroxidase, following the manufacturer's instructions.

Since resolution of Leishmania major infection is associated with TNF-α and IFN-γ produced by Thi lymphocyte subset (Sadick et al., 1986, *J. Immmunol.* 136:655; Liew et al., 1990, *Immunology* 69:570), serum analysis was performed up to 6 month post treatment which revealed increased levels of IFN-γ and low levels of TNF-α for cured mice (FIG. 9). Moreover, the rise of IFN-γ was correlated with resistance to re-infection as investigated both in vitro and in vivo. In vitro, peritoneal macrophage from cured mice exposed for 5 hours to Leishmania major promastigotes (ratio 2:1) then cultured for 24 hours, were parasite free compared with 70% infected cells found in macrophage from control mice. Similarly in vivo, cured mice reinoculated with promastigotes revealed no signs of infection 6 months later. Namely, skin ulceration did not occur and cultures of aspirates either from the original site of infection or from the spleen were parasite free.

Methods. Cytokine concentrations in serum of treated and untreated Balb/c mice were determined by enzyme-immunoassay (Kit Genzyme®) using murine anti-IFN-γ or anti-TNF-α monoclonal antibodies and the corresponding rabbit polyclonal antibodies conjugated to peroxidase, following the manufacturer instructions.

Cure of leishmaniasis was also observed using SCID mice in which analysis of spleen lymphocytes confirmed absence of CD4+ and CD8+ cells. Bancroft, et al., 1986, *J. Immunol.* 137:4. Using the immunoperoxidase method, analysis of T-cell markers (Boerhinger Mannheim, France) on SCID cells with anti-Thy-1.2 (Clone 30H12, rat IgG2b), anti-L3T4/CD4 (clone H129.19 rat IgG2a) or anti-Lyt-2/CD8a (clone 53-6.7 rat IgG2a) monoclonal antibodies (dilution 1:50) revealed 0,4% Thy-1 and no L3T4+ or Lyt-2+ cells. As shown in TABLE VI, the parasite load increased with time, producing a cutaneous ulcer within 2–3 weeks after inoculation. Thirteen days after treatment, both intracellular and extracellular parasite numbers were reduced to zero and healing of skin was observed within 4–6 weeks.

Since *Leishmania major* infection in SCID mice may develop into visceral leishmaniasis (Holaday et al. 1991, *J. Immunol.* 147:1653), cultures of spleen and lymph node cells from treated and control mice were compared at day 35 from inoculation. The level of infected macrophage in these tissues was 70–72% in untreated mice, as determined by examination after Giemsa staining. Their culture yielded >2×10⁶ parasites/ml after 7 days of incubation, whereas cultures from treated mice (where no infected macrophage were detected) remained parasite free after 12 days of incubation. The fact that DS induced cure of Leishmaniasis in immuno-deficient mice points to a prominent role played by the T-cell independent pathway in fighting infection

TABLE VI

Effects of DS administration on infected SCID mice.

| | DS-treated mice | | | | | | |
|---|---|---|---|---|---|---|---|
| Days post-inoculation | 12 | 22 | 24 | 25 | 27 | 31 | 3 |
| No. of infected macrophages | 138 ± 14 | 148 ± 18 | 36 ± 3 | 30 ± 3 | 8 ± 1 | 4 ± 1 | 0 |
| No. of intercellular amastigotes | 478 ± 42 | 722 ± 44 | 118 ± 20 | 46 ± 4 | 8 ± 2 | 3 ± 1 | 0 |
| No. of intercellular amastigotes | 4 ± 1 | 8 ± 2 | 1 ± 1 | 0 | 0 | 0 | 0 |

| | Control Mice | |
|---|---|---|
| Days post-inoculation | 31 | 35 |
| No. of infected macrophages | 316 ± 32 | 378 ± 34 |
| No. of intercellular amastigotes | 3160 ± 100 | 4914 ± 200 |
| No. of intercellular amastigotes | 14 ± 2 | 18 ± 4 |

Although the mechanism of the dermaseptins' lytic action is not fully understood, previous data suggest that upon association with microbial membranes, they perturb the bilayer structure, hence, the functions governing permeability properties. Hernandez et al., 1992, *Eur. J. Cell Biol.* 59:414: Pouny et al., 1992, *Biochemistry* 31:12416; Strahilevitz et al., 1994, *Biochemistry* 33:10951. According to this hypothesis, dermaseptins do not lyse mammalian cells because of marked differences in lipid composition, membrane fluidity and charge distribution. These differences could be responsible for a differential efficiency in peptide/membrane interactions. This general scheme may provide a first lead to explain our observations in the present study and account for the fact that despite the interaction of DS with the membrane of both parasites and macrophages, lysis was induced only in the former. Moreover, if the DS-macrophage interactions can induce a mild permeation, NO-Synthase induction may have occurred following ionic imbalance. A similar mechanism was proposed for glutamate mediated activation of NOS via the NMDA receptors. Snyder and Bredt, 1992, Sci. Ani. 266:68.

In conclusion, DS appears as a unexpectedly efficient activator of macrophages, able to induce cure and rapid cicatrization of ulcered skin in murine models of a worldwide ravaging disease. Moreover, the presented data suggest that the macrophage activating properties DS may be efficient in a large variety of afflictions for which the available treatment is poorly or not effective, including bacterial, fungal, viral and tumoral pathologies.

C. Example 3

In Vivo Reversion of Th1 and Th2 Responses by Skin Peptide YY Leading to the Resolution of Leishmaniasis Cure of Leishmaniasis depends upon Th1 cells and the subsequent induction of nitric oxide generation by activated macrophages. In the following experiment, Skin Peptide YY (SPYY) is shown to induce healing of leishmaniasis in infected susceptible Balb/c or SCID mice, correlating with serum increase of interferon-γ (IFN-γ) and the decrease of interleukin-10 (IL-10).

Mounting evidence suggests that the generation of nitric oxide (NO) is an important step during anti-leishmanial immune responses of murine and human macrophages following their stimulation with Thi cytokines. Leiw et al., 1991, Eur. J. Immunol. 21:3009–3014; Munoz-Fernandez et al., 1992, Immunol. Lett. 33:35–40. For example, IFN-γ and IL-12, representative Th1 cytokines, were shown to support the healing process, while expression of IL-4 and IL-10, representative Th2 cytokines, is correlated with disease dissemination in mice. Such Th1/Th2 profile is also characteristic of a variety of other chronic infections.

To determine the efficacy of SPYY on leishmaniasis in vivo, we used the murine-induced leishmaniasis model. Specifically, mice were inoculated with *Leishmania major*, the protozoan parasite that is responsible worldwide for human and animal diseases. Hart, edt., Leishmaniasis, Plenum, N.Y. 1989. The life cycle of this parasite consists of two stages: an extracellular promastigote form characterized by an anterior flagellum, found in the gut of the phlebotomus vector, and an intracellular non-motile amastigote form that occurs within the phagolysosomes of mammalian macrophages.

Thirty days post inoculation, infected Balb/c mice developed characteristic cutaneous lesions that attained 3 cm diameter in average (FIG. 3A). Thirteen days after the first SPYY administration, direct examination revealed a significant decline in size of the inflammatory area. Within eight weeks, the lesion dissapeared completely, and the skin was completely reconstituted (FIG. 3B).

Fluids aspirated at day 13 directly from the lesions of treated and untreated mice were compared with respect to the number of intracellular amastigotes (FIG. 10A). Less than 2% infected macrophages were found in treated mice, compared to 66% in untreated mice (FIG. 10A). The viability of the intracellular parasites from these samples was verified by culture of the aliquots at 26° C. in RPMI 1640 complete medium. This treatment was expected to induce differentiation of viable amastigotes to the motile promastigote form. The fact that cultures from untreated mice yielded >$10^6$ promastigotes/ml, while those from treated mice did not yield observable promastigotes after 7 days of incubation suggested that 100% of the parasite were killed.

The next aspirate analysis, day 45 post treatment, displayed no infected macrophages in treated mice compared with 70% infected macrophages in untreated mice. Whereas untreated mice developed progressively higher parasite levels and died within 6 month post inoculation, the SPYY-treated mice remained parasite free >6 month after treatment, as it was verified through culture of aspirates from the original ulcer site as well as from culture of lymph nodes and the spleen.

Concomitantly with the observed parasite eradication, cytokine measurements in the serum established unambiguously the rise of IFN-γ in all SPYY-treated mice (FIG. 10B). Conversely, as shown in FIG. 10C, IL-10, which rose upon inoculation, was reduced to its basal level in treated mice.

Methods. Peptide synthesis and purification was as described in Mor et al., 1994, Proc. Natl. Acad. Sci. USA 91:10295–10299. Infected mice were obtained by inoculation of 22 Balb/c female mice (6 to 8 weeks old) with $1 \times 10^6$ *Leishmania major* promastigotes at the proximal portion of the tail. Ten of these mice were treated by three intravenous injections via the tail vein at days 30, 35 and 40 from inoculation. Doses injected were, respectively, 100, 50, and 50 SPYY yg in 0.2 ml physiological water. For the control experiments, six mice were injected with 0.2 ml physiological water containing a control peptide (SPYY$_{1-14}$) at the same doses. Another six mice were injected with physiological water only. No significant differences were observed between these controls.

The number of parasites was determined by aspiration of 50 μl fluids from the inflammatory area (Vouldoukis et al., 1987, Presse Med. 16:76–77), followed by a count of infected macrophages on Giemsa stained smears under the light microscope. Cells numbers were evaluated from a total of 500 macrophage counts in 20 separate fields. Serum concentrations of cytokines IFN-γ and IL-10 were determined using the enzyme linked immunosorbent assay (Genzyme Corp. Boston Mass.) and the mice immunoenzymetric assay (Medgenix Diagnosyic SA, Belgium), respectively, following the manufacturer's instructions.

The results shown in FIGS. 10A, 10B and 10C raised the possibility that SPYY induced cure of leishmaniasis through activation of the host immune system. Namely, the observed cytokine profiles suggested that SPYY may induce the Thi immune response which is presently believed to mediate resolution of murine leishmaniasis. Sadick, 1986, J. Immunol. 136:655–661. Such a scheme would involve the activation and proliferation of specific subsets of T-lymphocytes and Th1 cells which produce IFN-γ. This cytokine is an activator of the leishmanicidal function of the macrophages, in part through its ability to promote NO generation. Liew, 1990, J. Immunol. 144:4794–4797. Indeed, although the precise mechanism is not fully understood, the production of high levels of NO radicals was shown to be the main endogenous mechanism of mice and human macrophage-mediated killing of intercellular L. major. Green and Meltzer, 1991, J. Leucoc. Biol. 50:93–103; Vouldoukis, 1995, Proc. Nat. Acad. Sci. USA 92:7804–7808.

To test this hypothesis, another murine model was used, i.e., the SCID mice, which lack T lymphocytes. The absence of CD4+ and CD8+ cells in the animals was verified by analysis of the spleen cells. Bancroft et al., 1986, *J. Immunol.* 137:4–9. As shown in FIG. 11A, 13 days after treatment, the parasite load was reduced to zero. Healing of the skin was observed within six weeks. Moreover, since *L. major* infection in SCID mice may develop into visceral leishmaniasis (Guy and Beloslevic, 1995, *Exp.Immunol.* 100:440–445), cultures of spleen and lymph node cells from treated and control mice were compared at 35 days post inoculation. Cultures from treated mice remained parasite free after 12 days of incubation at 26° C., while cultures from untreated mice yielded >106 promastigotes/ml after 7 days of incubation. The level of infected macrophages in these tissues was at 72%, as determined by examination after Giemsa staining.

Interestingly, however, serum analysis of SCID mice displayed cytokine profiles similar to those observed in Balb/c mice, with a Th1-like and a Th2-like response in ing was the fact that although SPYY addition induced in all cases increase of the IFN-$\gamma$ levels, the increase was significantly more pronounced in Balb/c mice, which can produce IFN-$\gamma$ via both NK- and T-cells, than in SCID mice which lack T-cells.

Methods. Cell suspensions were prepared from gently disrupted spleens from infected or cured Balb/c and SCID mice (day 72 and 35 days post inoculation, respectively) as described After depletion of erythrocytes by treatment with Tris-ammonium chloride, cells were washed and counted, then cultured in 96-well flat bottom tissue culture plates ($5\times10^5$) cells/well) in DMEM complete medium (GIBCO) at 370 at 50 $CO_2$ and stimulated with SPYY (10 $\mu$g/ml). Cytokines (IFN-$\gamma$ and IL-10) and $NO_2$ were assayed in the culture supernatant after 48 h of incubation as described, supra. IL-4 was measured by proliferation of HT-2 cell line, using neutralizing $IgG_1$ rat monoclonal antibodies (Dr. L. Renia, INSERM, Paris, France) to control for specificity.

TABLE VII

Comparative Effect of SPYY addition in vitro to spleen cells.

| Spleen cells source | Stimulation | NO2 ($\mu$M) | IFN-$\gamma$ (pg/ml) | IL-4 (U/ml) | IL-1 (U/ml) |
|---|---|---|---|---|---|
| Infected Balb/c mice: | none | <2 | 4 ± 0.1 | 47 ± 5 | 25 ± 3 |
|  | SPYY | 10 ± 1 | 278 ± 13 | 13 ± 2 | 9 ± 1 |
| Infected SCID mice: | none | <2 | 1 ± 0.2 | <5 | 14 ± 2 |
|  | SPYY | 8 ± 0.5 | 57 ± 4 | <5 | 3 ± 1 |
| Cured Balb/c mice: | none | 5.6 ± 0.3 | 27 ± 2 | <5 | <5 |
|  | SPYY | 37 ± 3 | 1120 ± 36 | <5 | <5 |
| Cured SCID mice: | none | 4 | 16 ± 2 | <5 | <5 |
|  | SPYY | 19 ± 2 | 308 ± 14 | <5 | <5 | treated and control mice, respectively (FIG. 11B and FIG. 11C). Since activated T- and NK-cells are among the major producer cells of IFN-$\gamma$ (Bancroft et al., 1986, *Exp. Immunol.* 100:440–445), while IL-10 is widely expressed by other hematopoietic cells including macrophages, the presence of these cytokines in SCID mice is very likely due to NK-cells and macrophages.

Methods. Ten SCID mice (C. B17/Icr-scid, Taconic Lab.), maintained in specific pathogen-free conditions (P2 level), were infected as described for Balb/c mice, supra. At days 22, 27, and 32 post inoculation, five mice were injected intravenously with 100, 50, and 50 $\mu$g SPYY, respectively, in 0.2 ml physiological water. For control experiments, five mice were injected with 0.2 ml physiological water.

The number of amastigotes was estimated using the limiting dilution assay, described in Titus et al., 1985, *Parasite Immunol.* 7:545–555. The quantitative detection of IFN-$\gamma$ and IL-10 serum concentrations was performed using the mice immuno-enzymetric assay (Medgenix Diagnostics SA, Belgium).

The cure of leishmaniasis in SCID mice suggested that T-cell-mediated immune response is not required for SPYY-mediated leishmania eradication. Support for this hypothesis was provided by comparing the effect of SPYY addition in vitro to cultures of spleen cells from Balb/c and SCID mice (TABLE VII). The data show that SPYY addition induced increase of cure promoters (No and IFN-$\gamma$), but not of disease ;promoter cytokines (IL-4 and IL-10)- Moreover, the Th2 profiles displayed by spleen cells from non-treated mice were inverted following SPYY addition, as was observed in vivo following SPYY administration. Particularly interest- To further exclude the role of T lymphocytes in SPYY-dependent leishmanicidal activity, peritoneal macrophages infected in vitro were directly exposed to SPYY in culture medium. After 24 h incubation, 980 of treated macrophages were parasite free (TABLE VIII). Parasite elimination nicely correlated with the induction of NO-synthase and the $NO_2$ content in the culture supernatant which rose from <2 to 21 $\mu$M. Yet, in the presence of NO-synthase competitive inhibitor, L-NMMA, macrophages remained roughly as infected as in the control experiment, and the level of $NO_2$ dropped to 3 $\mu$M.

In addition, such NO-dependant parasite killing, induced by SPYY, was not exclusive to macrophages issued from genetically susceptible Balb/c mice since similar results were obtained with either macrophages from resistant ($C_3H$) mice or from immune deficient (SCID) mice (Table VIII).

Overall, the results obtained in this study indicated macrophages as major SPYY responding cells and clearly established that the effect of the SPYY depended upon activation of the the L-arginine:NO pathway. These results also suggested that SPYY may directly induce expression of MHC class II by macrophages. The fact that SPYY was inefficient in curing infected macrophages when SPYY treatment was preceded by cell exposure to brefeldin A, an ER-to-Golgi transport inhibitor strongly supports this hypothesis (data not shown).

Methods. Infected resident peritoneal macrophages from Balb/c, (C3H) and C. B17/Icr (SCID) mice were prepared essentially as described in Frommel et al., 1988, *Infection and Immunology* 56:843–848. Infected macrophages ($2\times10^5$/ml) were then cultured for 24 h in the presence or absence of SPYY (10 μg/ml) and L-NMMA (1 mM). The number of infected cells and $NO_2$ were determined as described, infra.

TABLE VIII

NO-mediated Leishamnicidal Activity of SPYY in vitro.

| Macrophages source | Culture conditions[a] | N° of infected macrophages | N° of infected amastigotes | NO2 (μM) |
|---|---|---|---|---|
| Balb/c mice: | Control | 350 ± 4 | 930 ± 70 | <2 |
| | SPYY | 5 ± 2 | 10 ± 5 | 21 ± 2 |
| | SPYY + L-NMMA | 290 ± 6 | 900 ± 50 | 3 ± 1 |
| C3H mice: | Control | 228 ± 6 | 612 ± 36 | 3 ± 1 |
| | SPYY | 4 ± 2 | 9 ± 1 | 51 ± 4 |
| | SPYY ± L-NMMA | 190 ± 4 | 490 ± 12 | 5 ± 2 |
| SCID mice: | Control | 370 ± 6 | 1240 ± 82 | >2 |
| | SPYY | 5 ± 2 | 8 ± 2 | 19 ± 3 |
| | SPYY ± L-NMMA | 230 ± 4 | 820 ± 18 | 4 ± 1 |

[a]To verify that experiments were performed under LPS free conditions, several precautions were taken, namely, the use of a peptide control: inactive SPYY analog ($SPYY_{1-14}$) and the limulus amoebocyte lysate assay (Immunex Corp., Seattle, WA.) to test reagents, pipette tips and labware.

To further characterize this activating effect on macrophages, non-infected macrophages were cultured in presence of SPYY prior to their exposure to *L. major*. Pretreated macrophages displayed resistance to infection in a dose dependent manner, and analysis of the culture supernatant correlated the protective effect with $NO_2$ (FIG. 12A). Moreover, macrophage activation occurred rapidly (FIG. 12B) as within 10 min. of treatment, macrophages released detectable levels of $NO_2$ and TNF-γ in the culture medium and expressed I-A surface antigens. Liew et al., 1990, *Immunology* 69:570–573.

Methods. Macrophages were obtained by wash of the peritoneal cavity of Balb/c mice with 10 ml Dulbecco's modified Eagle's medium (Gibco). Resident cells were allowed to adhere for 3 h at 37° C./5% $CO_2$ in 8-well plates (Lab-Tek) at $2 \times 10^5$ cells/well, then thoroughly washed to remove non adherant cells.

Macrophages were incubated with various SPYY concentrations for 1 h. After a thorough wash, macrophages were exposed to infections with L. major promastigotes (strain MRHO/SU/59/Neal P.) at the stationary phase of growth (ratio 1:2). After additional 24 h incubation, cells were washed, fixed and Giemsa stained. Resistance to infection was determined by counting intracellular amastigotes over a total of 500 macrophages in 20 random microscopic fields. Nitrates were measured using the Greiss reagent. The $A_{550}$ was read 10 min later and the $NO_2$ concentration was determined by reference to a standard curve of 5–1000 AM $NaNO_2$ as described in Titus et al., 1985, *Parasit. Immunol.* 7:545–555.

TNF-α was measured using L929 cell line and the 3(4, 5-dimethyl-thiazoyl-2yl) 2,5-diphenyltetrazolium bromide colorimetric assay to assess the cell viability. Green et al., 1984, *J. Immunol. Methods* 70:257–268. Sensitivity was 1U TNF-α/ml. Measure of I-A cell surface expression was performed using the avidinbiotin peroxidase method (Vector Labratories, Burlingame, Calif.) and a subsequent Mayer hemalun staining. The corressponding monoclonal antibodies (anti-I-Ad or anti-I-Ak) were used for 20 min. at a dilution of 1/100.

In conclusion, this study demonstrates the potent therapeutic effect of SPYY that led to complete resolution of leishmaniasis in Balb/c and SCID mice, mediated by the direct activation of macrophages.

D. Example 3

Therapy of Leishmaniasis with Dermaseptin in Dogs

In order to determine the therapeutic effect of the cationic amphipathic α-helical peptides of the invention in vivo, four dogs naturally infected with Leishmania were subjected to treatment with the dermaseptin DS s3 $CONH_2$. The dogs used in this study were obtained from Corsica/France, an area with endemic visceral leishmaniasis. Animal having leishmaniasis were identified based on the typical clinical symptoms, i.e., epistaxis (nasal hemorrhage), uveitis and conjunctivitis (eye inflammation), adenopathy, and cutaneous lesions in the nose. It is well-established that infected animals do not recover or improve spontaneously. To date, one of the best known therapies is treatment with the drug Glucantime®, an antimonial compound, administered at 300 mg/kg for 20–40 injections. However, Glucantime® does not cure the disease but only results in a transient reduction of the symptoms.

Methods and Results. The infected animals (ranging from 5–12 kg) were treated with a total of 1 mg DS s3 $CONH_2$ in five doses of 200 μg each given every other day for 10 days. The first two doses were administered i.v., the second three doses were administered i.m. (the dosing was selected arbitrarily).

Clinical analysis of the dermaseptin treated animals after six months revealed a substantial reduction of most symptoms, including a complete ablation of epistaxis.

For the biochemical analysis, bone marrow samples were collected in about 40 to 70 day intervals for a total of 250 days post-treatment by puncture of the sternum. The samples were analyzed via GIEMSA staining for macrophages infected by amastigotes. As illustrated in FIG. 13, treatment with dermaseptin DS s3 $CONH_2$ resulted in a substantial reduction of infected macrophages.

In order to determine the toxicity of dermaseptin DS s3 $CONH_2$, the serum LDH levels of the treated animals were determined. As the normal levels of LDH found in all animals indicate, dermaseptin in the dosages administered does not exhibit hepatotoxicity.

In conclusion, the in vivo study performed in leishmania infected dogs revealed that treatment with the dermaseptin DS s3 $CONH_2$ results in a substantial reduction of the number of infected macrophages by five doses each of about 20 μg/kg. Doses of this level could result in blood concentration of approximately 1–50 nM DS s3.

The present invention is not to be limited in scope by the exemplified embodiments which are intended as illustrations of single aspects of the invention, and any compound/peptide or method which are equivalent are within the scope of the invention. Indeed, various modifications of the invention in addition to those described herein will become apparent to those skilled in the art from the foregoing description and accompanying drawings. Such modifications are intended to fall within the scope of the appended claims.

All references cited herein are hereby incorporated by reference in their entirety.

What is claimed is:

1. A method for activating the immune system of a host comprising administering to said host at least one cationic amphipathic peptide in an amount equivalent to systemically administering between about 0.0005 mg to about 0.5 mg of said peptide per kg of body weight of said host.

* * * * *